(12) United States Patent
Loque et al.

(10) Patent No.: US 10,280,441 B2
(45) Date of Patent: May 7, 2019

(54) HOST CELLS AND METHODS FOR PRODUCING CINNAMOYL ANTHRANILATE AND ANALOGS THEREOF

(75) Inventors: Dominique Loque, Albany, CA (US); Aymerick Guillaume Eudes, Emeryville, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/274,244

(22) Filed: Oct. 14, 2011

(65) Prior Publication Data
US 2013/0078683 A1    Mar. 28, 2013

Related U.S. Application Data

(60) Provisional application No. 61/393,843, filed on Oct. 15, 2010.

(51) Int. Cl.
| | | |
|---|---|---|
| *C12P 13/02* | (2006.01) | |
| *C12N 9/10* | (2006.01) | |
| *C12N 15/81* | (2006.01) | |
| *C12N 9/16* | (2006.01) | |

(52) U.S. Cl.
CPC ............ *C12P 13/02* (2013.01); *C12N 9/1029* (2013.01); *C12N 15/81* (2013.01); *C12Y 203/01144* (2013.01); *C12Y 602/01012* (2013.01)

(58) Field of Classification Search
CPC ............ C12P 7/22; C12N 9/1029; C12N 9/93
USPC .................................. 435/254.2, 252.3, 232
See application file for complete search history.

(56) References Cited

PUBLICATIONS

Yang et al Plant Mol. Biol. 1997, 35, pp. 777-789.*
Hamberger et al Proc. Natl Acad Sci USA 2204, 101, pp. 331-340.*
Yin et al J. Biotecnol 2007, 127, pp. 335-347.*
Mukai et al J. Biosci and Bioeng. Dec. 2009, 109, pp. 564-569.*
Barthelmebs et al. Appld. & Env. Microb. 2001. pp. 1063-1069.*
Rangarajan et al. Protein Sci., 2004, 13, pp. 3006-3016.*
Knobloch et al. Eur. J. Biochem 1975, 52, pp. 311-320.*

\* cited by examiner

*Primary Examiner* — Tekchand Saidha
*Assistant Examiner* — Mohammad Y Meah
(74) *Attorney, Agent, or Firm* — Robin C. Chiang; Lawrence Berkeley National Laboratory

(57) ABSTRACT

The present invention provides for a method of producing a cinnamoyl anthranilate, or analog thereof, in a genetically modified host cell.

14 Claims, 30 Drawing Sheets

Specification includes a Sequence Listing.

A

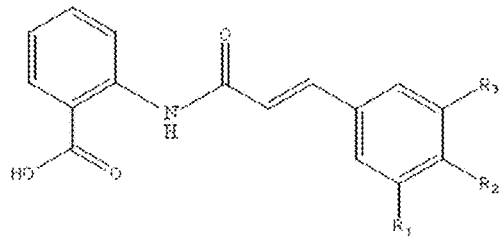

| Compound name | R1 | R2 | R3 |
|---|---|---|---|
| N-(3',4'-dimethoxycinnamoyl)-anthranilic acid (tranilast) | H | OCH$_3$ | OCH$_3$ |
| N-(3',4'-dihydroxycinnamoyl)-anthranilic acid | H | OH | OH |
| N-(3'-methoxy-4'-hydroxycinnamoyl)-anthranilic acid | H | OH | OCH$_3$ |
| N-(3',5'-dimethoxy-4'-hydroxycinnamoyl)-anthranilic acid | OCH$_3$ | OH | OCH$_3$ |
| N-(3'-methoxycinnamoyl)-anthranilic acid | H | H | OCH$_3$ |
| N-(3'-hydroxy-4'-methoxycinnamoyl)-anthranilic acid | H | OCH$_3$ | OH |
| N-(4'-hydroxycinnamoyl)-anthranilic acid | H | OH | H |

B

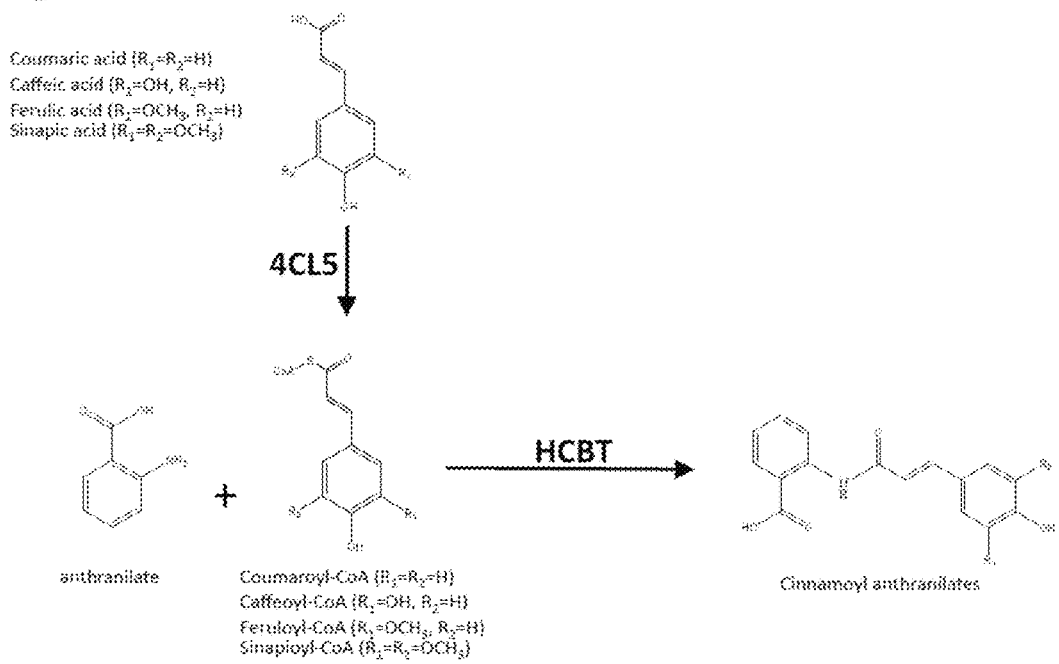

Figure 1

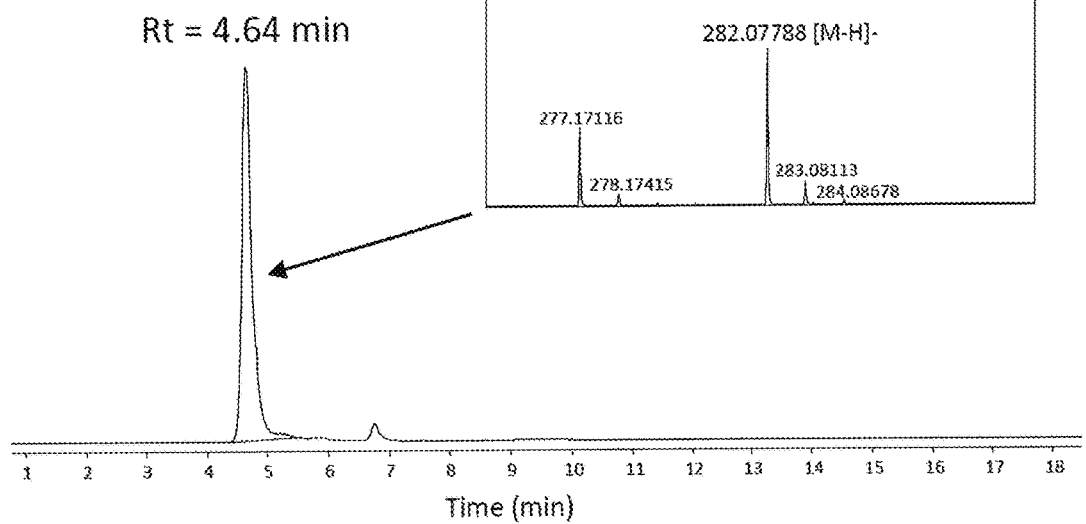
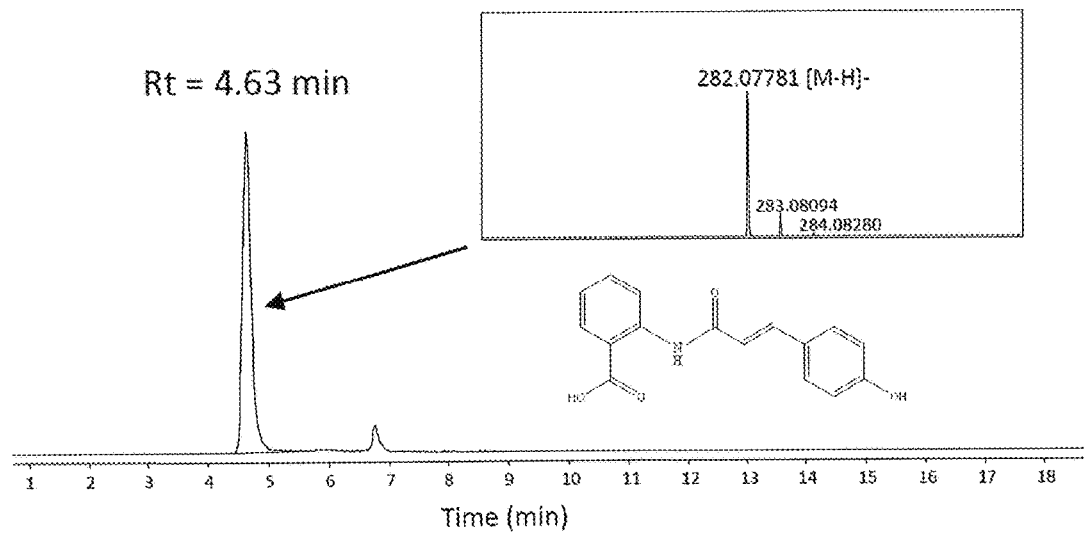
Figure 3

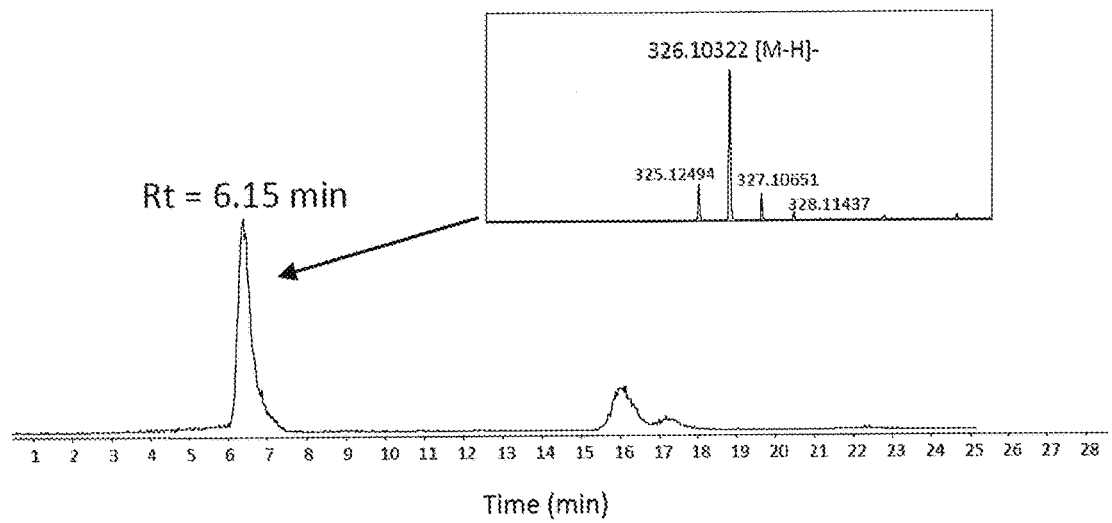
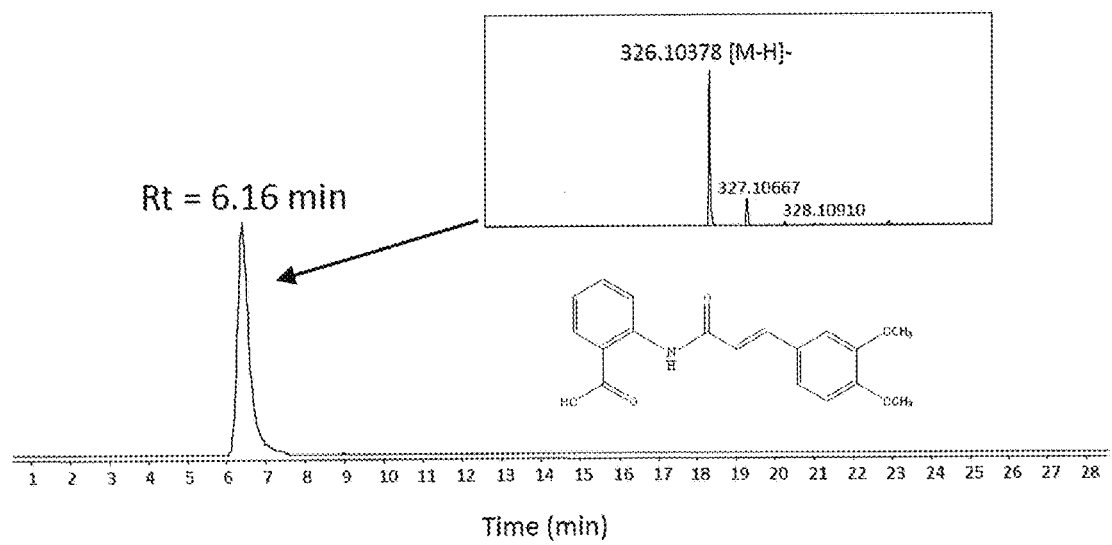
Figure 4

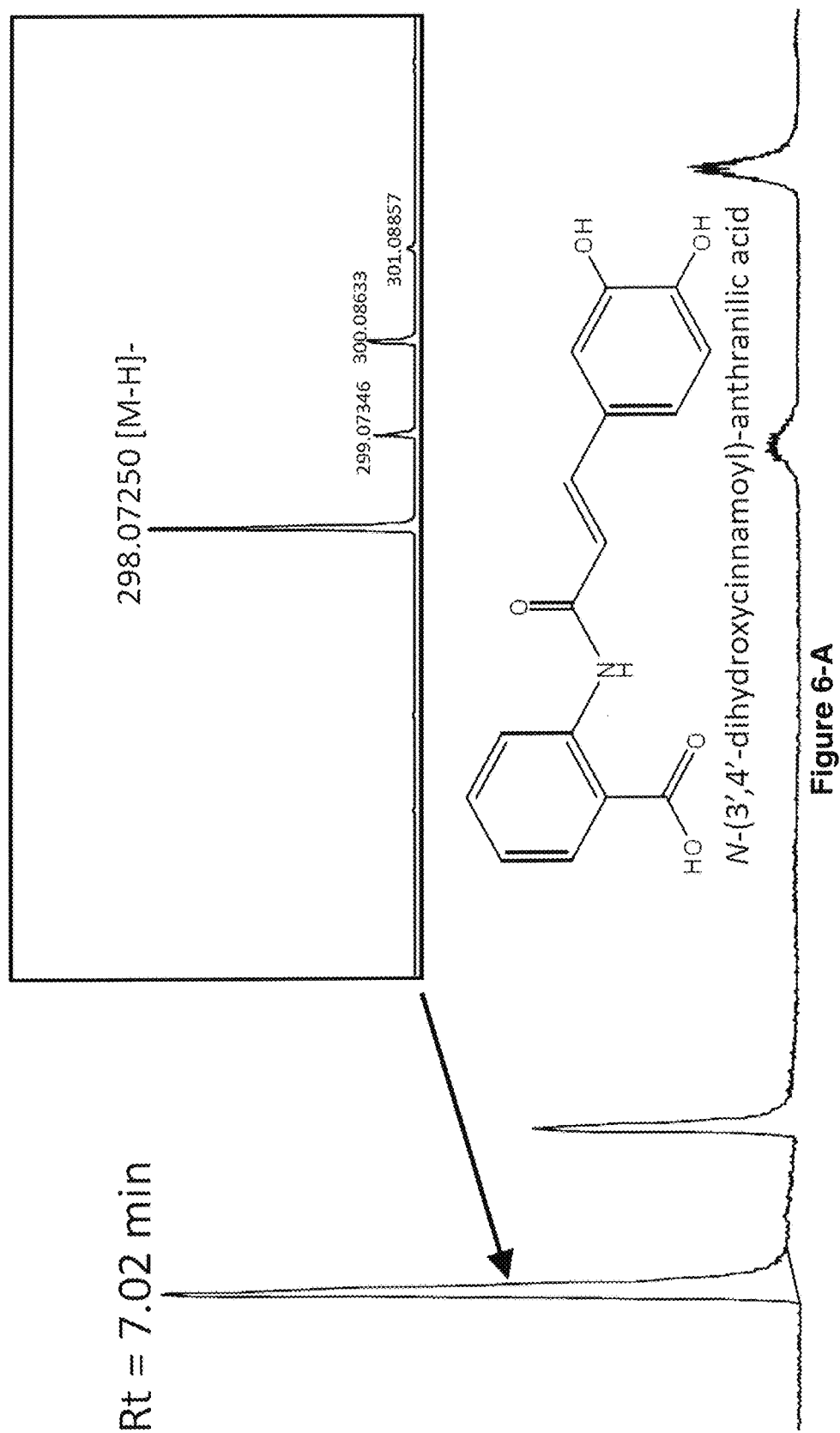
Figure 6-A

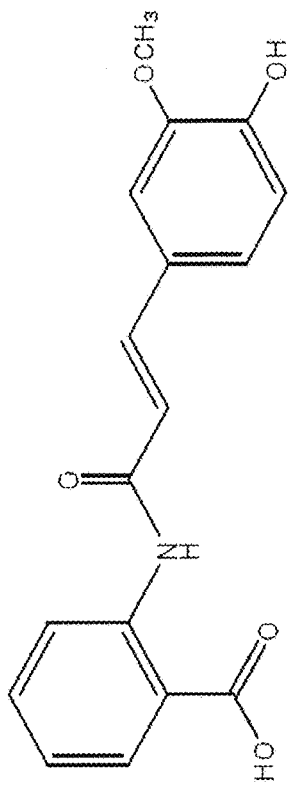
Figure 6-B
N-(3'-methoxy-4'-hydroxycinnamoyl)-anthranilic acid

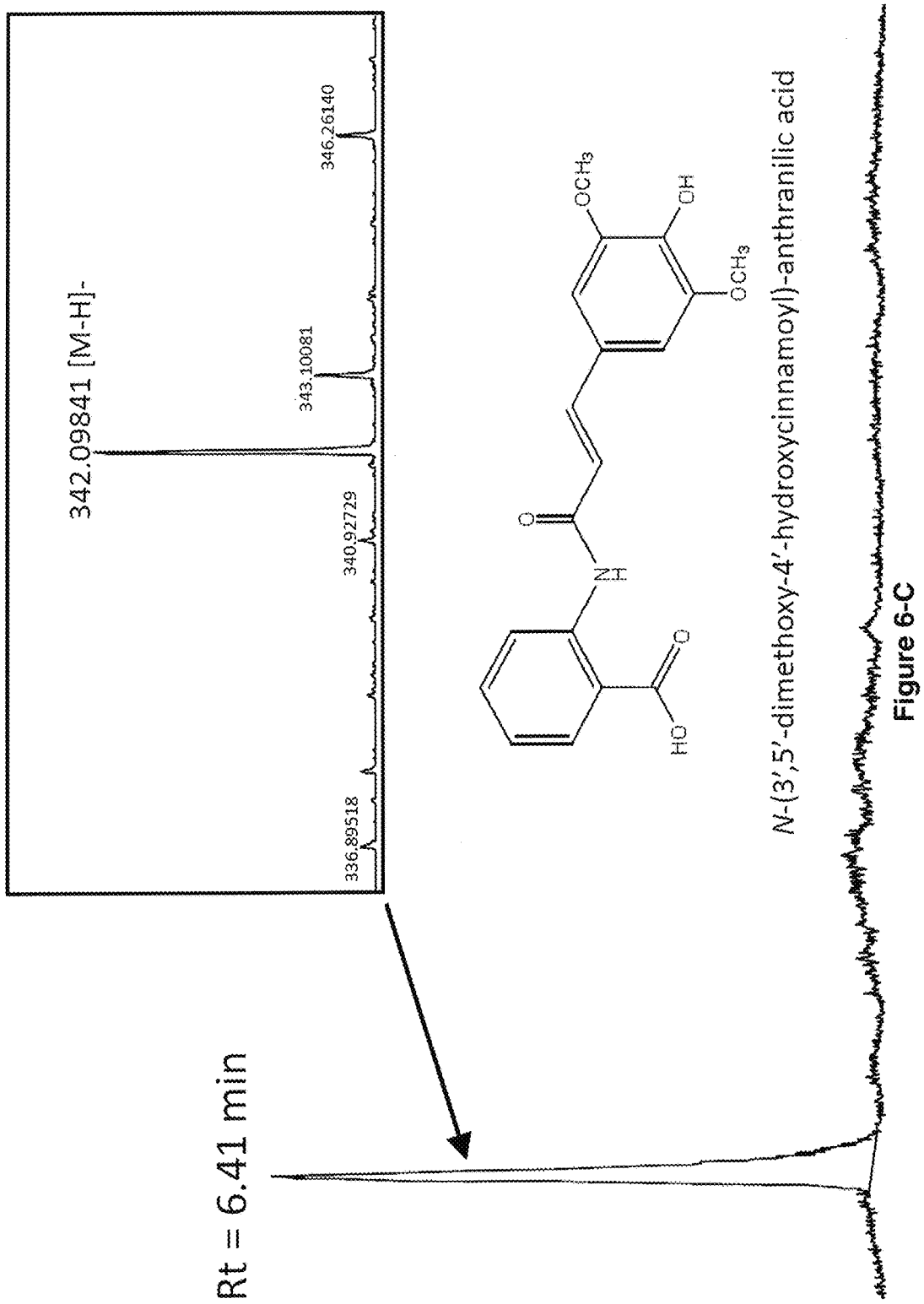

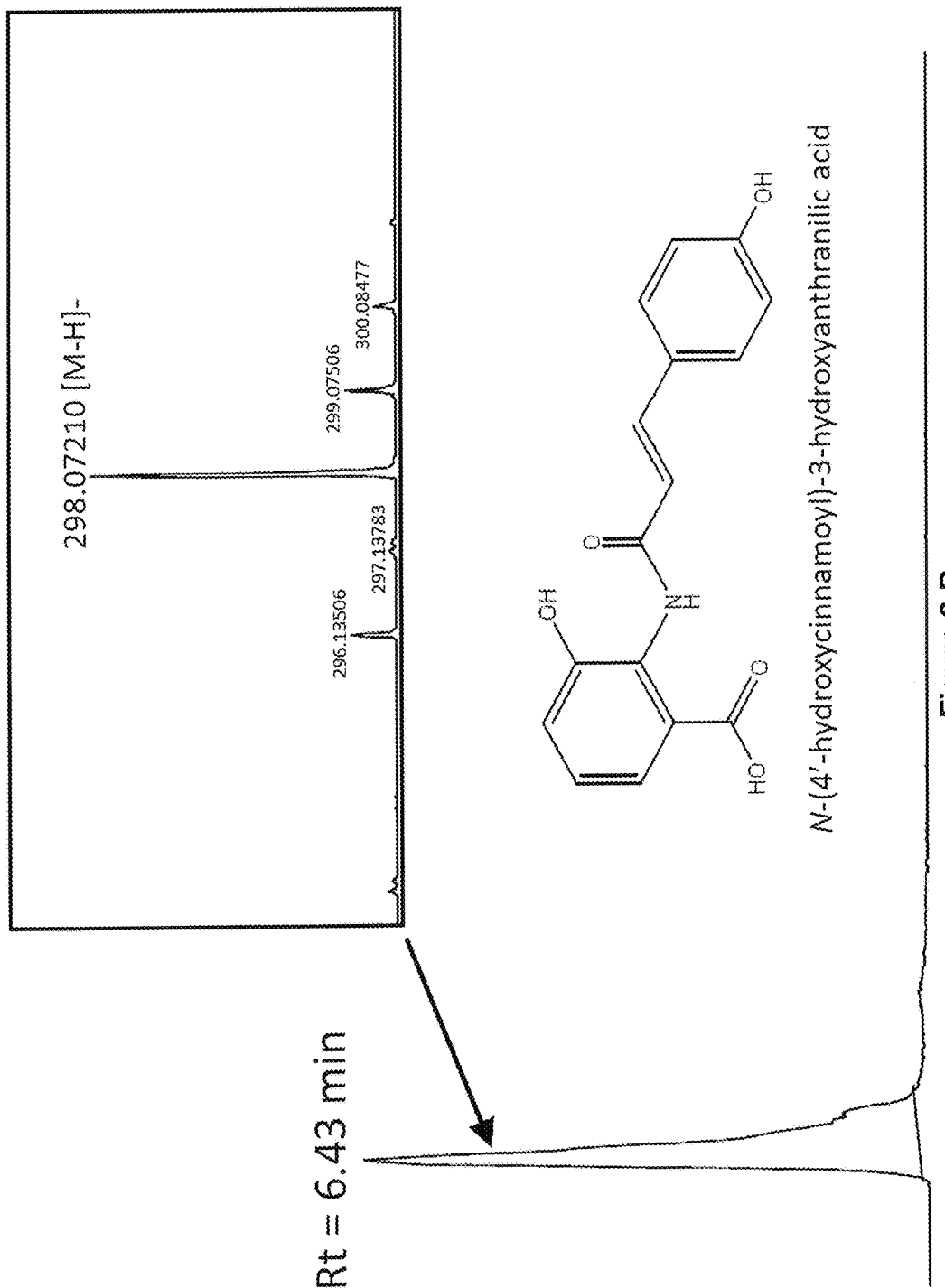
Figure 6-D

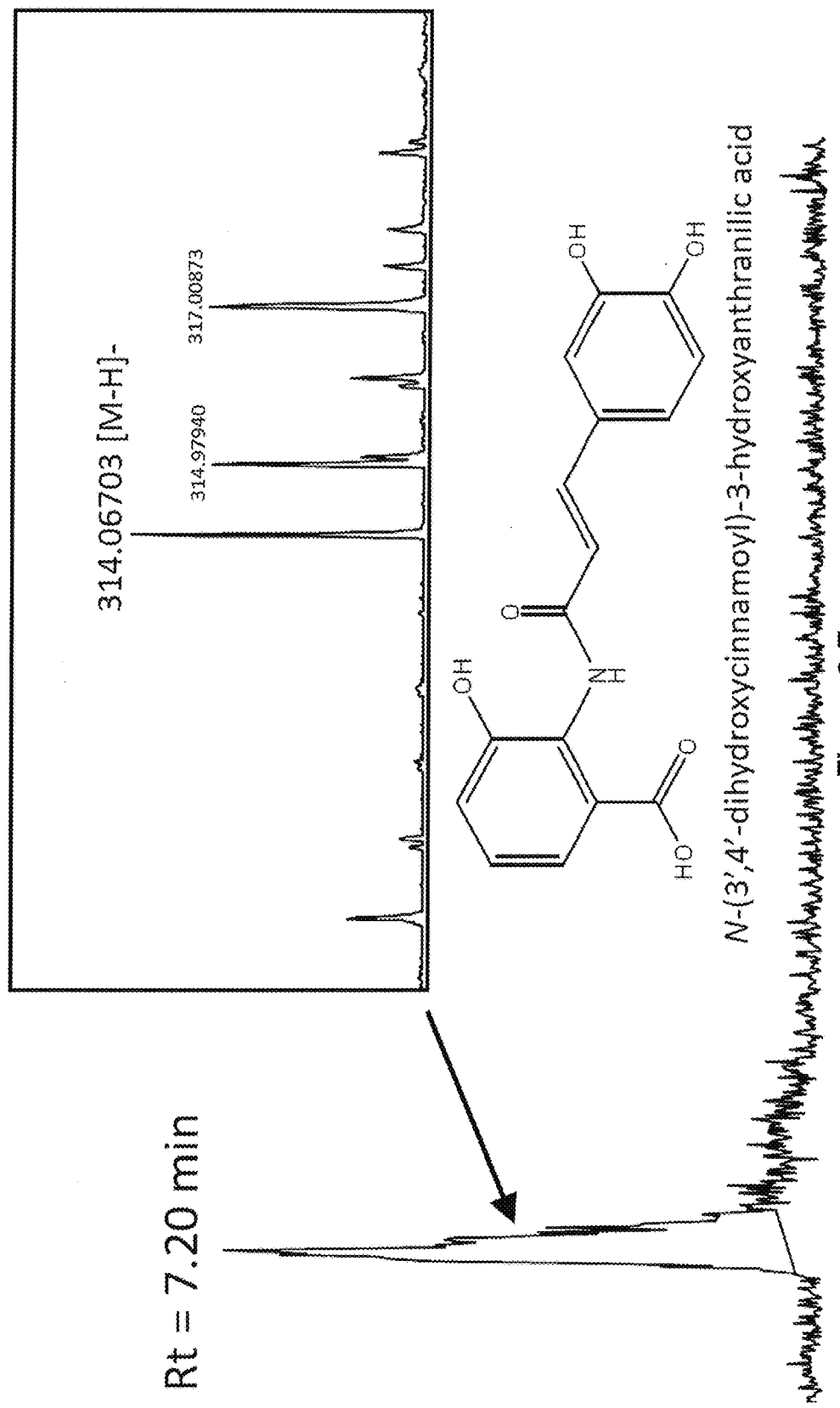
Figure 6-E

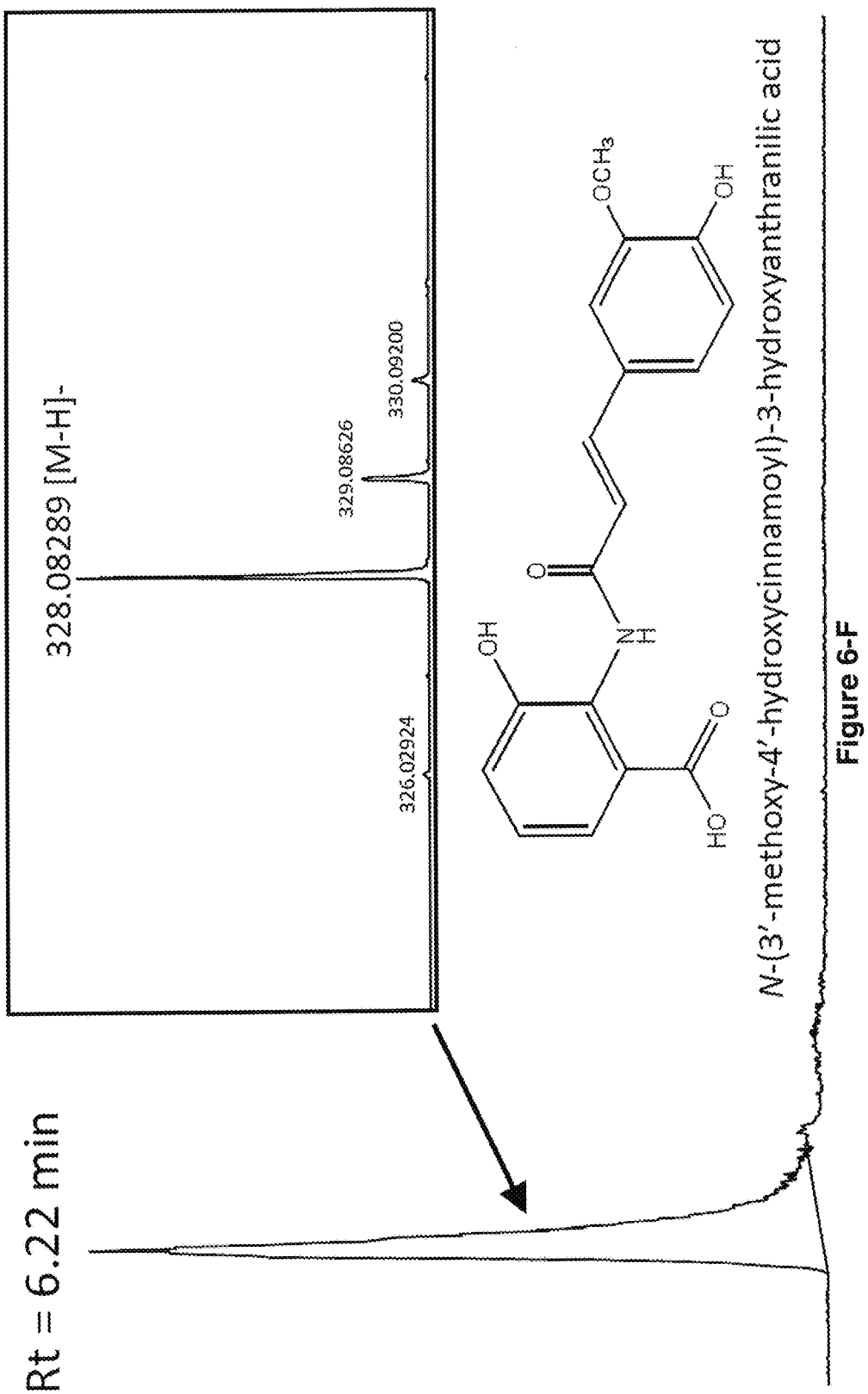
Figure 6-F
N-(3'-methoxy-4'-hydroxycinnamoyl)-3-hydroxyanthranilic acid

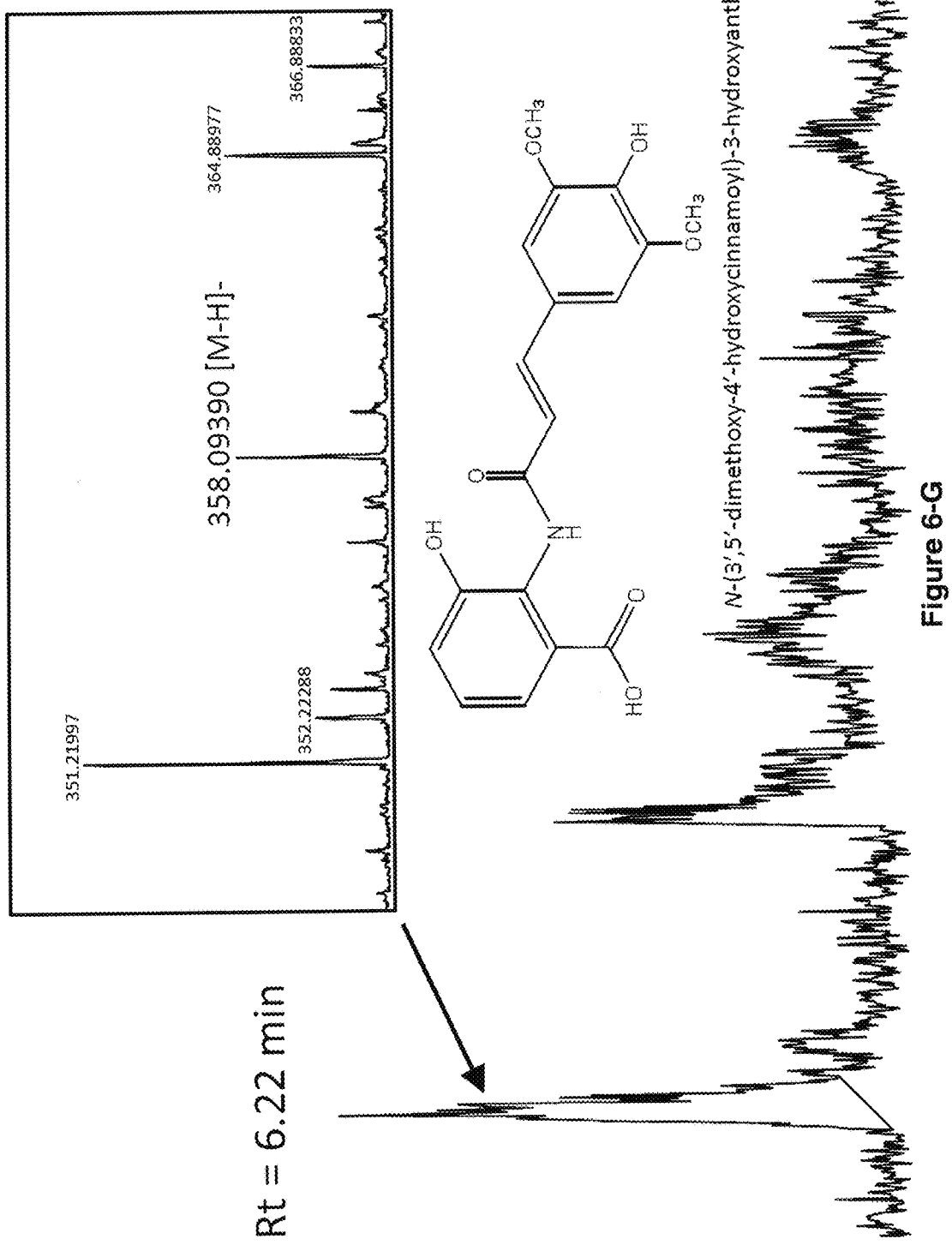
Figure 6-G

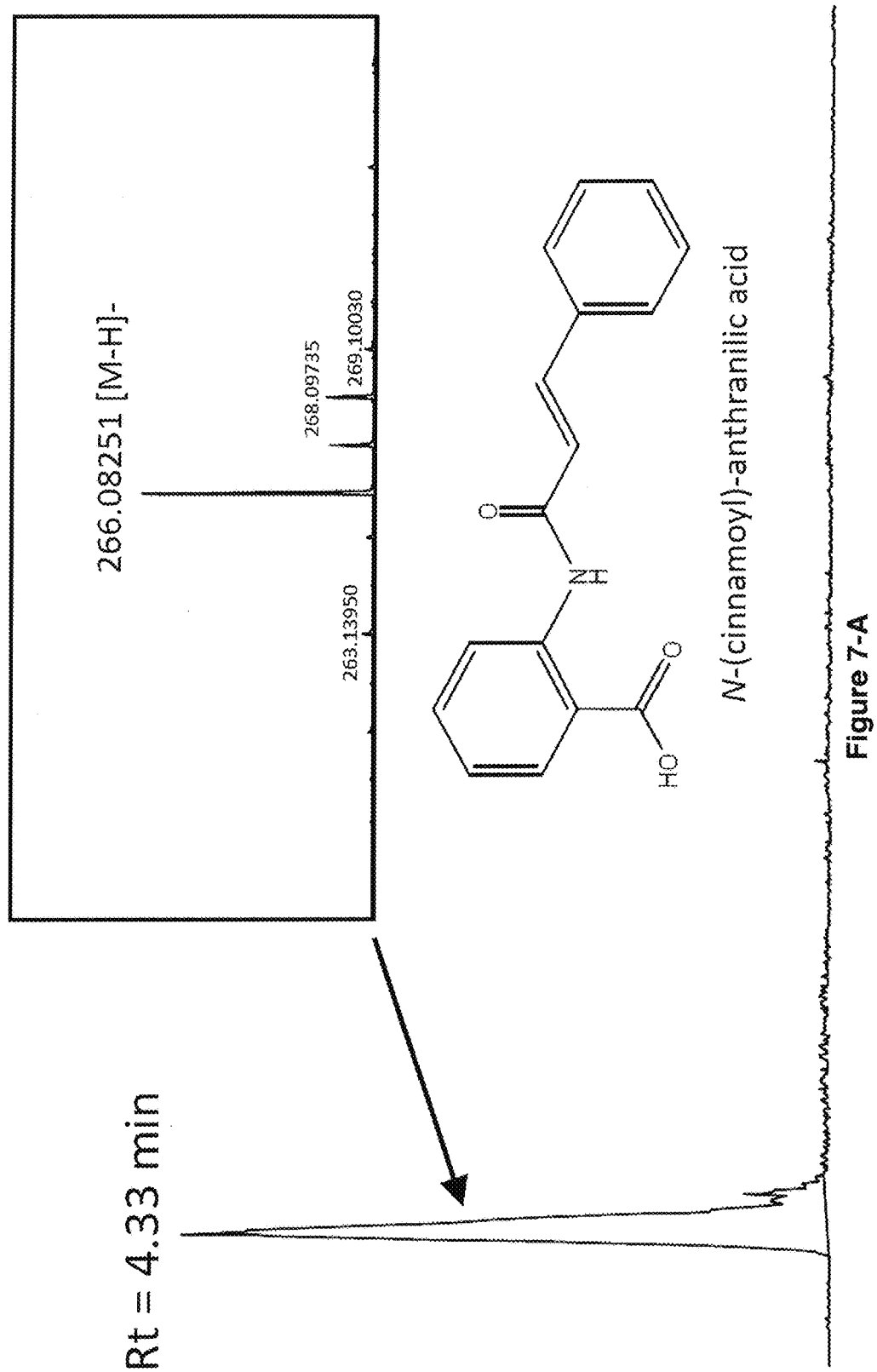
Figure 7-A

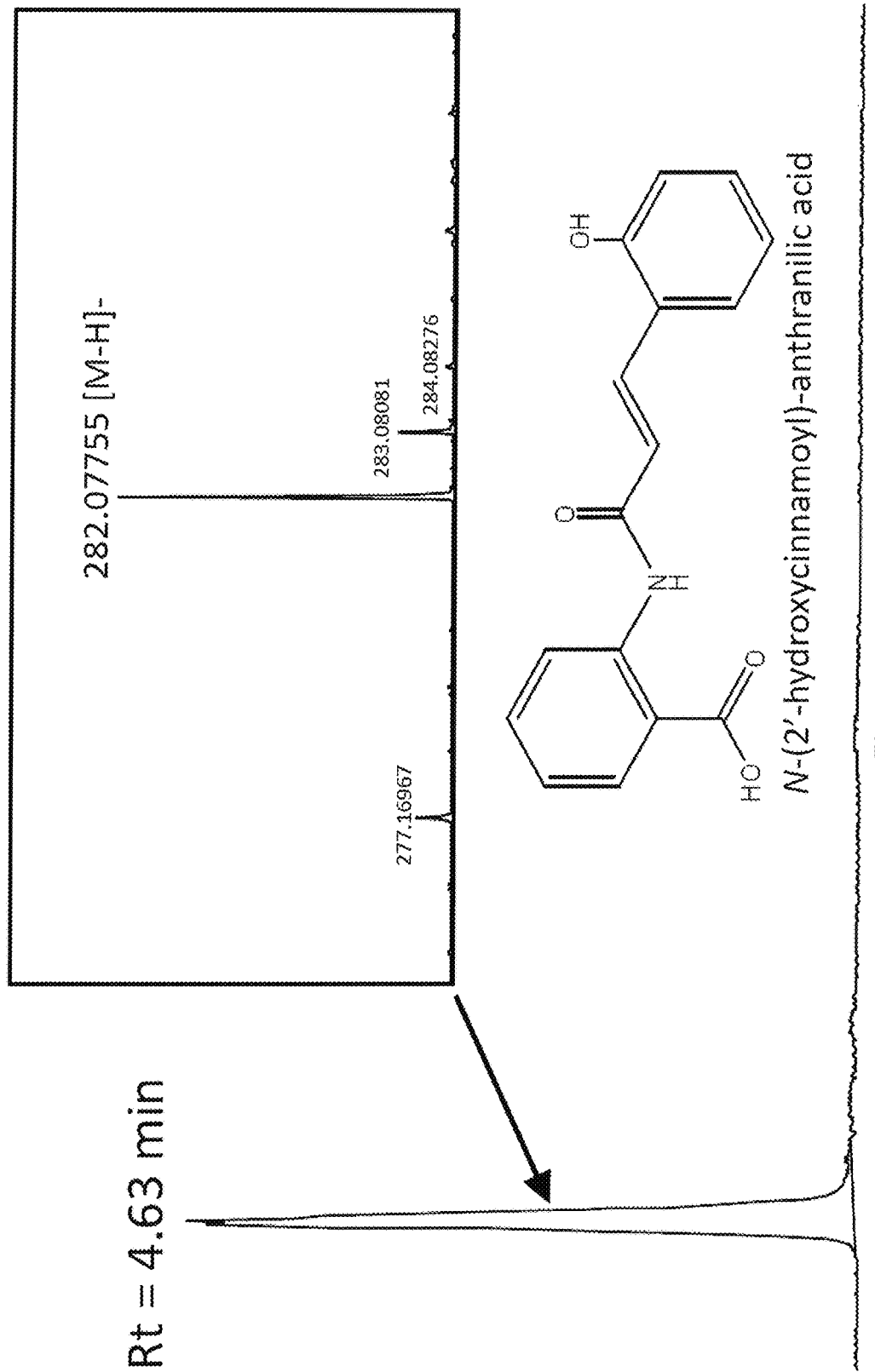
Figure 7-B

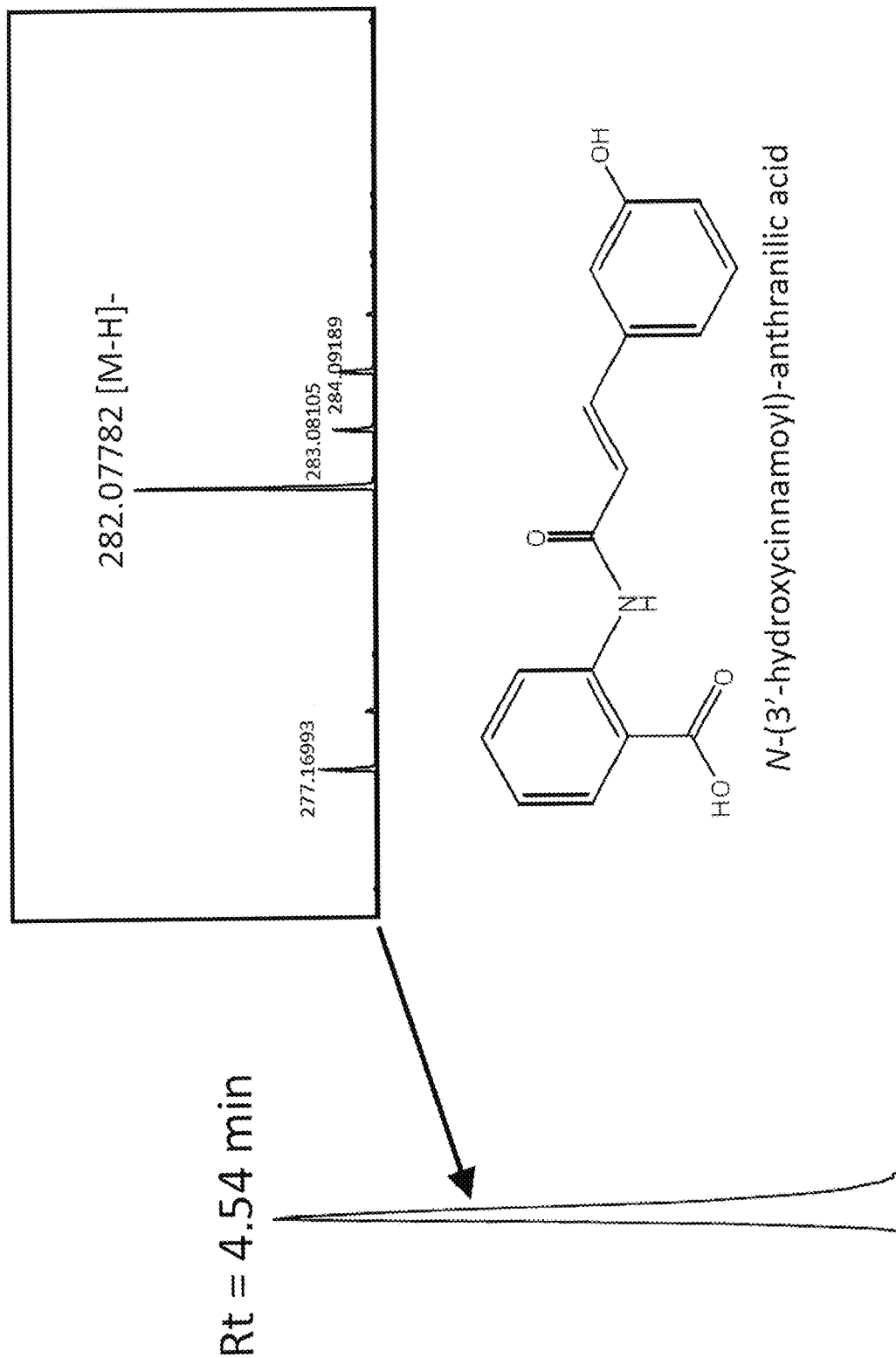
Figure 7-C

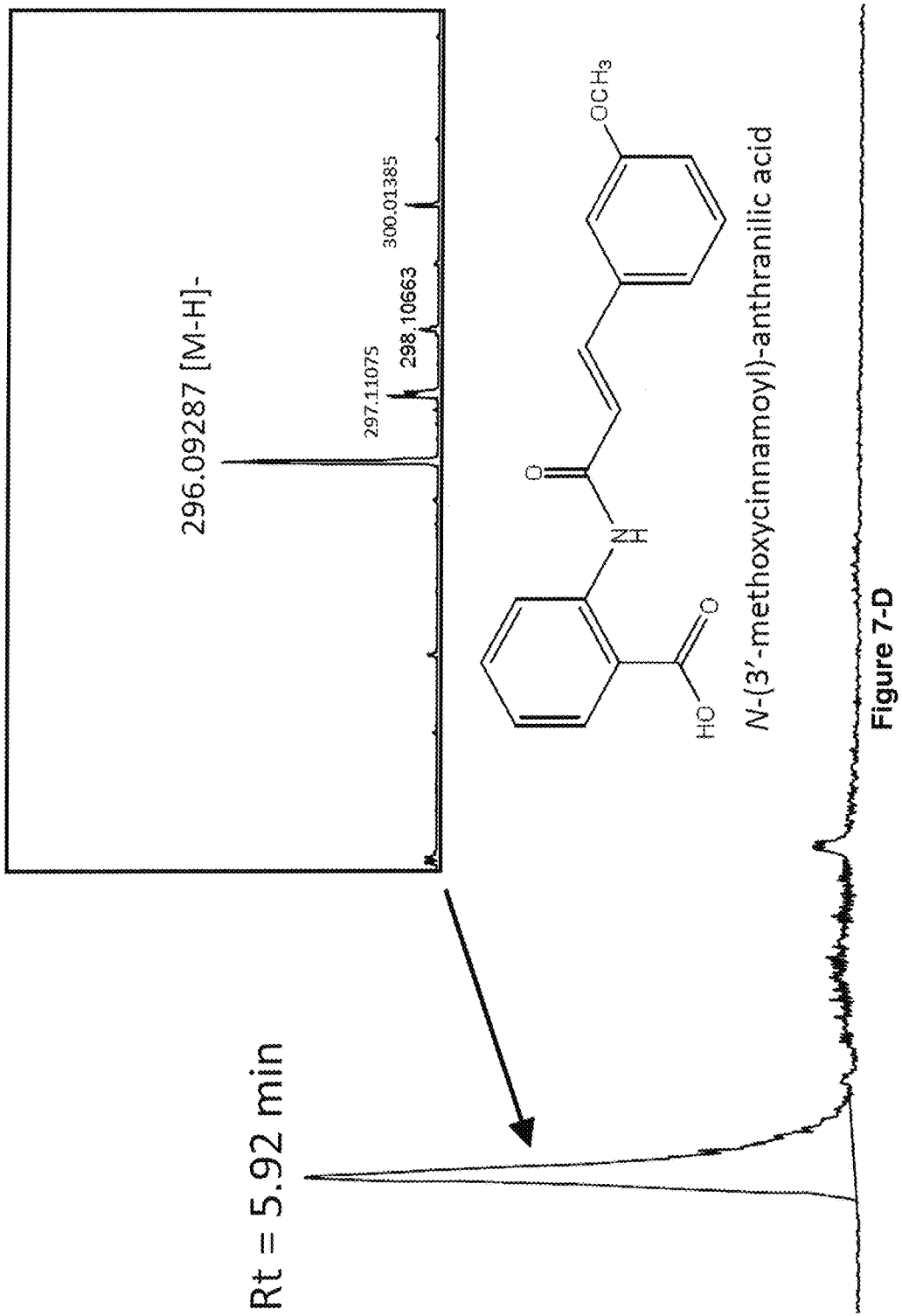
Figure 7-D

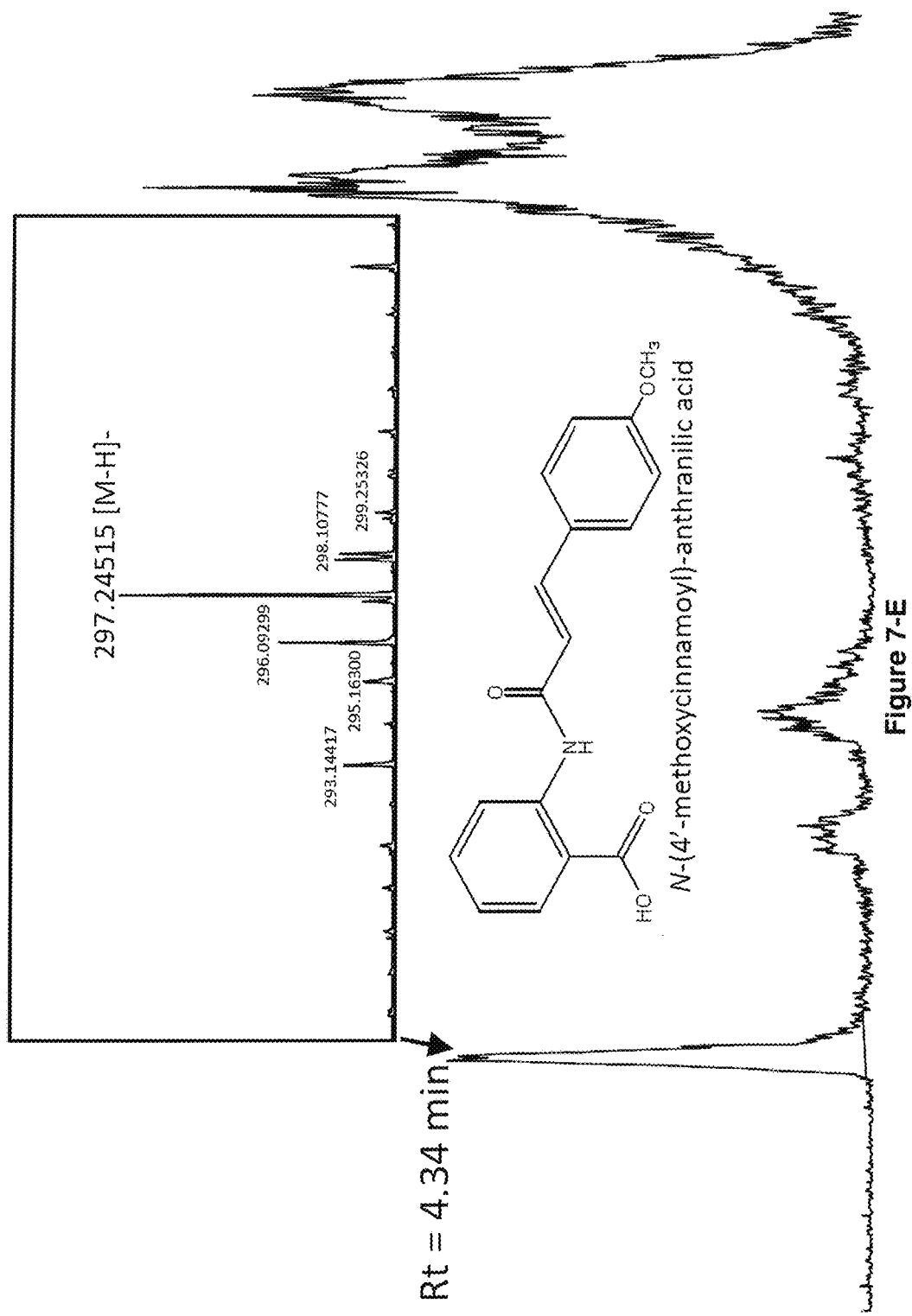
Figure 7-E

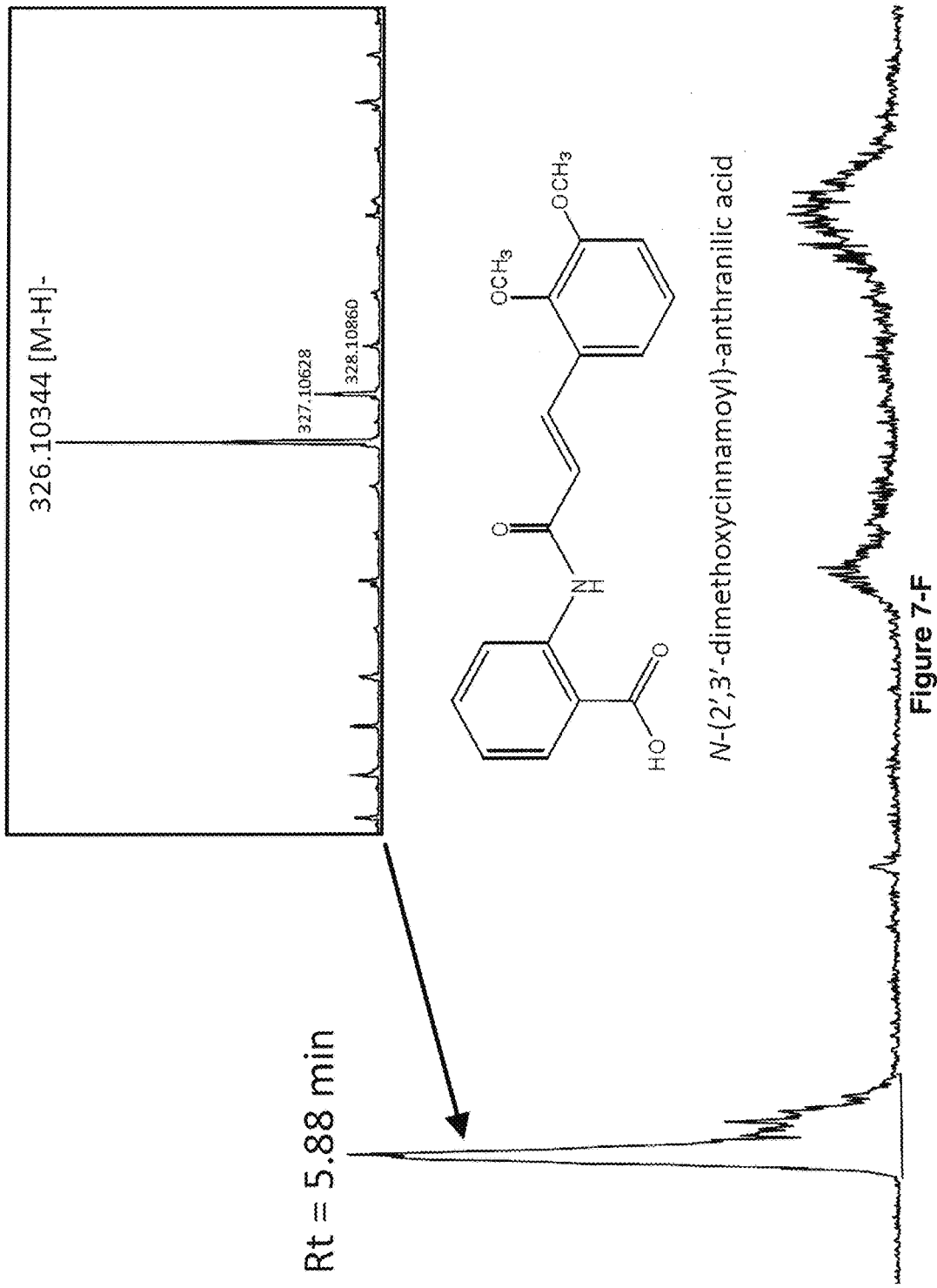
Figure 7-F

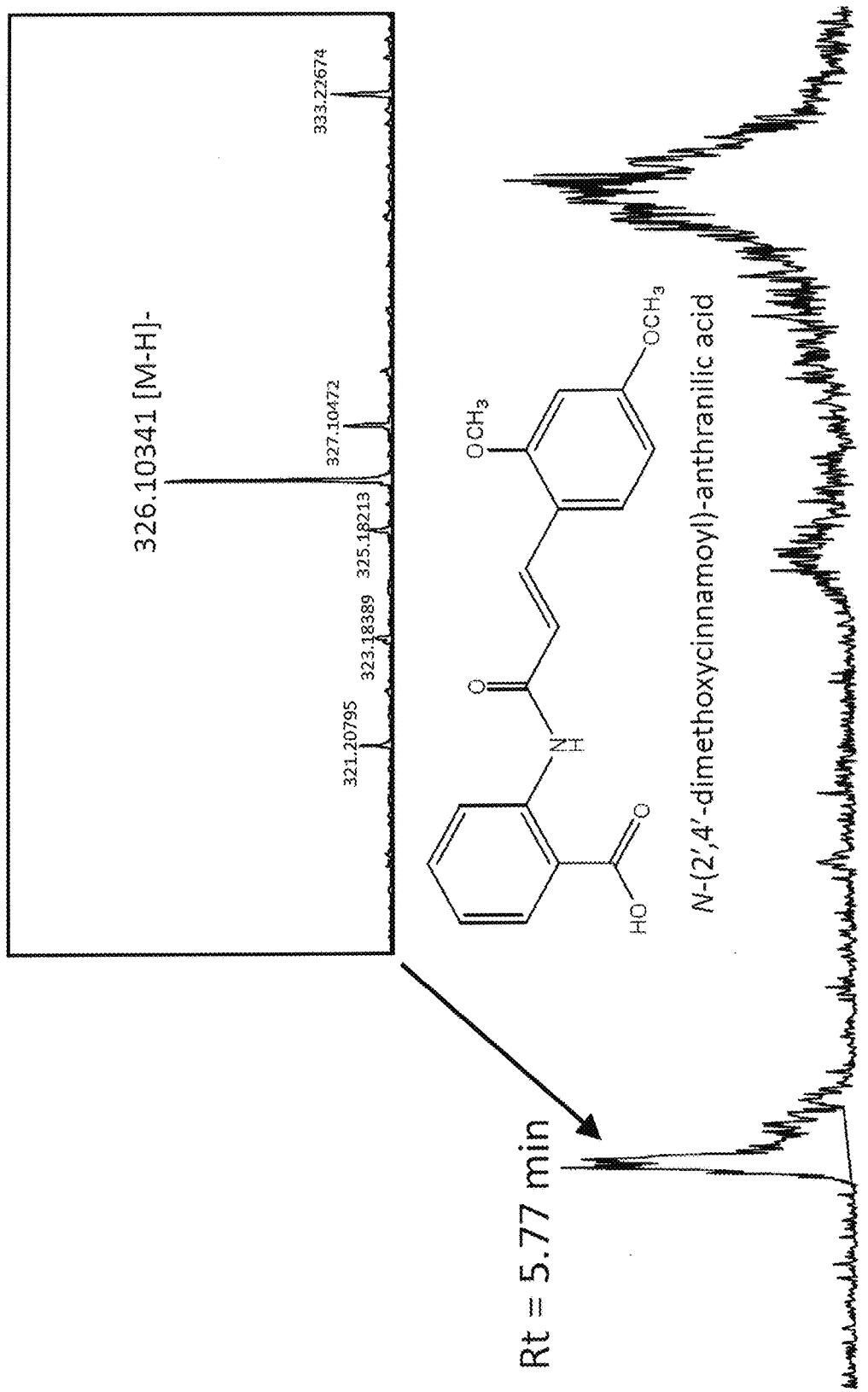
Figure 7-G

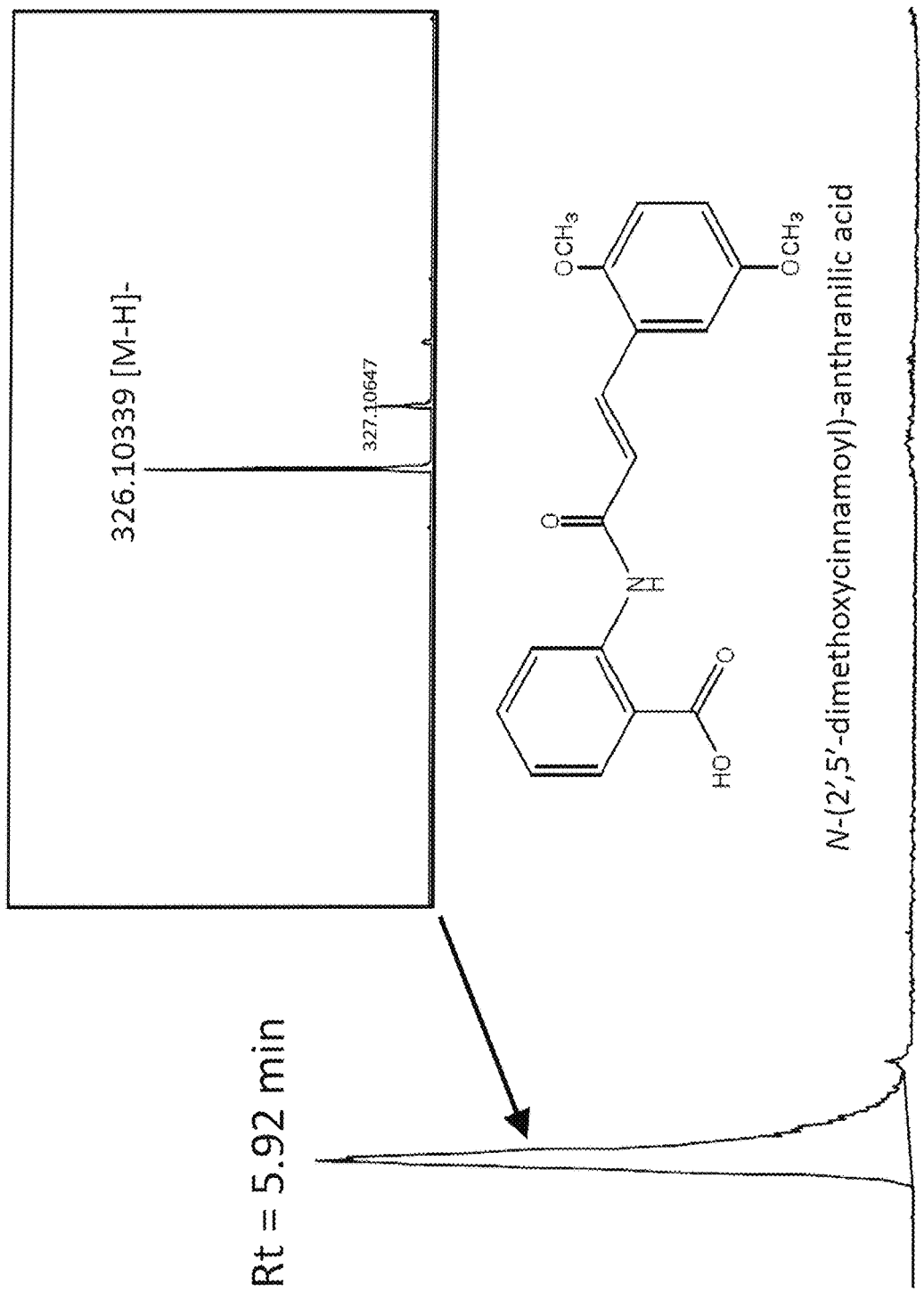
Figure 7-H

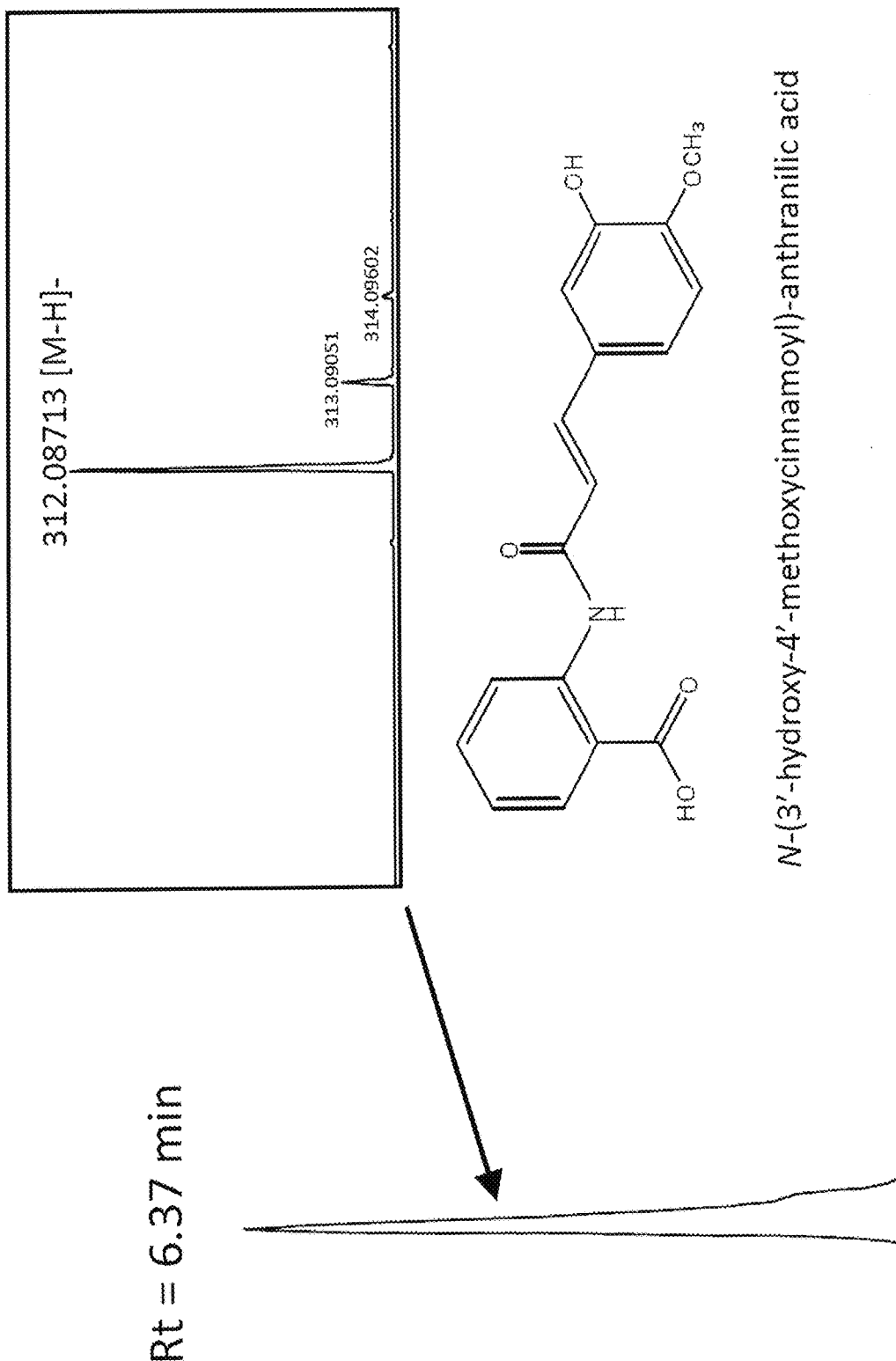
Figure 7-I

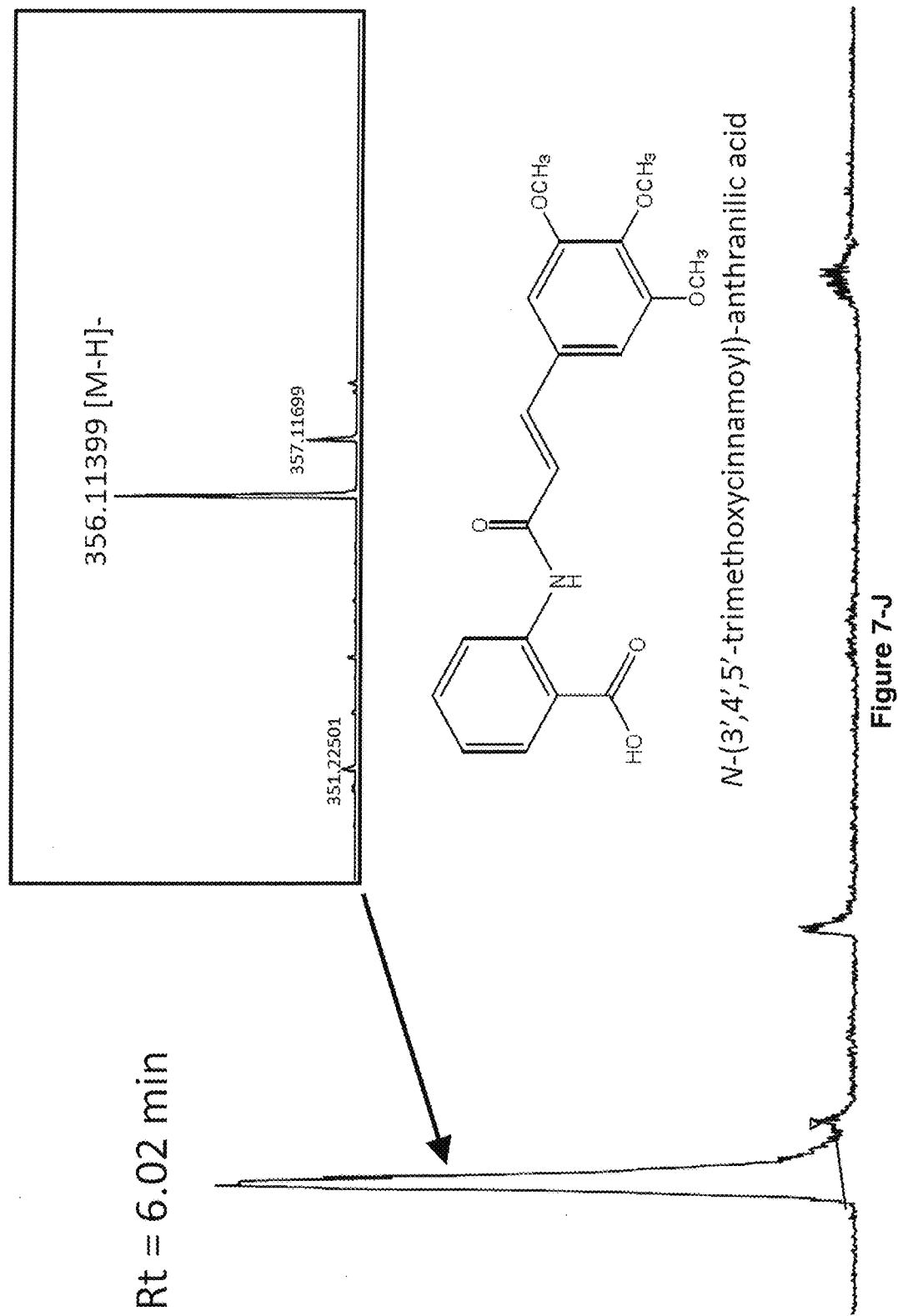
Figure 7-J

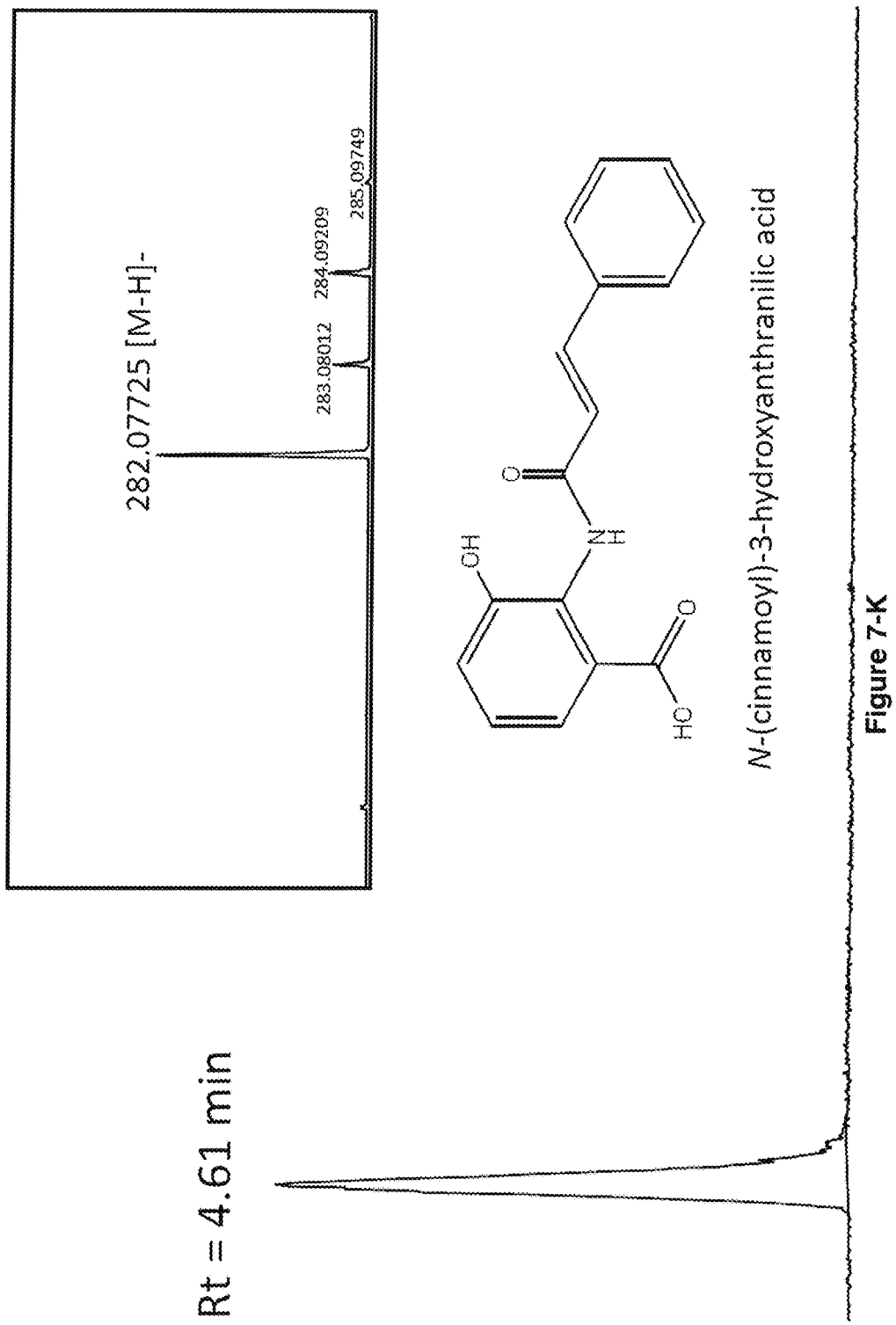
Figure 7-K

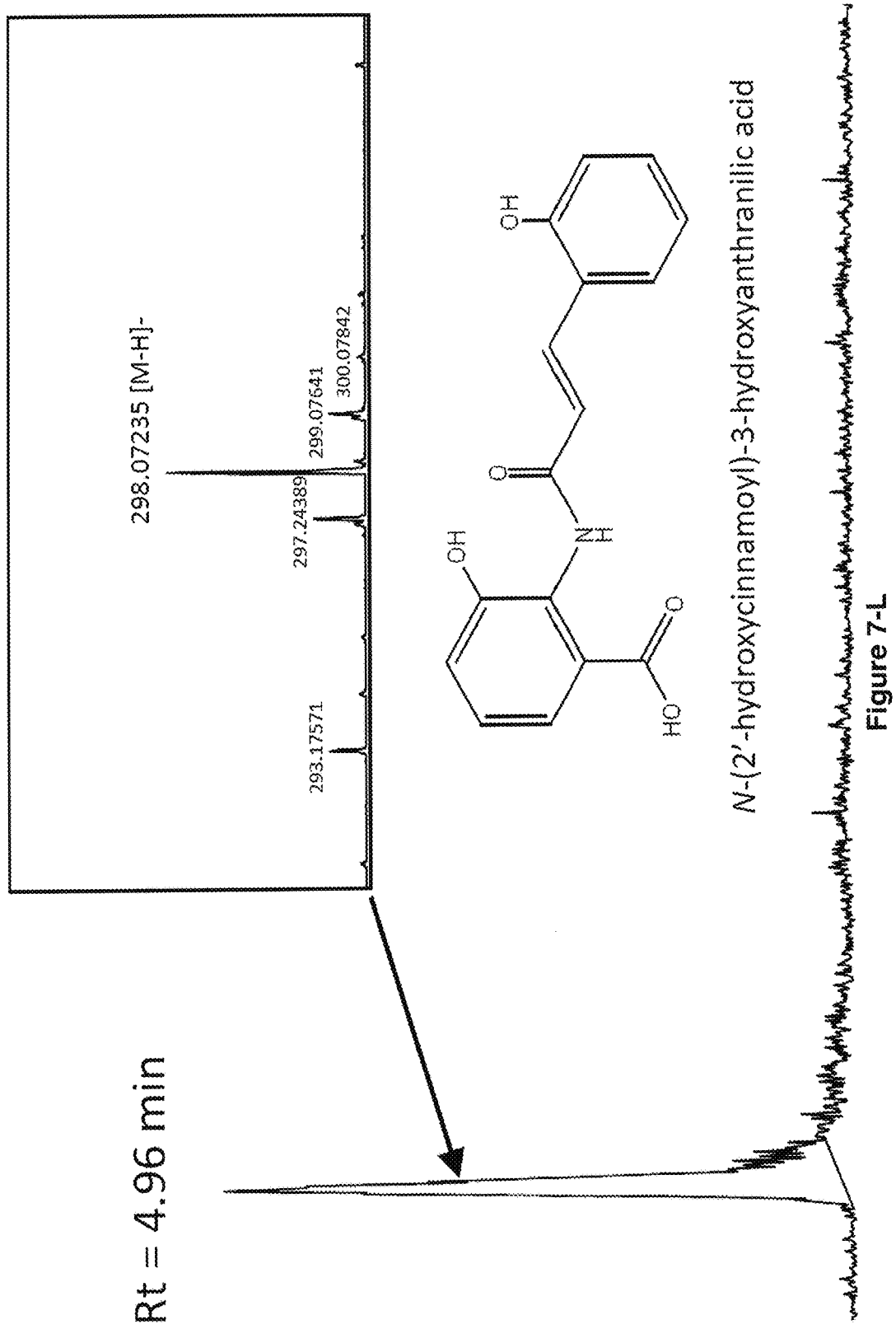
Figure 7-L

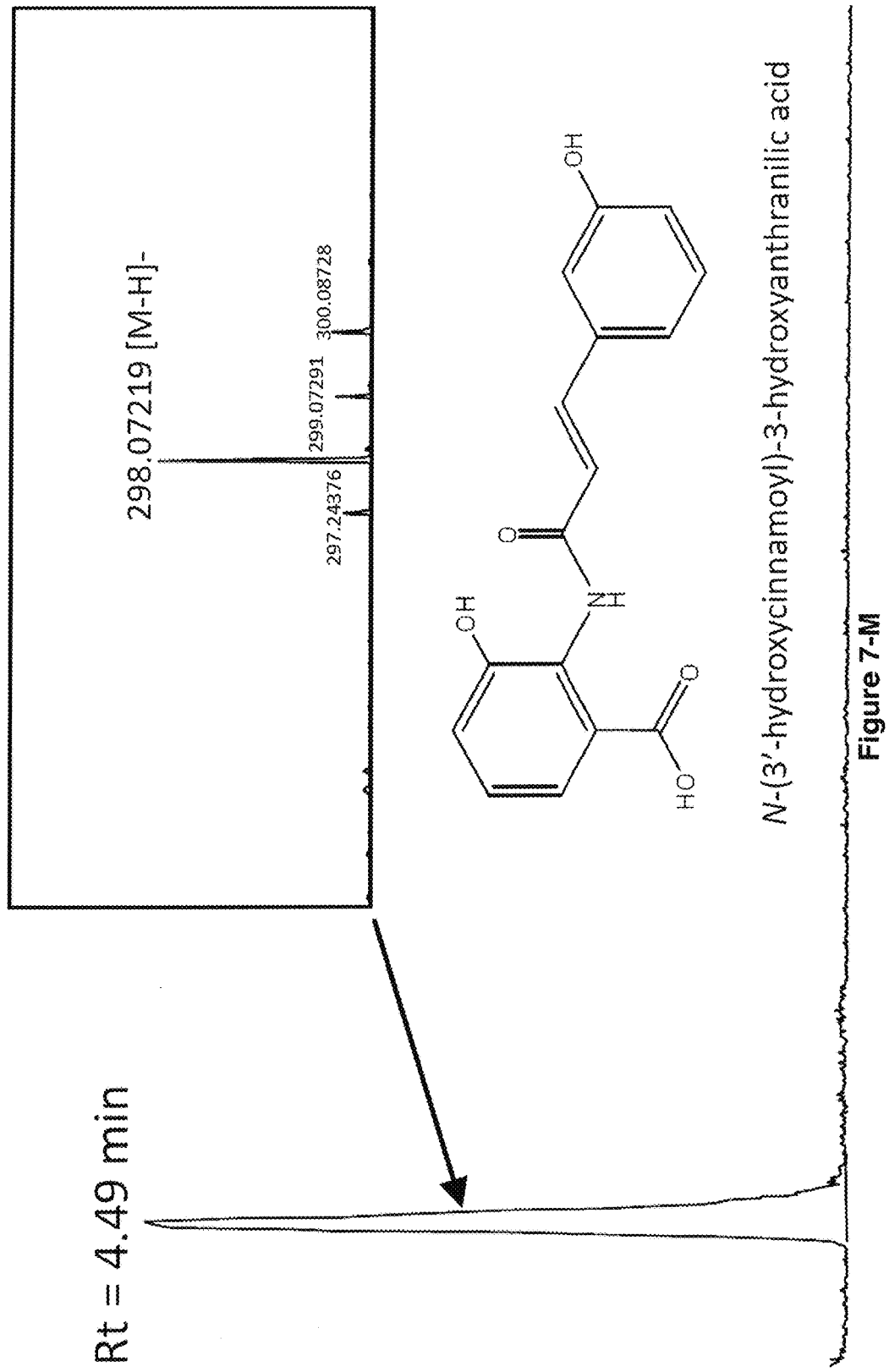
Figure 7-M

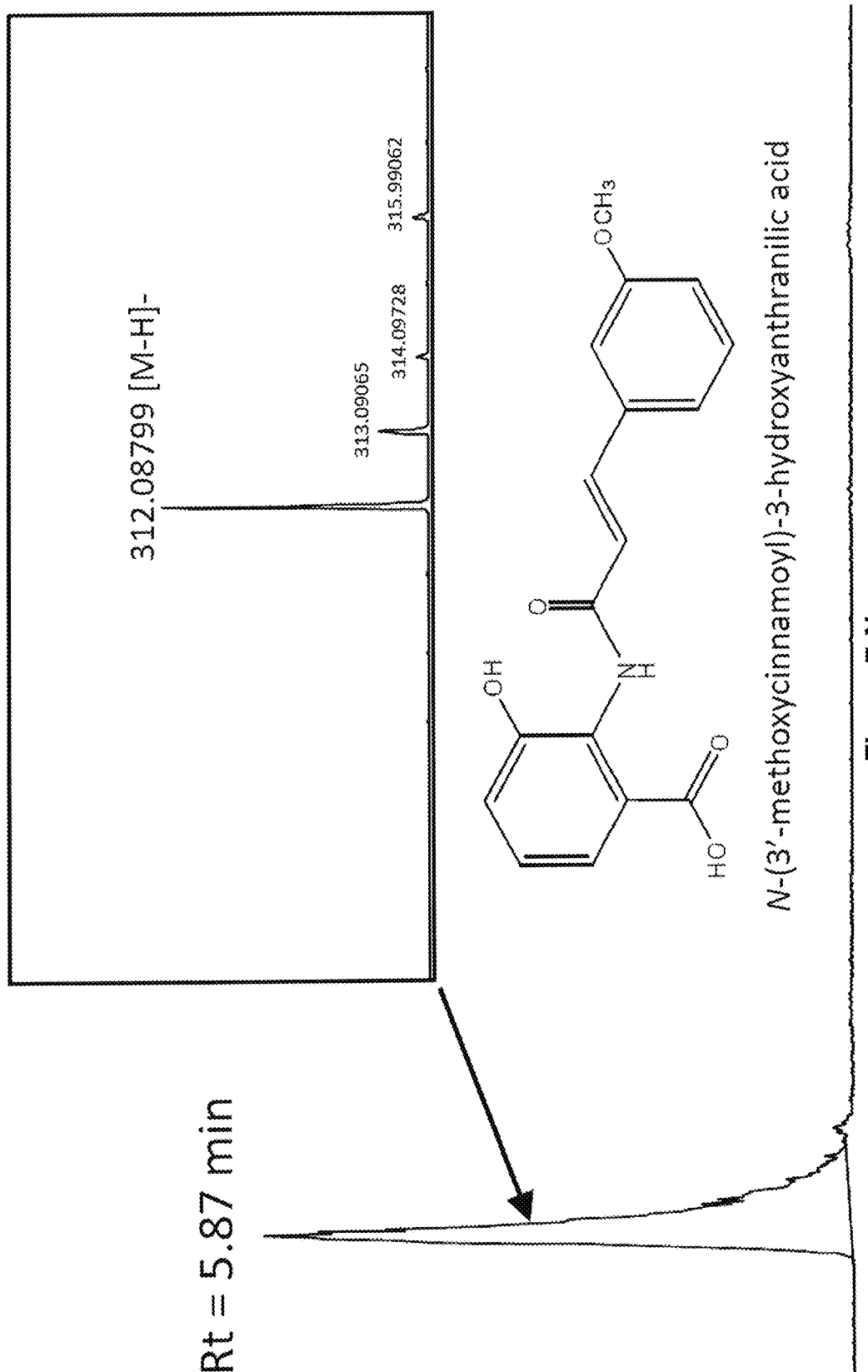
Figure 7-N

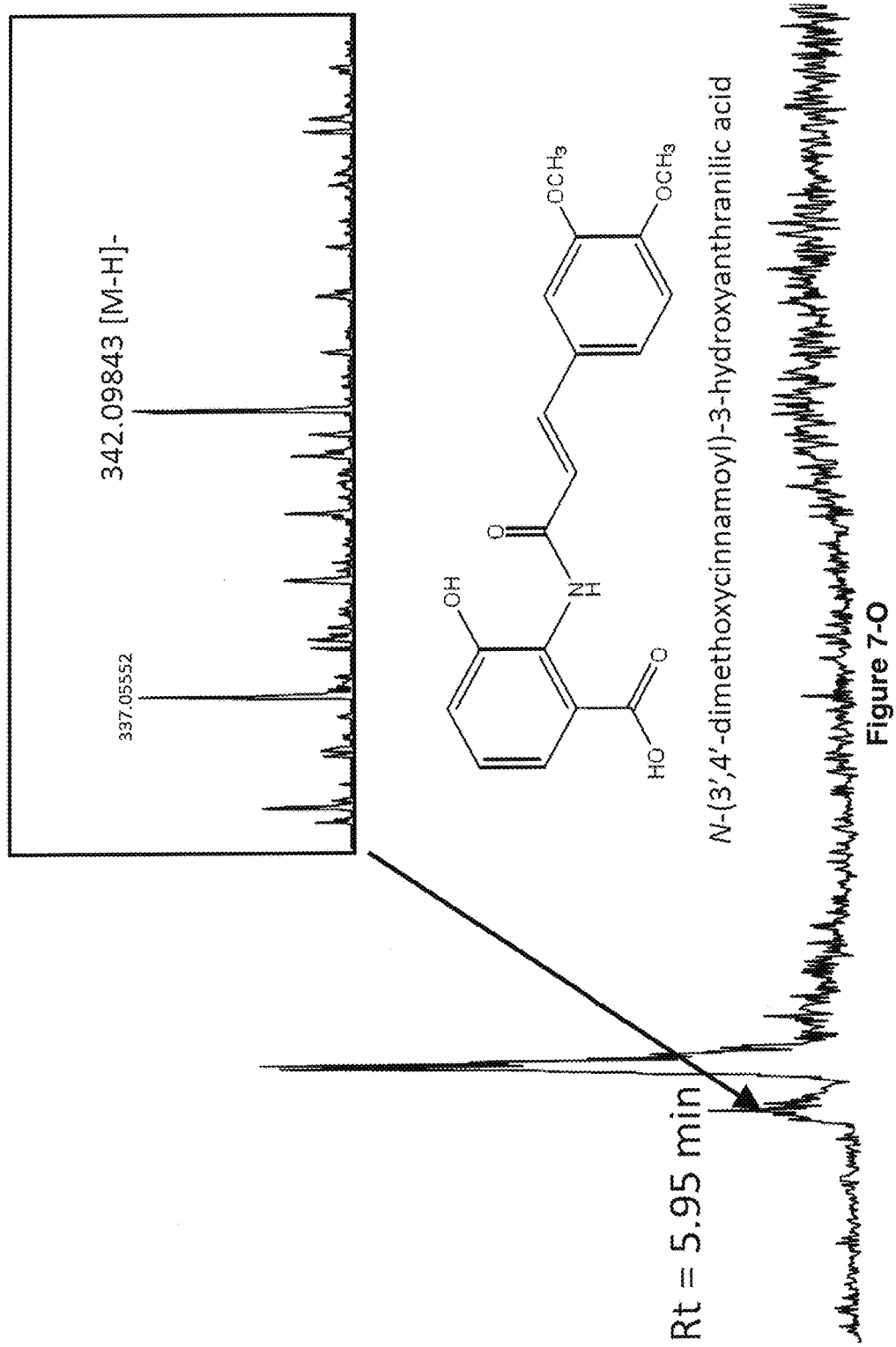
Figure 7-O

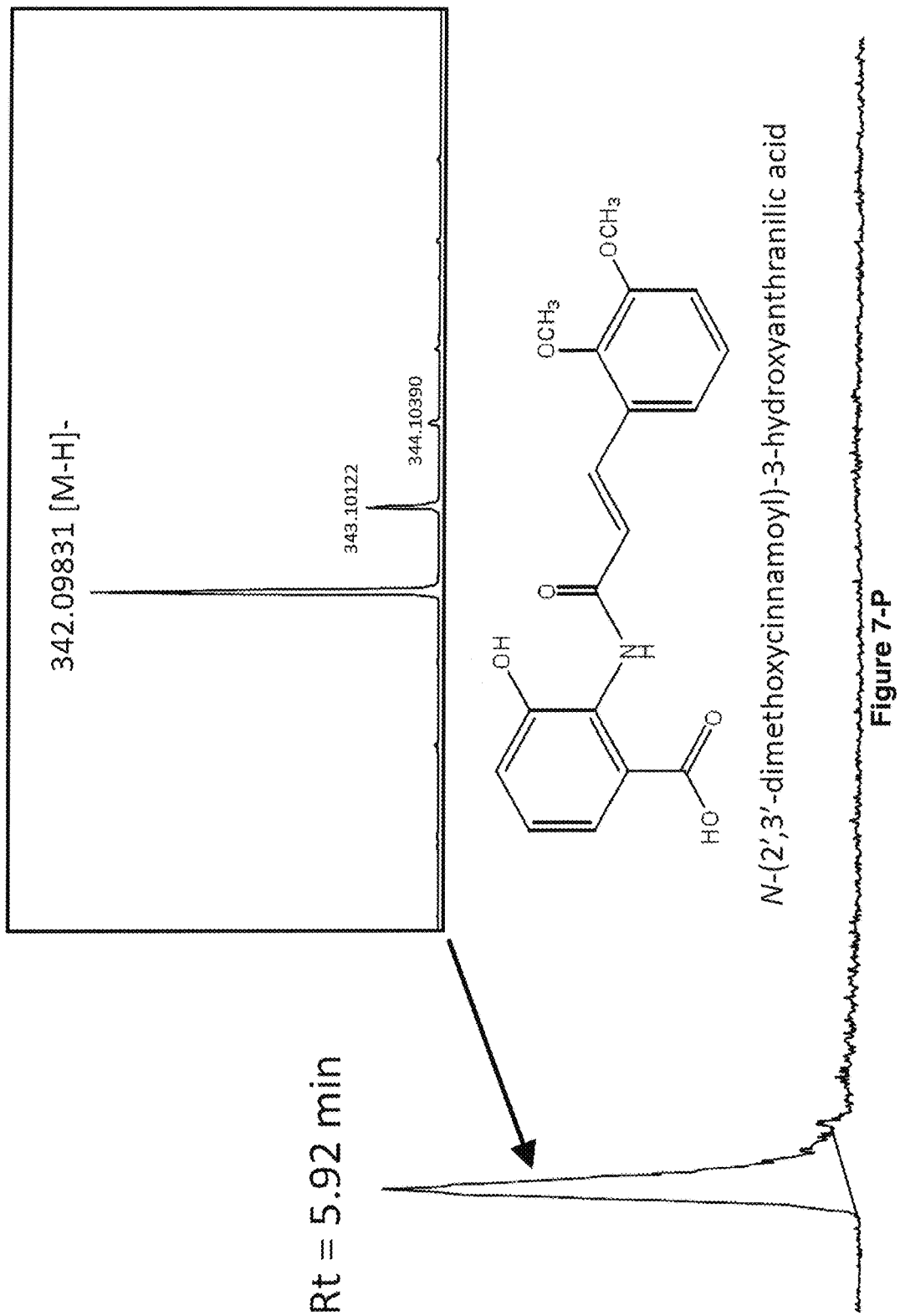
Figure 7-P

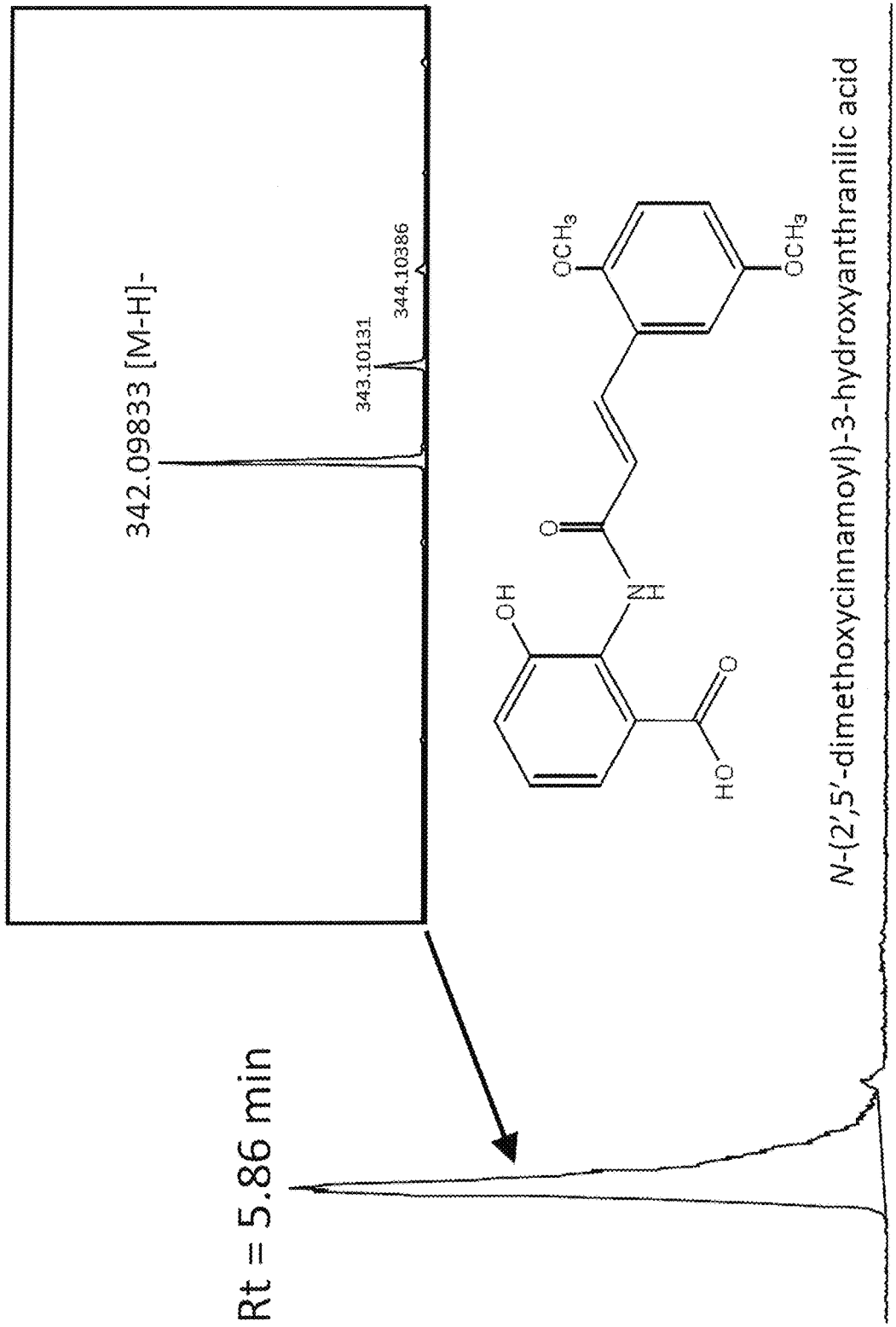
Figure 7-Q

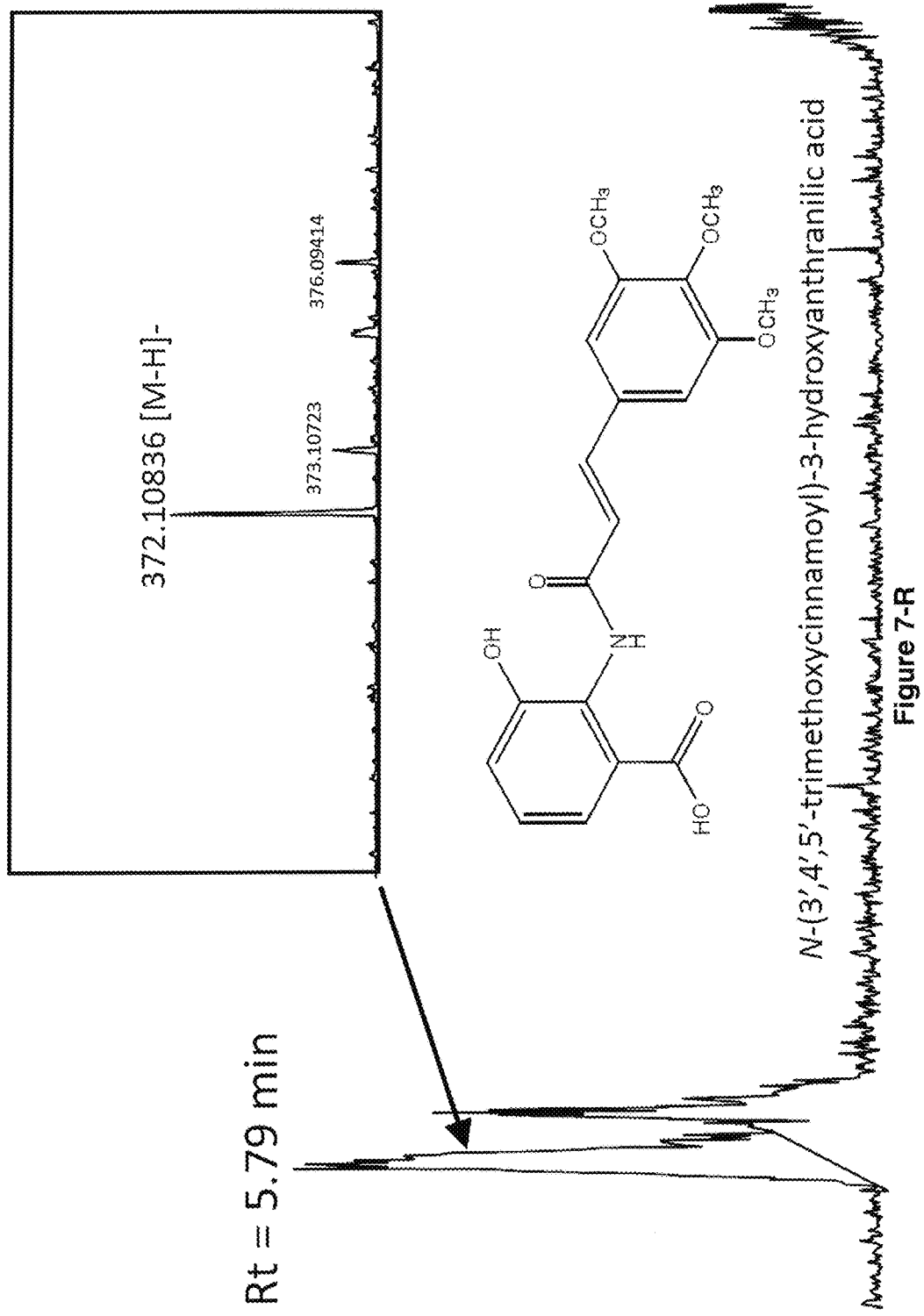
Figure 7-R

US 10,280,441 B2

HOST CELLS AND METHODS FOR PRODUCING CINNAMOYL ANTHRANILATE AND ANALOGS THEREOF

CROSS-REFERENCE TO RELATED APPLICATIONS

This application claims priority to U.S. Provisional Patent Application Ser. No. 61/393,843, filed Oct. 15, 2010, which is hereby incorporated by reference in its entirety.

STATEMENT OF GOVERNMENTAL SUPPORT

The invention was made with government support under Contract No. DE-AC02-05CH11231 awarded by the U.S. Department of Energy. The government has certain rights in the invention.

FIELD OF THE INVENTION

The present invention is in the field, of method of producing a cinnamoyl anthranilate, or analog thereof, in a genetically modified host cell.

BACKGROUND OF THE INVENTION

Biological synthesis of therapeutic drugs beneficial for human health using microbes offers an alternative production strategy to the methods that are commonly employed such as direct extraction from source organisms or chemical synthesis. In this study, we evaluated the potential for yeast (*Saccharomyces cerevisiae*) to be used as a catalyst for the synthesis of tranilast and various tranilast analogs (cinnamoyl anthranilates). Several studies have demonstrated that these phenolic amides have antioxidant properties and potential therapeutic benefits including anti-inflammatory, antiproliferative, and antigenotoxic effects. The few cinnamoyl anthranilates naturally produced in plants such as oats and carnations result from the coupling of various hydroxycinnamoyl-CoAs to anthranilic acid.

The worldwide drug market is large and is constantly expanding. Medical drugs used to treat human and animal diseases can be produced chemically or biologically. Even if the biological production is the preferred strategy, it is still rarely used due to the absence of known biosynthetic pathways, the toxicity of intermediate or final products, and poor yields or high recovery costs. Chemically produced drugs usually require large quantities of expensive and non-ecofriendly chemicals. For example, the drug tranilast (FIG. 1a), which belongs to the group of cinnamoyl anthranilate molecules, is manufactured only using organic synthesis methodologies. Tranilast and some of its analogs were recently shown to exhibit antioxidant, antigenotoxic, and antifibrotic activities (Fagerlund et al. 2009; Lee-Manion et al. 2009; Zammit et al. 2009). This synthetic drug (Rizaban, Kissei Pharmaceutical Co, Japan) is currently used in Japan and South Korea as an antihistamine to treat bronchial asthma, atopic dermatitis, allergic conjunctivitis, allergic rhinitis and other allergic disorders (Azuma et al. 1976; Okuda et al. 1984; Komatsu et al. 1988). Tranilast is also used to treat hypertrophic scars, scleroderma and other skin disease related to excessive fibrosis because it has the capacity to inhibit the release of chemical mediators from mast cells and macrophages, and suppresses collagen deposition (reviewed in Isaji et al. 1998). More recently, tranilast was shown to both inhibit and increase the expression of proinflammatory and anti-inflammatory cytokines, respectively, confirming its role in regulating mast cell and macrophage degranulation (Prud'homme 2007; Pae et al. 2008; Sun et al. 2010). Thus, health beneficial effects of tranilast have been assessed in vivo against the development of several disorders associated with pro-inflammatory leukocyte mediators, fibrogenesis and tumorigenesis including atherosclerosis, restenosis after angioplasty, arthritis, lacrimal gland chronic GVHD, inflammatory bowel disease, multiple sclerosis, adhesions, fibrosis, and tumor angiogenesis, growth and metastasis (Tamai et al. 2002; Platten et al. 2005; Oshitani et al. 2007; Chakrabarti et al. 2009; Cui et al. 2009; Guo et al. 2009; Ogawa et al. 2010; Shiota et al. 2010; Tan et al. 2010). Importantly, several years of clinical use have established that tranilast is well tolerated by most patients at doses of up to 600 mg/day for months (Konneh 1998).

Identification of new genes, biochemical characterization of enzymes, and the combination of enzymes to generate biological pathways are key elements of synthetic biology for the engineering of foreign hosts that are able to biologically synthesize naturally- and non-naturally-occurring drugs. Additionally, high-yield production is usually achieved when biosynthetic pathways are heterologously expressed in microbes that are suitable for fermentor production such as yeast *Saccharomyces cerevisiae* or *Escherichia coli*. The expression of plant metabolic pathways in microbial organisms is an attractive strategy for the production of valuable natural products that accumulate at low concentrations, are difficult to extract, or originate from endemic plant species (Horwitz 1994; Trantas et al. 2009). Microbial expression systems have several advantages over chemical synthesis or direct extraction from plant tissue, e.g. reduced requirements for toxic chemicals and natural resources, consistant quality, scalability, simple extraction and potential for higher synthesis efficiency (Chang and Keasling 2006). Advantages of *Saccharomyces cerevisiae* over other microbial hosts include its food-grade status, the extensive knowledge for large scale production, the availability of genetic tools, and its suitability to express plant genes such as cytochrome P450 enzymes (Trantas et al. 2009; Limem et al. 2008). Remarkable examples of pharmaceutical metabolites produced in recombinant yeast strains expressing plant genes include the precursor of the antimalarial drug artemisinic acid and taxadiene (Ro et al. 2006, Engels et al. 2006), flavonoids, stilbenoids and phenylpropanoids (Vannelli et al. 2007; Limem et al. 2008), vitamin C (Branduardi et al. 2007), hydrocortisone (Szczebara et al. 2003), and serotonin derivates (Park et al. 2008).

Natural cinnamoyl anthranilates are produced by the amide condensation of anthranilate and (hydroxy)-cinnamoyl-CoA derivatives, and most of them were co-purified from oats and carnation plants (Ponchet et al. 1988; Collins 1989).

SUMMARY OF THE INVENTION

The present invention provides for a system comprises an hydroxycinnamoyl/benzoyl-CoA:anthranilate N-hydroxycinnamoyl/benzoyltransferase (HCBT, EC 2.3.1.144), or functional fragment thereof, capable of catalyzing the formation of a cinnamoyl anthranilate, or analog thereof, from a cinnamoyl-CoA, or analog thereof, and an anthranilate, or analog thereof, and optionally a 4-coumarate:CoA ligase (4CL, EC 6.2.1.12), or functional fragment thereof, capable of catalyzing the formation of a cinnamic acid, or analog thereof, into a corresponding cinnamoyl-CoA thioester, or analog thereof. In some embodiments, the system is a genetically modified host cell comprising the HCBT, or functional fragment thereof, and optionally the 4CL, or functional fragment thereof. In some embodiments, the system is a genetically modified host cell comprising a first nucleic acid encoding the HCBT, or functional fragment thereof, and optionally a second nucleic aicd encoing the 4CL, or functional fragment thereof, wherein the first and second nucleic acid are the same or separate nucleic acids.

The present invention provides for a method of producing a cinnamoyl anthranilate, or analog thereof, in a genetically modified host cell. The method comprises culturing the genetically modified host cell under a suitable condition such that the culturing results in the genetically modified host cell producing an cinnamoyl anthranilate, or analog thereof, and optionally isolating the cinnamoyl anthranilate, or analog thereof, from the host cell and/or culture medium. The host cell comprises an hydroxycinnamoyUbenzoyl-CoA:anthranilate N-hydroxycinnamoyl/benzoyltransferase (HCBT, EC 2.3.1.144), or functional fragment thereof, capable of catalyzing the formation of a cinnamoyl anthranilate, or analog thereof, from a cinnamoyl-CoA, or analog thereof, and an anthranilate, or analog thereof, and optionally 4-coumarate:CoA ligase (4CL, EC 6.2.1.12), or functional fragment thereof, capable of catalyzing the formation of a cinnamic acid, or analog thereof, into a corresponding cinnamoyl-CoA thioester, or analog thereof. Optionally, when the cinnamic acid, or analog thereof, is a hydroxycinnamic acid, the host cell lacks any enzyme capable of catalyzing the decarboxylation of a hydroxycinnamic acid.

BRIEF DESCRIPTION OF THE DRAWINGS

The foregoing aspects and others will be readily appreciated by the skilled artisan from the following description of illustrative embodiments when read in conjunction with the accompanying drawings.

FIG. 1 shows the structure of tranilast and related cinnamoyl anthranilates. (A) Six structural analogs to tranilast that exhibit antioxidant, antifibrotic, antigenotoxic effects are shown (Lee-Manion et al. 2009; Zammit et al. 2009). (B) Schematic representation of the enzymatic reactions catalyzed by Arabidopsis 4-coumarate:coenzyme A ligase (4CL5) and hydroxycinnamoyl/benzoyl-CoA:anthranilate N-hydroxycinnamoyUbenzoyltransferase (HCBT) for the biosynthesis of various cinnamoyl anthranilates. For the biological production of cinnamoyl anthranilates analogous to tranilast, recombinant yeast expressing 4CL5 and HCBT was grown in the presence of anthranilate and known substrates for 4CL5 (p-coumaric, caffeic, ferulic, or sinapic acid).

FIG. 3 shows the detection of N-(4'-hydroxycinnamoyl)-anthranilate from the recombinant yeast culture medium. ESI-MS spectra were obtained after LC-TOF MS analysis of (A) the culture medium of recombinant yeast incubated with anthranilate and coumaric acid, and (B) an authentic N-(4'-hydroxycinnamoyl)-anthranilate solution.

FIG. 4 shows detection of tranilast in the recombinant yeast culture medium. ESI-MS spectra were obtained after LC-TOF MS analysis of (A) the culture medium of recombinant yeast incubated with anthranilate and 3,4-dimethoxycinnamic acid, and (B) an authentic tranilast solution.

Figure 2:
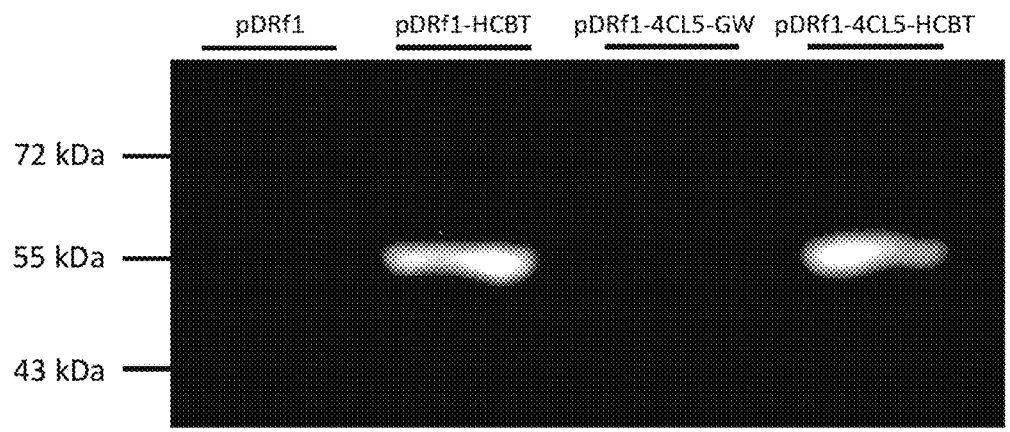
FIG. 2 shows the expression analysis of HCBT. Recombinant yeast cells grown to an $OD_{600}=1$ were harvested by centrifugation for protein extraction, and 5 µg of soluble protein were analyzed using immunobloting techniques. For protein extracts obtained from cells harboring the pDRfl-4CL5-HCBT or pDRfl-HCBT vectors, recombinant tagged HCBT was detected around 53 kDa using the universal antibody and according to the position of known markers. Protein extracts from yeast cells harboring the pDRfl-4CL5-GW or pDRfl empty vectors were also analyzed as negative controls.

p-Coumaric acid ($R_1=R_2=R_4=H$, $R_3=OH$)
o-Coumaric acid ($R_2=R_3=R_4=H$, $R_1=OH$)
m-Coumaric acid ($R_1=R_3=R_4=H$, $R_2=OH$)
Caffeic acid ($R_1=R_4=H$, $R_2=R_3=OH$).
Ferulic acid ($R_1=R_4=H$, $R_2=OCH_3$, $R_3=OH$)
Sinapic acid ($R_1=H$, $R_2=R_4=OCH_3$, $R_3=OH$)
Cinnamic acid ($R_1=R_2=R_3=R_4=H$)
3,4-Dimethoxycinnamic acid ($R_2=R_4=H$, $R_2=R_3=OCH_3$)
3,4,5-Trimethoxycinnamic acid ($R_1=H$, $R_2=R_3=R_4=OCH_3$)
4-Methoxycinnamic acid ($R_1=R_2=R_4=H$, $R_3=OCH_3$)
3-Hydroxy-4-methoxycinnamic acid ($R_1=R_4=H$, $R_2=OH$, $R_3=OCH_3$)
3-Methoxycinnamic acid ($R_1=R_3=R_4=H$, $R_2=OCH_3$)
2,3-Dimethoxycinnamic acid ($R_3=R_4=H$, $R_1=R_2=OCH_3$)
2,4-Dimethoxycinnamic acid ($R_2=R_4=H$, $R_1=R_3=OCH_3$)
2,5-Dimethoxycinnamic acid ($R_2=R_3=H$, $R_1=R_4=OCH_3$)
Compound B can be:
Anthranilate ($R_5=H$)
3-Hydroxyanthranilate ($R_5=OH$)
Compound C can be:
p-Coumaroyl-CoA ($R_1=R_2=R_4=H$, $R_3=OH$)
o-Coumaroyl-CoA ($R_2=R_3=R_4=H$, $R_1=OH$)
m-Coumaroyl-CoA ($R_1=R_3=R_4=H$, $R_2=OH$)
Caffeoyl-CoA ($R_1=R_4=H$, $R_2=R_3=OH$)
Feruloyl-CoA ($R_1$, $R_4=H$, $R_2=OCH_3$, $R_3=OH$)
Sinapoyl-CoA ($R_1=H$, $R_2=R_4=OCH_3$, $R_3=OH$)
Cinnamoyl-CoA ($R_1=R_2=R_3=R_4=H$)
3,4-Dirriethoxycinnamoyl-CoA ($R_1=R_4=H$, $R_2=R_3=OCH_3$)
3,4,5-Trimethoxycinnamoyl-CoA ($R_1=H$, $R_2=R_3=R_4=OCH_3$)
4-Methoxycinnamoyl-CoA ($R_1=R_2=R_4=H$, $R_3=OCH_3$)
3-Hydroxy-4-methoxycinnamoyl-CoA ($R_1=R_4=H$, $R_2=OH$, $R_3=OCH_3$)
3-Methoxycinnamoyl-CoA ($R_1=R_3=R_4=H$, $R_2=OCH_3$)
2,3-Dimethoxycinnamoyl-CoA ($R_3=R_4=H$, $R_1=R_2=OCH_3$)
2,4-Dimethoxycinnamoyl-CoA ($R_2=R_4=H$, $R_1=R_3=OCH_3$)
2,5-Dimethoxycinnamoyl-CoA ($R_2=R_3=H$, $R_1=R_4=OCH_3$)
Compound D can be:
N-(4'-Hydroxycinnamoyl)-anthranilic acid (Avn D) ($R_1=R_2=R_4=R_3=H$, $R_3=OH$)
N-(2'-Hydroxycinnamoyl)-anthranilic acid ($R_2=R_3=R_4=R_5=H$, $R_1=OH$)
N-(3'-Hydroxycinnamoyl)-anthranilic acid ($R_1=R_3=R_4=R_5=H$, $R_2=OH$)
N-(3',4'-Dihydroxycinnamoyl)-anthranilic acid (Avn E) ($R_1=R_4=R_5=H$, $R_2=R_3=OH$)
N-(3'-Methoxy-4'-hydroxycinnamoyl)-anthranilic acid (Avn F) ($R_1=R_4=R_5=H$, $R_2=OCH_3$, $R_3=OH$)
N-(3',5'-Dimethoxy-4'-hydroxycinnamoyl)-anthranilic acid ($R_1=R_5=H$, $R_2=R_4=OCH_3$, $R_3=OH$)

N-(Cinnamoyl)-anthranilic acid ($R_1=R_2=R_3=R_4=R_5=H$)
N-(3',4'-Dimethoxycinnamoy)-anthranilic acid (tranilast) ($R_1=R_4=R_5=H$, $R_2=R_3=OCH_3$)
N-(3',4',5'-Trimethoxycinnamoyl)-anthranilic acid ($R_1=R_5=H$, $R_2=R_3=R_4=OCH_3$)
N-(4'-Methoxycinnamoyl)-anthranilic acid ($R_1=R_2=R_4=R_5=OH$, $R_3=OCH_3$)
N-(3'-Hydroxy-4'-methoxycinnamoyl)-anthranilic acid ($R_1=R_4=R_5=H$, $R_2=OH$, $R_3=OCH_1$)
N-(3'-Methoxycinnamoyl)-anthranilic acid ($R_1=R_3=R_4=R_5=H$, $R_2=OCH_3$)
N-(2',3'-Dimethoxycinnamoyl)-anthranilic acid ($R_3=R_4=R_5=H$, $R_1=R_2=OCH_3$)
N-(2',4'-Dimethoxycinnamoyl)-anthranilic acid ($R_2=R_4=R_5=H$, $R_1=R_3=OCH_3$)
N-(2',5'-Dimethoxycinnamoyl)-anthranilic acid ($R_2=R_3=R_5=H$, $R_1=R_4=OCH_3$)
N-(4'-Hydroxycinnamoyl)-3-hydroxyanthranilic acid ($R_1=R_2=R_4=H$, $R_3=R_5=OH$)
N-(2'-Hydroxycinnamoyl)-3-hydroxyanthranilic acid ($R_2=R_3=R_4=H$, $R_1=R_5=OH$)
N-(3'-Hydroxycinnamoyl)-3-hydroxyanthranilic acid ($R_1=R_3=R_4=H$, $R_2=R_5=OH$)
N-(3',4'-Dihydroxycinnamoyl)-3-hydroxyanthranilic acid ($R_1=R_4=H$, $R_2=R_3=R_5=OH$)
N-(3'-Methoxy-4'-hydroxycinnamoyl)-3-hydroxyanthranilic acid ($R_1=R_4=H$, $R_2=OCH_3$, $R_3=R_5=OH$)
N-(3',5"-Dimethoxy-4'-hydroxycinnamoyl)-3-hydroxyanthranilic acid ($R_1=H$, $R_2=R_4=OCH_3$, $R_3=R_5=OH$)
N-(Cinnamoyl)-3-hydroxyanthranilic acid ($R_1=R_2=R_3=R_4=H$, $R_5=OH$)
N-(3',4'-Dimethoxycinnamoyl)-3-hydroxyanthranilic acid ($R_1=R_4=H$, $R_2=R_3=OCH_3$, $R_5=OH$)
N-(3',4',5'-Trimethoxycinnamoyl)-3-hydroxyanthranilic acid ($R_1=H$, $R_2=R_3=R_4=OCH_3$, $R_5=OH$)
N-(3'-Methoxycinnamoyl)-3-hydroxyanthranillc acid ($R_1=R_3=R_4=H$, $R_2=OCH_3$, $R_5=OH$)
N-(2',3'-Dimethoxycinnamoyl)-3-hydroxyanthranilic acid ($R_3=R_4=H$, $R_1=R_2=OCH_3$, $R_5=OH$)
N-(2',5'-Dimethoxycinnamoyl)-3-hydroxyanthranilic acid ($R_2=R_3=H$, $R_1=R_4=OCH_3$)

FIG. 6 shows the detection of seven N-(hydroxycinnamoyl)-anthranilates from the recombinant yeast culture medium. ESI-MS spectra were obtained after LC-TOF MS analysis of the yeast culture medium supplemented with (A) anthranilate and caffeic acid, (B) anthranilate and ferulic acid, (C) anthranilate and sinapic acid, (D) 3-hydroxyanthranilate and p-coumaric acid, (E) 3-hydroxyanthranilate and caffeic acid, (F) 3-hydroxyanthranilate and ferulic acid, and (G) 3-hydroxyanthranilate and sinapic acid.

FIG. 7 shows the detection of eighteen cinnamoyl anthranilates from the recombinant yeast culture medium. ESI-MS spectra were obtained after LC-TOF MS analysis of the yeast culture medium supplemented with (A) anthranilate and cinnamic acid, (B) anthranilate and o-coumaric acid, (C) anthranilate and m-coumaric acid, (D) anthranilate and 3-methoxycinnamic acid, (E) anthranilate and 4-methoxycinnamic acid, (F) anthranilate and 2,3-dimethoxycinnamic acid, (G) anthranilate and 2,4-dimethoxycinnamic acid, (H) anthranilate and 2,5-dimethoxycinnamic acid, (I) anthranilate and isoferulic acid, (J) anthranilate and 3,4,5-trimethoxycinnamic acid, (K) 3-hydroxyanthranilate and cinnamic acid, (L) 3-hydroxyanthranilate and o-coumaric acid, (M) 3-hydroxyanthranilate and m-coumaric acid, (N) 3-hydroxyanthranilate and 3-methoxycinnamic acid, (O) 3-hydroxyanthranilate and 3,4-dimethoxycinnamic acid, (P) 3-hydroxyanthranilate and 2,3-dimethoxycinnamic acid, (Q) 3-hydroxyanthranilate and 2,5-dimethoxycinnamic acid, (R) 3-hydroxyanthranilate and 3,4,5-trimethoxycinnamic acid.

DETAILED DESCRIPTION OF THE INVENTION

Before the invention is described in detail, it is to be understood that, unless otherwise indicated, this invention is not limited to particular sequences, expression vectors, enzymes, host microorganisms, or processes, as such may vary. It is also to be understood that the terminology used herein is for purposes of describing particular embodiments only, and is not intended to be limiting.

As used in the specification and the appended claims, the singular forms "a," "an," and "the" include plural referents unless the context clearly dictates otherwise. Thus, for example, reference to an "expression vector" includes a single expression vector as well as a plurality of expression vectors, either the same (e.g., the same operon) or different; reference to "cell" includes a single cell as well as a plurality of cells; and the like.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

The terms "host cell" and "host microorganism" are used interchangeably herein to refer to a living biological cell that can be transformed via insertion of an expression vector. Thus, a host organism or cell as described herein may be a prokaryotic organism (e.g., an organism of the kingdom Eubacteria) or a eukaryotic cell. As will be appreciated by one of ordinary skill in the art, a prokaryotic cell lacks a membrane-bound nucleus, while a eukaryotic cell has a membrane-bound nucleus.

The term "heterologous DNA" as used herein refers to a polymer of nucleic acids wherein at least one of the following is true: (a) the sequence of nucleic acids is foreign to (i.e., not naturally found in) a given host microorganism; (b) the sequence may be naturally found in a given host microorganism, but in an unnatural (e.g., greater than expected) amount; or (c) the sequence of nucleic acids comprises two or more subsequences that are not found in the same relationship to each other in nature. For example, regarding instance (c), a heterologous nucleic acid sequence that is recombinantly produced will have two or more sequences from unrelated genes arranged to make a new functional nucleic acid. Specifically, the present invention describes the introduction of an expression vector into a host microorganism, wherein the expression vector contains a nucleic acid sequence coding for an enzyme that is not normally found in a host microorganism. With reference to the host microorganism's genome, then, the nucleic acid sequence that codes for the enzyme is heterologous.

The terms "expression vector" or "vector" refer to a compound and/or composition that transduces, transforms, or infects a host microorganism, thereby causing the cell to express nucleic acids and/or proteins other than those native to the cell, or in a manner not native to the cell. An "expression vector" contains a sequence of nucleic acids (ordinarily RNA or DNA) to be expressed by the host microorganism. Optionally, the expression vector also comprises materials to aid in achieving entry of the nucleic acid into the host microorganism, such as a virus, liposome, protein coating, or the like. The expression vectors contemplated for use in the present invention include those into which a nucleic acid sequence can be inserted, along with any preferred or required operational elements. Further, the expression vector must be one that can be transferred into a host microorganism and replicated therein. Preferred expression vectors are plasmids, particularly those with restriction sites that have been well documented and that contain the operational elements preferred or required for transcription of the nucleic acid sequence. Such plasmids, as well as other expression vectors, are well known to those of ordinary skill in the art.

The term "transduce" as used herein refers to the transfer of a sequence of nucleic acids into a host microorganism or cell. Only when the sequence of nucleic acids becomes stably replicated by the cell does the host microorganism or cell become "transformed." As will be appreciated by those of ordinary skill in the art, "transformation" may take place either by incorporation of the sequence of nucleic acids into the cellular genome, i.e., chromosomal integration, or by extrachromosomal integration. In contrast, an expression vector, e.g., a virus, is "infective" when it transduces a host microorganism, replicates, and (without the benefit of any complementary virus or vector) spreads progeny expression vectors, e.g., viruses, of the same type as the original transducing expression vector to other microorganisms, wherein the progeny expression vectors possess the same ability to reproduce.

The terms "isolated" or "biologically pure" refer to material that is substantially or essentially free of components that normally accompany it in its native state or free of components from a host cell or culture medium from which the material is obtained.

As used herein, the terms "nucleic acid sequence," "sequence of nucleic acids," and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing normucleotidic backbones, provided that the polymers contain nucleobases in a configuration that allows for base pairing and base stacking, as found in DNA and RNA. Thus, these terms include known types of nucleic acid sequence modifications, for example, substitution of one or more of the naturally occurring nucleotides with an analog; internucleotide modifications, such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkylphosphoramidates, aminoalkylphosphotriesters); those containing pendant moieties, such as, for example, proteins (including nucleases, toxins, antibodies, signal peptides, poly-L-lysine, etc.); those with intercalators (e.g., acridine, psoralen, etc.); and those containing chelators (e.g., metals, radioactive metals, boron, oxidative metals, etc.). As used herein, the symbols for nucleotides and polynucleotides are those recommended by the IUPAC-IUB Commission of Biochemical Nomenclature (*Biochem.* 9:4022, 1970).

The term "operably linked" refers to a functional linkage between a nucleic acid expression control sequence (such as a promoter) and a second nucleic acid sequence, wherein the expression control sequence directs transcription of the nucleic acid corresponding to the second sequence.

The term "functional fragment" refers to an enzyme that has an amino acid sequence that is at least 70%, 75%, 80%, 85%, 90%, 95% or 99% identical to the amino acid sequence of any one of the enzymes described in this specification or in an incorporated reference. The functional fragment retains amino acids residues that are recognized as conserved for the enzyme. The functional fragment may have non-conserved amino acid residues replaced or found to be of a different amino acid, or amino acid(s) inserted or deleted, but which does not affect or has insignificant effect on the enzymatic activity of the functional fragment. The functional fragment has an enzymatic activity that is identical or essentially identical to the enzymatic activity any one of the enzymes described in this specification or in an incorporated reference. The functional fragment may be found in nature or be an engineered mutant thereof. The mutant may have one or more amino acids substituted, deleted or inserted, or a combination thereof, as compared to the enzyme described in this specification or in an incorporated reference.

The present invention provides for a method of producing a cinnamoyl anthranilate, or analog thereof, in a genetically modified host cell. The method comprises culturing the genetically modified host cell under a suitable condition such that the culturing results in the genetically modified host cell producing an cinnamoyl anthranilate, or analog thereof, and optionally isolating the cinnamoyl anthranilate, or analog thereof, from the host cell and/or culture medium. The host cell comprises an hydroxycinnamoyl/benzoyl-CoA:anthranilate N-hydroxycinnamoyl/benzoyltransferase (HCBT, EC 2.3.1.144), or functional fragment thereof, capable of catalyzing the formation of a cinnamoyl anthranilate, or analog thereof, from a cinnamoyl-CoA, or analog thereof, and an anthranilate, or analog thereof, and optionally 4-coumarate:CoA ligase (4CL, EC 6.2.1.12), or functional fragment thereof, capable of catalyzing the formation of a cinnamic acid, or analog thereof, into a corresponding cinnamoyl-CoA thioester, or analog thereof. Optionally, when the cinnamic acid, or analog thereof, is a hydroxycinnamic acid, the host cell lacks any enzyme capable of catalyzing the decarboxylation of a hydroxycinnamic acid.

In some embodiments of the invention, the HCBT is a *Dianthus caryophyllus* HCBT or *Ipomoea batatas* (sweet potato) HCBT.

The amino acid sequence of *Dianthus caryophyllus* HCBT is as follows:

```
                                                           (SEQ ID NO:1)
  1 msihikqstm vrpaeetpnk slwlskidmi lrtpyshtga vliykqpdnn edniqpsssm 61 yfdaniliea lskalvpyyp magrlkingd ryeidcngeg alfveaessh vledfgdfrp 121 ndelhrvmvp tcdyskgiss fpllmvqltr frcggvsigf aqhhhvcdrm shfefnnswa 181 riakgllpal epvhdrylhl cprnppqiky thsqfepfvp slpkelldgk tsksqtlfkl
```

-continued

```
241 sreqintlkq kldwsntttr lstyevvagh vwrsvskarg lsdheeikli mpvdgrsrin 301 npslpkgycg nvvflavcta tvgdlacnpl tdtagkvqea lkgldddylr saidhteskp 361 dlpvpymgsp ektlypnvlv nswgripyqa mdfgwgnptf fgisnifydg qcflipsqng 421 dgsmtlainl fsshlslfkk hfydf
```

The amino acid sequence of *Ipomoea batatas* (sweet potato) HCBT is as follows:

(SEQ ID NO:2)
```
  1 masekfkisi kestmvkpak ptpakrlwns nldlivgrih lltvyfyrpn gspnffdskv 61 mkealsnvlv sfypmagrla rdgegrieid cneegvlfve aesdacvddf gdftpslelr 121 kfiptvdtsg dissfpliif qvtrfkcggv clgtgvfhtl sdgcsslhfi ntwsdmargl 181 svaippfidr tllrardppt pafehseydq ppklksvpes krgssasttm lkitpeqlal 241 lktkskhegs tyeilaahiw rcackarglt ddqatklyva tdgrsrlcpp lppgylgnvv 301 ftatpmaesg elqsepltns akrihsalsr mddeylrsal dflecqpdls klirgsnyfa 361 spnlninswt rlpvhesdfg wgrpihmgpa cilyegtvyi lspnkdrtl slavcldaeh 421 mplfkeflyd f
```

In some embodiments of the invention, the 4CL is the 4-coumarate:CoA ligase 5 (4CL5) of *Arabidopsis thaliana*, which is capable of converting various hydroxycinnamic acids into the corresponding CoA thioesters.

The amino acid sequence of *Arabidopsis thaliana* 4CL5 is as follows:

(SEQ ID NO:3)
```
  1 mvlqqqthfl tkkidqedee eepshdfifr sklpdifipn hlpltdyvfq rfsgdgdgds 61 sttiidgat  griltyadvq tnmrriaagi hrlgirhgdv vmlllpnspe falsflavay 121 lgavsttanp fytqpeiakq akasaakmii tkkclvdklt nlkndgvliv cldddgdngv 181 vsssddgcvs fteltqadet ellkpkispe dtvampyssg ttglpkgvmi thkglvtsia 241 qkvdgenpnl nftandvilc flpmfhiyal dalmlsamrt gaallivprf elnlvmeliq 301 rykvtvvpva ppvvlafiks peterydlss vrimlsgaat lkkeledavr lkfpnaifgq 361 gygmtesgtv akslafaknp fktksgacgt virnaemkvv dtetgislpr nksgeicvrg 421 hqlmkgylnd peatartidk dgwlhtgdig fvddddeifi vdrlkelikf hgyqvapael 481 eallishpsi ddaavvamkd evadevpvaf varsqgsqlt eddvksyvnk qvvhykrikm 541 vffievipka vsgkilrkdl rakletmcsk
```

In some embodiments of the invention, the host cell in its unmodified form has a native enzyme capable of catalyzing the decarboxylation of a hydroxycinnamic acid is a phenylacrylic decarboxylase. In yeast the phenylacrylic decarboxylase is encoded by the pad1 gene. In some embodiments of the invention, the gene encoding the enzyme capable of catalyzing the decarboxylation of a hydroxycinnamic acid is deleted or modified such that expression of the gene is reduced or eliminated. The elimination or reduction of expression of the enzyme capable of catalyzing the decarboxylation of a hydroxycinnamic acid results in the reduced degradation of the hydroxycinnamic acid. In some embodiments of the invention, the host cell has a reduced capability to catabolize, metabolize, or modify a hydroxycinnamic acid, or analog thereof.

In some embodiments of the invention, the cinnamoyl anthranilate, or analog thereof, has the following chemical structure:

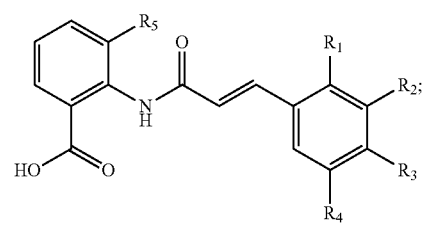

wherein $R_1$, $R_2$, and $R_3$ are each independently H, OH, or $OCH_3$; $R_4$ is H or $OCH_3$; and, $R_5$ is H or OH.

In some embodiments of the invention, the cinnamoyl anthranilate, or analog thereof, is one of the following compounds:

N-(4'-Hydroxycinnamoyl)-anthranilic acid (Avn D) ($R_1$=$R_2$=$R_4$=$R_5$=H, $R_3$=OH)
N-(2'-Hydroxycinnamoyl)-anthranilic acid ($R_2$=$R_3$=$R_4$=$R_5$=H, $R_1$=OH)
N-(3'-Hydroxycinnamoyl)-anthranilic acid ($R_1$=$R_3$=$R_4$=$R_5$=H, $R_2$=OH)
N-(3',4'-Dihydroxycinnamoyl)-anthranilic acid (Avn E) ($R_1$=$R_4$=$R_5$=H, $R_2$=$R_3$=H)
N-(3'-Methoxy-4'-hydroxycinnamoyl)-anthranilic acid (Avn F) ($R_1$=$R_4$=$R_5$=H, $R_2$=$OCH_3$, $R_3$=OH)
N-(3',5'-Dimethoxy-4'-hydroxycinnamoyl)-anthranilic acid ($R_1$=$R_5$=H, $R_2$=$R_4$=$OCH_3$, $R_3$=OH)
N-(Cinnamoyl)-anthranilic acid ($R_1$=$R_2$=$R_3$=$R_4$=$R_5$=H)
N-(3',4'-Dimethoxycinnamoyl)-anthranilic acid (tranilast) ($R_1$=$R_4$=$R_5$=H, $R_2$=$R_3$=$OCH_3$)
N-(3',4',5'-Trimethoxycinnamoyl)-anthranilic acid ($R_1$=$R_5$=H, $R_2$=$R_3$=$R_4$=$OCH_3$)
N-(4'-Methoxycinnamoyl)-anthranilic acid ($R_1$=$R_2$=$R_4$=$R_5$=H, $R_3$=$OCH_3$)
N-(3'-Hydroxy-4'-methoxycinnamoyl)-anthranilic acid ($R_1$=$R_4$=$R_5$=H, $R_2$=OH, $R_3$=$OCH_3$)
N-(3'-Methoxycinnamoyl)-anthranilic acid ($R_1$=$R_3$=$R_4$=$R_5$=H, $R_2$=$OCH_3$)
N-(2',3'-Dimethoxycinnamoyl)-anthranilic acid ($R_3$=$R_4$=$R_5$=H, $R_1$, $R_2$=$OCH_3$)
N-(2',4'-Dimethoxycinnamoyl)-anthranilic acid ($R_2$=$R_4$=$R_5$=H, $R_1$=$R_3$=$OCH_3$)
N-(2',5'-Dimethoxycinnamoyl)-anthranilic acid ($R_2$=$R_3$=$R_5$=H, $R_1$=$R_4$=$OCH_3$)
N-(4'-Hydroxycinnamoyl)-3-hydroxyanthranilic acid ($R_1$=$R_2$=$R_4$=H, $R_3$=$R_5$=OH)
N-(2'-Hydroxycinnamoyl)-3-hydroxyanthranilic acid ($R_2$=$R_3$=$R_4$=H, $R_1$=$R_5$=OH)
N-(3'-Hydroxycinnamoyl)-3-hydroxyanthranilic acid ($R_1$, $R_3$=$R_4$=H, $R_2$=$R_5$=OH)
N-(3',4'-Dihydroxycinnamoyl)-3-hydroxyanthranilic acid ($R_1$=$R_4$=H, $R_2$=$R_3$=$R_5$=OH)

In some embodiments of the invention, the cinnamoyl anthranilate, or analog thereof, has the following chemical structure:

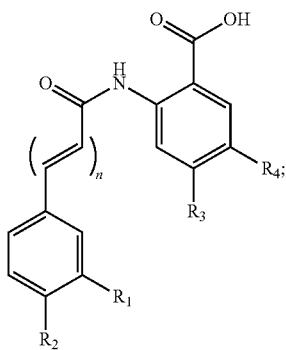

wherein $R_1$ is H, OH, or $OCH_3$; $R_2$ is OH; $R_3$ is H or OH; $R_4$ is H or OH; and, n is 1 or 2.

In some embodiments of the invention, the cinnamoyl anthranilate, or analog thereof, is one of the following compounds (Avn: avenanthramide):

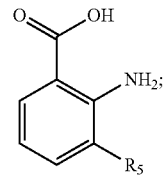

| Avn | $R_1$ | $R_2$ | $R_3$ | $R_4$ | n |
|---|---|---|---|---|---|
| A | H | OH | H | OH | 1 |
| B | $OCH_3$ | OH | H | OH | 1 |
| C | OH | OH | H | OH | 1 |
| G | H | OH | OH | H | 1 |
| H | $OCH_3$ | OH | OH | H | 1 |
| O | H | OH | H | OH | 2 |
| R | H | OH | OH | H | 2. |

In some embodiments of the invention, the anthranilate, or analog thereof, has the following chemical structure:

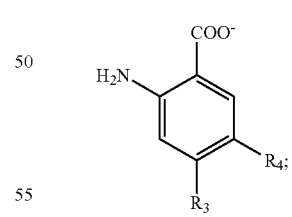

wherein $R_5$ is H or OH.

In some embodiments of the invention, the anthranilate, or analog thereof, is anthranilate ($R_5$=H) or 3-hydroxyanthranilate ($R_5$=OH).

In some embodiments of the invention, the anthranilate, or analog thereof, has the following chemical structure:

wherein $R_3$ is H or OH; $R_4$ is H or OH. In some embodiments of the invention, $R_3$ is H and $R_4$ is H. In some embodiments of the invention, $R_3$ is H and $R_4$ is OH. In some embodiments of the invention, $R_3$ is OH and $R_4$ is H. In some embodiments of the invention, $R_3$ is OH and $R_4$ is OH.

In some embodiments of the invention, the cinnamoyl-CoA, or analog thereof, has the following chemical structure:

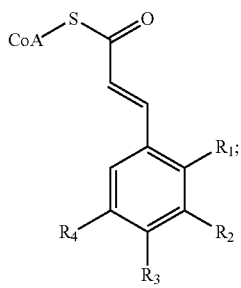

wherein $R_1$, $R_2$, and $R_3$ are each independently H, OH, or $OCH_3$; and $R_4$ is H or $OCH_3$.

In some embodiments of the invention, the cinnamoyl-CoA, or analog thereof, is one of the following compounds:

p-Coumaroyl-CoA ($R_1=R_2=R_4=H$, $R_3=OH$)
o-Coumaroyl-CoA ($R_2=R_3=R_4=H$, $R_1=OH$)
m-Coumaroyl-CoA ($R_1=R_3=R_4=H$, $R_2=OH$)
Caffeoyl-CoA ($R_1=R_4=H$, $R_2=R_3=OH$)
Feruloyl-CoA ($R_1=R_4=H$, $R_2=OCH_3$, $R_3=OH$)
Sinapoyl-CoA ($R_1=H$, $R_2=R_4=OCH_3$, $R_3=OH$)
Cinnamoyl-CoA ($R_1=R_2=R_3=R_4=H$)
3,4-Dimethoxycinnamoyl-CoA ($R_1=R_4=H$, $R_2=R_3=OCH_3$)
3,4,5-Trimethoxycinnamoyl-CoA ($R_1=H$, $R_2=R_3=R_4=OCH_3$)
4-Methoxycinnamoyl-CoA ($R_1=R_2=R_4=H$, $R_3=OCH_3$)
3-Hydroxy-4-methoxycinnamoyl-CoA ($R_1=R_4=H$, $R_2=OH$, $R_3=OCH_3$)
3-Methoxycinnamoyl-CoA ($R_1=R_3=R_4=H$, $R_2=OCH_3$)
2,3-Dimethoxycinnamoyl-CoA ($R_3=R_4=H$, $R_1=R_2=OCH_3$)
2,4-Dimethoxycinnamoyl-CoA ($R_2=R_4=H$, $R_1=R_3=OCH_3$)
2,5-Dimethoxycinnamoyl-CoA ($R_2=R_3=H$, $R_1=R_4=OCH_3$)

In some embodiments of the invention, the cinnamoyl-CoA, or analog thereof, has the following chemical structure:

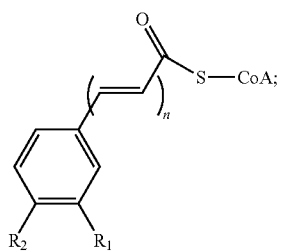

wherein $R_1$ is H, OH, or $OCH_3$; and $R_2$ is OH.

In some embodiments of the invention, the cinnamic acid, or analog thereof, is naturally occurring or non-naturally occurring. In some embodiments of the invention, the cinnamic acid, or analog thereof, has the following chemical structure:

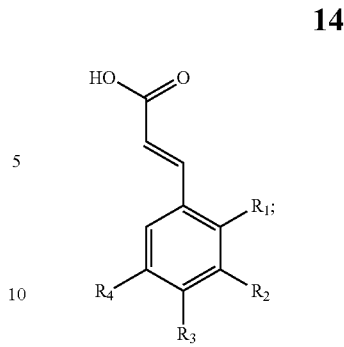

wherein $R_1$, $R_2$, and $R_3$ are each independently H, OH, or $OCH_3$; and $R_4$ is H or $OCH_3$.

In some embodiments of the invention, the cinnamic acid, or analog thereof, is one of the following compounds:

p-Coumaric acid ($R_1$, $R_2=R_4=H$, $R_3=OH$)
o-Coumaric acid ($R_2=R_3=R_4=H$, $R_1=OH$)
m-Coumaric acid ($R_1=R_3=R_4=H$, $R_2=OH$)
Caffeic acid ($R_1=R_4=H$, $R_2=R_3=OH$)
Ferulic acid ($R_1=R_4=H$, $R_2=OCH_3$, $R_3=OH$)
Sinapic acid ($R_1=H$, $R_2=R_4=OCH_3$, $R_3=OH$)
Cinnamic acid ($R_1=R_2=R_3=R_4=H$)
3,4-Dimethoxycinnamic acid ($R_1=R_4=H$, $R_2=R_3=OCH_3$)
3,4,5-Trimethoxycinnamic acid ($R_1=H$, $R_2=R_3=R_4=OCH_3$)
4-Methoxycinnamic acid ($R_1=R_2=R_4=H$, $R_3=OCH_3$)
3-Hydroxy-4-methoxycinnamic acid ($R_1=R_4=H$, $R_2=OH$, $R_3=OCH_3$)
3-Methoxycinnamic acid ($R_1=R_3=R_4=H$, $R_2=OCH_3$)
2,3-Dimethoxycinnamic acid ($R_3$, $R_4=H$, $R_1=R_2=OCH_3$)
2,4-Dimethoxycinnamic acid ($R_2=R_4=H$, $R_1=R_3=OCH_3$)
2,5-Dimethoxycinnamic acid ($R_2=R_3=H$, $R_1=R_4=OCH_3$)

The present invention covers further anthranilate analogs such as 5-halo-anthranilate, such as 5-fluoro-anthranilate.

The present invention also provides for a genetically modified host cell useful for the methods of the present invention. In some embodiments of the present invention, the genetically modified host cell comprises a HCBT, or functional fragment thereof, and optionally a 4CL, or functional fragment thereof. In some embodiments of the present invention, the genetically modified host cell comprises a first nucleic acid sequence encoding a HCBT, or functional fragment thereof, and optionally a second nucleic acid sequence encoding a 4CL, or functional fragment thereof. The first nucleic acid sequence is capable of expressing the HCBT, or functional fragment thereof. The second nucleic acid sequence is capable of expressing the 4CL, or functional fragment thereof. The first and second nucleic acid sequences can each independently be on a single nucleic acid sequence, or separate nucleic acid sequences. Each nucleic acid sequence can independently be integrated into a chromosome or reside on a vector, such as an expression vector. Alternately the first and second nucleic acid sequences can each independently be transient.

The present invention further provides for an isolated cinnamoyl anthranilate, or analog thereof, produced from the method of the present invention.

In a particular embodiment of the invention, the host cell is a yeast strain modified to co-express a 4-coumarate:CoA ligase (4CL, EC 6.2.1.12) from *Arabidopsis thaliana* and a hydroxycinnamoyl/benzoyl-CoA:anthranilate N-hydroxycinnamoyl/benzoyltransferase (HCBT, EC 2.3.1.144) from *Dianthus caryophyllus*. This modified yeast strain is capable of producing tranilast and twenty six different cinnamoyl anthranilate molecules within a few minutes/hours after exogenous supply of various combinations of cinnamic acids and anthranilate derivatives.

The nucleic acid constructs of the present invention comprise nucleic acid sequences encoding one or more of the subject enzymes. The nucleic acid of the subject enzymes are operably linked to promoters and optionally control sequences such that the subject enzymes are expressed in a host cell cultured under suitable conditions. The promoters and control sequences are specific for each host cell species. In some embodiments, expression vectors comprise the nucleic acid constructs. Methods for designing and making nucleic acid constructs and expression vectors are well known to those skilled in the art.

Sequences of nucleic acids encoding the subject enzymes are prepared by any suitable method known to those of ordinary skill in the art, including, for example, direct chemical synthesis or cloning. For direct chemical synthesis, formation of a polymer of nucleic acids typically involves sequential addition of 3'-blocked and 5'-blocked nucleotide monomers to the terminal 5'-hydroxyl group of a growing nucleotide chain, wherein each addition is effected by nucleophilic attack of the terminal 5'-hydroxyl group of the growing chain on the 3'-position of the added monomer, which is typically a phosphorus derivative, such as a phosphotriester, phosphoramidite, or the like. Such methodology is known to those of ordinary skill in the art and is described in the pertinent texts and literature (e.g., in Matteuci et al. (1980) *Tet. Lett.* 521:719; U.S. Pat. Nos. 4,500,707; 5,436,327; and 5,700,637). In addition, the desired sequences may be isolated from natural sources by splitting DNA using appropriate restriction enzymes, separating the fragments using gel electrophoresis, and thereafter, recovering the desired nucleic acid sequence from the gel via techniques known to those of ordinary skill in the art, such as utilization of polymerase chain reactions (PCR; e.g., U.S. Pat. No. 4,683,195).

Each nucleic acid sequence encoding the desired subject enzyme can be incorporated into an expression vector. Incorporation of the individual nucleic acid sequences may be accomplished through known methods that include, for example, the use of restriction enzymes (such as BamHI, EcoRI, HhaI, XhoI, XmaI, and so forth) to cleave specific sites in the expression vector, e.g., plasmid. The restriction enzyme produces single stranded ends that may be annealed to a nucleic acid sequence having, or synthesized to have, a terminus with a sequence complementary to the ends of the cleaved expression vector. Annealing is performed using an appropriate enzyme, e.g., DNA ligase. As will be appreciated by those of ordinary skill in the art, both the expression vector and the desired nucleic acid sequence are often cleaved with the same restriction enzyme, thereby assuring that the ends of the expression vector and the ends of the nucleic acid sequence are complementary to each other. In addition, DNA linkers may be used to facilitate linking of nucleic acids sequences into an expression vector.

A series of individual nucleic acid sequences can also be combined by utilizing methods that are known to those having ordinary skill in the art (e.g., U.S. Pat. No. 4,683,195).

For example, each of the desired nucleic acid sequences can be initially generated in a separate PCR. Thereafter, specific primers are designed such that the ends of the PCR products contain complementary sequences. When the PCR products are mixed, denatured, and reannealed, the strands having the matching sequences at their 3' ends overlap and can act as primers for each other. Extension of this overlap by DNA polymerase produces a molecule in which the original sequences are "spliced" together. In this way, a series of individual nucleic acid sequences may be "spliced" together and subsequently transduced into a host microorganism simultaneously. Thus, expression of each of the plurality of nucleic acid sequences is effected.

Individual nucleic acid sequences, or "spliced" nucleic acid sequences, are then incorporated into an expression vector. The invention is not limited with respect to the process by which the nucleic acid sequence is incorporated into the expression vector. Those of ordinary skill in the art are familiar with the necessary steps for incorporating a nucleic acid sequence into an expression vector. A typical expression vector contains the desired nucleic acid sequence preceded by one or more regulatory regions, along with a ribosome binding site, e.g., a nucleotide sequence that is 3-9 nucleotides in length and located 3-11 nucleotides upstream of the initiation codon in *E. coli*. See Shine et al. (1975) *Nature* 254:34 and Steitz, in Biological Regulation and Development: Gene Expression (ed. R. F. Goldberger), vol. 1, p. 349, 1979, Plenum Publishing, N.Y.

Regulatory regions include, for example, those regions that contain a promoter and an operator. A promoter is operably linked to the desired nucleic acid sequence, thereby initiating transcription of the nucleic acid sequence via an RNA polymerase enzyme. An operator is a sequence of nucleic acids adjacent to the promoter, which contains a protein-binding domain where a repressor protein can bind. In the absence of a repressor protein, transcription initiates through the promoter. When present, the repressor protein specific to the protein-binding domain of the operator binds to the operator, thereby inhibiting transcription. In this way, control of transcription is accomplished, based upon the particular regulatory regions used and the presence or absence of the corresponding repressor protein. Examples include lactose promoters (LacI repressor protein changes conformation when contacted with lactose, thereby preventing the LacI repressor protein from binding to the operator) and tryptophan promoters (when complexed with tryptophan, TrpR repressor protein has a conformation that binds the operator; in the absence of tryptophan, the TrpR repressor protein has a conformation that does not bind to the operator). Another example is the tac promoter. (See deBoer et al. (1983) *Proc. Natl. Acad. Sci. USA,* 80:21-25.) As will be appreciated by those of ordinary skill in the art, these and other expression vectors may be used in the present invention, and the invention is not limited in this respect.

Although any suitable expression vector may be used to incorporate the desired sequences, readily available expression vectors include, without limitation: plasmids, such as pSC101, pBR322, pBBR1MCS-3, pUR, pEX, pMR100, pCR4, pBAD24, pUC19; bacteriophages, such as M13 phage and λ phage. Of course, such expression vectors may only be suitable for particular host cells. One of ordinary skill in the art, however, can readily determine through routine experimentation whether any particular expression vector is suited for any given host cell. For example, the expression vector can be introduced into the host cell, which is then monitored for viability and expression of the sequences contained in the vector. In addition, reference may be made to the relevant texts and literature, which describe expression vectors and their suitability to any particular host cell.

The expression vectors of the invention must be introduced or transferred into the host cell. Such methods for transferring the expression vectors into host cells are well known to those of ordinary skill in the art. For example, one method for transforming *E. coli* with an expression vector involves a calcium chloride treatment wherein the expression vector is introduced via a calcium precipitate. Other salts, e.g., calcium phosphate, may also be used following a similar procedure. In addition, electroporation (i.e., the application of current to increase the permeability of cells to nucleic acid sequences) may be used to transfect the host microorganism. Also, microinjection of the nucleic acid sequencers) provides the ability to transfect host microorganisms. Other means, such as lipid complexes, liposomes, and dendrimers, may also be employed. Those of ordinary skill in the art can transfect a host cell with a desired sequence using these or other methods.

For identifying a transfected host cell, a variety of methods are available. For example, a culture of potentially transfected host cells may be separated, using a suitable dilution, into individual cells and thereafter individually grown and tested for expression of the desired nucleic acid sequence. In addition, when plasmids are used, an often-used practice involves the selection of cells based upon antimicrobial resistance that has been conferred by genes intentionally contained within the expression vector, such as the amp, gpt, neo, and hyg genes.

The host cell can be transformed with at least one expression vector. When only a single expression vector is used (without the addition of an intermediate), the vector will contain all of the nucleic acid sequences necessary.

Once the host cell has been transformed with the expression vector, the host cell is allowed to grow. For microbial hosts, this process entails culturing the cells in a suitable medium. It is important that the culture medium contain an excess carbon source, such as a sugar (e.g., glucose) when an intermediate is not introduced. The host cell can optionally be exogenously fed an anthranilate, or analog thereof, and/or a cinnamic acid, or analog thereof, or be capable of synthesizing one or both of these compounds endogenously. When added, these compounds are present in an excess amount in the culture medium.

As the host cell grows and/or multiplies, expression of the enzymes necessary for producing the cinnamoyl anthranilate, or analog thereof, is effected. Once expressed, the enzymes catalyze the steps necessary for carrying out the steps of cinnamoyl-CoA or cinnamoyl anthranilate, or analog thereof, production. Any means for recovering the cinnamoyl anthranilate, or analog thereof, from the host cell or culture medium may be used. For example, the host cell may be harvested and subjected to hypotonic conditions, thereby lysing the cells. The lysate may then be centrifuged and the supernatant subjected to high performance liquid chromatography (HPLC) or gas chromatography (GC).

Host Cells

The host cells of the present invention are genetically modified in that heterologous nucleic acid have been introduced into the host cells, and as such the genetically modified host cells do not occur in nature. The suitable host cell is one capable of expressing a nucleic acid construct encoding an enzyme capable of catalyzing the production of cinnamoyl-CoA or cinnamoyl anthranilate, or analog thereof. The gene encoding the enzyme may be heterogous to the host cell or the gene may be native to the host cell but is operatively linked to a heterologous promoter and one or more control regions which result in a higher expression of the gene in the host cell. The enzyme capable of catalyzing the production of cinnamoyl-CoA or cinnamoyl anthranilate, or analog thereof can be native or heterologous to the host cell. Where the enzyme is native to the host cell, the host cell is genetically modified to modulate expression of the enzyme. This modification can involve the modification of the chromosomal gene encoding the enzyme in the host cell or a nucleic acid construct encoding the gene of the enzyme is introduced into the host cell. One of the effects of the modification is the expression of the enzyme is modulated in the host cell, such as the increased expression of the enzyme in the host cell as compared to the expression of the enzyme in an unmodified host cell.

Any prokaryotic or eukaryotic host cell may be used in the present method so long as it remains viable after being transformed with a sequence of nucleic acids. Generally, although not necessarily, the host microorganism is bacterial. In some embodiments, the bacterium is a cyanobacteria. Examples of bacterial host cells include, without limitation, those species assigned to the *Escherichia, Enterobacter, Azotobacter, Erwinia, Bacillus, Pseudomonas, Klebsielia, Proteus, Salmonella, Serratia, Shigella, Rhizobia, Vitreoscilla, Synechococcus, Synechocystis*, and *Paracoccus* taxonomical classes. Preferably, the host cell is not adversely affected by the transduction of the necessary nucleic acid sequences, the subsequent expression of the proteins (i.e., enzymes), or the resulting intermediates required for carrying out the steps associated with the mevalonate pathway. For example, it is preferred that minimal "cross-talk" (i.e., interference) occur between the host cell's own metabolic processes and those processes involved with the mevalonate pathway.

Suitable eukaryotic cells include, but are not limited to, plant, algae, fungal, insect or mammalian cells. Suitable fungal cells are yeast cells, such as yeast cells of the *Saccharomyces* genus, such as *Saccharomyces cerevisiae*.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

Example 1

In this study we produce cinnamoyl anthranilates in *Saccharomyces cerevisiae* by introducing two genes from two different plant species (FIG. 1b). The first gene encodes the hydroxycinnamoyl/benzoyl-CoA:anthranilate N-hydroxycinnamoyl/benzoyltransferase (HCBT), an enzyme from *Dianthus caryophyllus*, which has affinity for anthranilate and p-coumaroyl-CoA and is capable of producing N-(4'-hydroxycinnamoyl)-anthranilate in vitro (Yang et al. 1997). The second gene encodes 4-coumarate:CoA ligase 5 (4CL5) from *Arabidopsis thaliana*, which converts various hydroxycinnamic acids into the corresponding CoA thioesters (Hamberger and Hahlbrock 2004). This enzyme was required since the hydroxycinnamoyl-CoA thioesters are unstable, commercially unavailable, membrane impermeable, and not naturally produced in yeast. Additionally, in order to reduce the degradation of the 4CL5 substrates, we used a yeast strain lacking pad1, which encodes a phenylacrylic decarboxylase known to catalyze the decarboxylation of several hydroxycinnamic acids (Mukai et al. 2010). Our findings show that the engineered yeast strain was able to produce the pharmaceutical drug tranilast and a variety of known or uncharacterized analogs after incubation with anthranilate, 3-hydroxyanthranilate, and various natural or synthetic cinnamic acids.

Generation of a Shuttle Vector for Gene Coexpression in Yeast

Material and Methods

Chemicals

Ferulic acid, p-coumaric acid, 2,5-dimethoxycinnamic acid, 2,4-dimethoxycinnamic, and caffeic acid were purchased from TCI America (Portland, Oreg.). Cinnamic acid, Sinapic acid, o-coumaric acid, m-coumaric acid, 3-hydroxy-4-methoxycinnamic acid, 3,4-dimethoxycinnamic acid, 3,4,5-trimethoxycinnamic acid, 3-methoxycinnamic acid, 4-methoxycinnamic acid, 2,3-dimethoxycinnamic acid, anthranilate, 3-hydroxyanthranilate, tranilast [N-(3',4'-dimethoxycinnamoyl)-anthranilic acid], dithiothreitol, phenylmethanesulfonylfluoride, and protease inhibitor cocktail were purchased from Sigma-Aldrich (St. Louis, Mo.). All chromatographic solvents were HPLC grade and purchased from local suppliers.

Chemical Synthesis of
N-(4'-Hydroxy-(E)-Cinnamoyl)-Anthranilate

N-4'-(Hydroxy-(E)-cinnamoyl)-anthranilate was prepared as described (Collins 1989). Briefly, acid 4-acetoxy-(E,Z)-cinnamoyl chloride was prepared from 4-hydroxy-(E,Z)-cinnamic acid by acetylation with acetic anhydride (Sigma-Aldrich, St. Louis, Mo., p-toluenesulfonic acid catalyst) and treatment of the recrystallized (hot MeOH) 4-acetoxy-(E,Z)-cinnamic acid with excess thionyl chloride (Sigma-Aldrich, St. Louis, Mo.) according to the procedures of Fosdick and Starke (1940). Removal of excess thionyl chloride by repeated rotary evaporation and washing with acetone gave a crude acid chloride containing no detectable free 4-acetoxy-(E,Z)-cinnamic acid. The crude acid chloride was found suitable for subsequent reactions and was used without further purification. A solution of 135 mg (1 mmol) of anthranilic acid was condensed with the dried residue corresponding to (1 mmol) 4-acetoxy-(E,Z)-cinnamoyl chloride. After deacylation with mild alkali, the products were purified by repeated chromatography on a Sephadex LH-20 resin (GE Healthcare, Piscataway, N.J.) using glass columns and a gravity-flow isocratic elution in $CHCl_3$-cyclohexane-MeOH-acetic acid (50:40:5:5 v:v:v:v by %) and $CHCl_3$-cyclohexane-MeOH-acetic acid (50:35:105 v:v:v:v by %) to give N-4'-hydroxy-(E)-cinnamoyl-2-aminobenzoic acid (yield 235 mg (83%) and a small amount of the Z isomer. Crystallization of the E isomer from hot acetone-water gave colorless rods: mp 219° C.; $C_{16}H_{13}NO_4$; $M.^+$ 283; UV (MeOH) $\lambda_{max}$ (log ε) 218 (4.30), 294s, (4.25), 302s, (4.33), 329 (4.47) nm; UV (MeOH+NaOH) $\lambda_{max}$ (log ε) 213 (4.43), 233s, (4.19), 306s, (4.05), 314 (4.08), 371 (4.51) nm.

Generation of a Shuttle Vector for Gene Coexpression in Yeast

We generated a yeast shuttle vector pDRf1-GW-$P_{HXT7}$ which contains a Gateway cloning cassette (Invitrogen, Carlsbad, Calif.) inserted between the PMA1 promoter ($P_{PMA1}$) and the ADH1 terminator ($T_{ADH1}$), and carries a second yeast expression cassette inserted into the SphI restriction site at the 3'-end of $T_{ADH1}$. This cassette contains the HXT7 promoter ($P_{HXT7}$) and the CYC1 terminator ($T_{CYC1}$), both separated by a multicloning site containing a NotI restriction site ($P_{HXT7}$-$T_{CYC1}$). The $P_{HXT7}$-$T_{CYC1}$ and $P_{PMA1}$-$T_{ADH1}$ expression cassettes are in the same orientation. To generate a pDRf1-GW-$P_{HXT7}$ co-expression vector, the yeast shuttle vector p426 (Wieczorke et al. 1999) was first modified by site-directed mutagenesis (Kunkel 1985) to insert two SphI restriction sites at the 5'-end of $P_{HXT7}$ and the 3'-end of $T_{CYC1}$ using the following primers 5'-CGAAATT-GTTCCTACGAGCTCGCATGCTTTTGTTCCCTTTAGT-GAGG-3' (SEQ ID NO:4) and 5'-GACTCACTATAGGGC-GAATTGGCATGCGGCCGCAAATTAAAGCCTTC-3' (SEQ ID NO:5), respectively. This vector was further modified to insert the unique NotI restriction site between $P_{HXT7}$ and $T_{CYC1}$. The multi-cloning site and the sequence encoding a His-tag located between $P_{HXT7}$ and $T_{CYC1}$ was replaced by site-directed mutagenesis (Kunkel 1985) using the following primer 5'-CATAACTAATTACATGACTCGAGCG-GCCGCCCGGGGGATCCACTAGA-3' (SEQ ID NO:6). After mutagenesis, the $P_{HXT7}$-$T_{CYC1}$ expression cassette was sequence-verified, digested with SphI (Fermentas Inc., Glen Burnie, Md.) and inserted into the unique SphI restriction site of pDRf1-GW located at the $T_{ADH1}$ 3'-end (Loqué et al. 2006).

Construction and Expression of Recombinant Yeast Harboring 4CL5 and HCBT

The 4CL5 gene (At3g21230) was cloned from *Arabidopsis thaliana* (ecotype Columbia). Four μg of total RNA was isolated from mixed organs of *Arabidopsis* plants using the RNeasy Plant Mini Kit (Qiagen, Valencia, Calif.) and used to perform an RT-PCR. First strand cDNAs were synthesized using the Transcriptor High Fidelity cDNA Synthesis kit (Roche, Indianapolis, Ind.) and used to amplify the 4CL5 gene using the following oligonucleotides containing NotI restriction sites: forward, 5'-GCGGCCGCATGGTGCTCCAACAACAAACGC-3' (SEQ ID NO:7); and reverse, 5'-GCGGCCGCCTATTTAGAGCACATGGTTTCC-3' (SEQ ID NO:8) (NotI sites are underlined). The PCR product was subcloned into the pCR-Blunt vector (Invitrogen, Carlsbad, Calif.), digested with NotI restriction enzyme (Fermentas Inc., Glen Burnie, Md.), gel purified, and ligated into the pDRf1-GW-pHXT7 vector at the unique NotI restriction site located between pHXT7 and tCYC1 of the expression cassette. A clone showing correct orientation for the 4CL5 gene was selected and the resulting vector was named pDRf1-4CL5-GW.

To clone the gene encoding HCBT, a gene sequence encoding the HCBT1 protein (O24645) without stop codon and flanked with the attB1 (5'-end) and attB2 (3'-end) Gateway recombination sites was synthesized and codon optimized for yeast expression by GenScript (Piscatway, N.J.). The attB1-HCBT-attB2 fragment was remobilized into the Donor plasmid vector pDONR221-f1 (Lalonde et al. 2010) by in-vitro BP recombination, and transferred into the pDRf1-4CL5-GW and pDRf1-GW-pHXT7 vectors by in-vitro LR recombination using the Gateway technology (Invitrogen, Carlsbad, Calif.). The resulting vectors were named pDRf1-4CL5-HCBT1 and pDRf1-HCBT1. A pDRf1-4CL5 control vector was also generated by in-vitro LR recombination between the pDRf1-4CL5-GW vector and an ENTRY clone containing only a nucleotide sequence corresponding to a PvuII restriction site (CAGCTG) between the attL recombination sites. This six-nucleotide sequence consequently replaced both the ccdB and chloramphenicol resistance genes of the Gateway cassette in the pDRf1-4CL5-GW vector.

pDRf1-4CL5-HCBT1, pDRf1-HCBT1 and pDRf1-4CL5 were transformed into the *S. cerevisiae* pad1 knockout (MATa his3Δ1 leu2Δ0 met15Δ0 ura3Δ0 Δpad1, ATCC 4005833; Winzeler et al. 1999) using the lithium acetate transformation method (Gietz and Woods 2002) and selected on solid medium containing Yeast Nitrogen Base (YNB) without amino acids (Difco 291940; Difco, Detroit, Mich.) supplemented with 3% glucose and 1× dropout-uracil (CSM-ura; Sunrise Science Products, San Diego, Calif.).

HCBT Expression Analysis

The codon optimized HCBT clone was synthesized without a stop codon, therefore generating an in-frame C-terminal tag corresponding to the PAFLYKW peptide (SEQ ID NO:10) after translation of the attB2 site obtained after LR recombination. A polyclonal antibody was raised against an AttB2 peptide (DPAFLYKVVD (SEQ ID NO:9)) using rabbit as a host, and purified using an affinity column (Biogenes, Berlin, Germany). The purified serum was named 'universal antibody' since it can be used to quantify the expression level of any protein expressed with any Gateway destination vectors (Invitrogen, Carlsbad, Calif.).

For soluble protein extraction, overnight cultures from single colonies were used to inoculated 50 ml of 2× yeast nitrogen base medium without amino acids (Difco, Detroit, Mich.) supplemented with 6% glucose and 2× CSM-Ura (Sunrise Science Products, San Diego, Calif.) at an $OD_{600}$=0.15, and incubated at 30° C. until it reached $OD_{600}$=1. Cells were centrifuged at 4500×g for 5 min at 4° C. and washed with one volume of chilled-water. The cell pellets were resuspended in 300 μL of CelLytic-Y yeast cell lysis/extraction reagent (Sigma-Aldrich, St. Louis, Mo.) supplemented with 10 mM dithiothreitol, 2 mM phenylmethanesulfonylfluoride, and 2% protease inhibitor cocktail (v/v, P8215 Sigma, St. Louis, Mo.). Approximately 200 μL of acid-washed glass beads (Sigma, St. Louis, Mo.) were added to the mixture, which was then vortexed ten times for 30 sec, and centrifuged at 10,000×g for 5 min at 4° C. to collect the supernatant. Samples were maintained on ice between vortexing steps. The supernatant containing soluble proteins was collected and used for immunoblotting.

Protein concentration was quantified using the Bradford method (Bradford 1976) and bovine serum albumin as a standard. For electrophoresis, soluble protein (5 μg) were mixed with 0.2 M Tris-HCl, pH 6.5, 8% (w/v) SDS, 8% (v/v) β-mercaptoethanol, 40% (v/v) glycerol, and 0.04% (w/v) bromophenol blue and incubated at 40° C. for 30 min. Proteins were separated by SDS-PAGE using 8-16% (w/v) polyacrylamide gradient gels (Invitrogen, Carlsbad, Calif.) and electrotransferred (100 volts, 45 min) onto PVDF membranes (Thermo Fisher Scientific, Rockford, Ill.). Blotted membranes were incubated 1 h in TBS-T (20 mM Tris-HCl, 150 mM NaCl, 0.1% (v/v) Tween 20, pH 7.6) containing 2% (w/v) non-fat milk powder, and incubated overnight with the universal antibody (1:20000) in TBS-T containing 2% (w/v) non-fat milk powder. Membranes were then washed in TBS-T for 30 min and incubated for 1 h with an anti-rabbit secondary antibody conjugated to horseradish peroxidase (1:20000; Sigma-Aldrich, St. Louis, Mo.) in TBS-T containing 2% (w/v) non-fat milk powder. Membranes were then washed in TBS-T for 30 min, and detection was performed by chemiluminescence using the SuperSignal West Dura Extended Duration Substrate (Thermo Fisher Scientific, Rockford, Ill.).

Production of Cinnamoyl Anthranilates

An overnight culture from a single colony of the pDRf1-4CL5-HCBT recombinant yeast grown on 2×YNB medium without amino acids supplemented with 6% glucose and 2×CSM-Ura was used to inoculated 15 mL of fresh minimal medium at an $OD_{600}$=0.15 and shaken at 200 rpm in a 30° C. room. When the 10-mL culture reached an $OD_{600}$=1, all substrates were added at once to reach final concentrations of 500 μM for anthranilate and 3-hydroxyanthranilate, and 300 μM for the cinnamic acids except for 3-methoxycinnamic acid, 4-methoxycinnamic acid, and 2,5-dimethoxycinnamic acid which were supplied at a final concentration of 50 μM due to their negative effect on cell growth at higher concentrations. The cultures were shaken at 200 rpm in a 30° C. room for 15 h for the production of cinnamoyl anthranilates. As negative controls, yeast colonies harboring the pDRf1-HCBT1 or pDRf1-4CL5 vectors were grown using similar conditions.

Detection of Cinnamoyl Anthranilates

For the detection of cinnamoyl anthranilates, an aliquot of the culture medium was collected and cleared by centrifugation (21,000×g for 5 min at 4° C.). The cleared medium was collected, mixed with an equal volume of cold methanol, and filtered using Amicon Ultra centrifugal filters (3,000 Da MW cutoff regenerated cellulose membrane; Millipore, Billerica, Mass.) prior to LC-TOF MS analysis. For the analysis of the tranilast content in yeast cells, the cell pellet from the 10-ml culture was washed three times with water, resuspended in cold methanol-water (1:1, v/v), sonicated twice for 30 s, and centrifuged at 21,000×g for 5 min at 4° C. The supernatant was collected and filtered prior to LC-TOF MS analysis.

The separation of the cinnamoyl anthranilates was conducted on ZIC-HILIC columns (150 or 250 mm length, 2.1 mm internal diameter, and 3.5 μm particle size; from Merck SeQuant, and distributed via The Nest Group, Inc., Southborough, Mass.) using an Agilent Technologies 1200 Series HPLC system (Agilent Technologies, Santa Clara, Calif.). The temperature of the sample tray was maintained at 4° C. by an Agilent FC/ALS Thermostat. The column compartment was set to 40° C. Analytes were eluted isocratically with a mobile phase composition of 50 mM ammonium acetate in water and acetonitrile (2:8, v/v). A flow rate of 0.1 mL/min was used throughout.

The HPLC system was coupled to an Agilent Technologies 6210 time-of-flight mass spectrometer (LC-TOF MS), via a 1/3 post-column split. A LAN card was used to establish the contact between both instrument set-ups in order to trigger the MS into operation upon the initiation of a run cycle from the MassHunter workstation (Agilent Technologies, Santa Clara, Calif.). Electrospray ionization (ESI) was conducted in the negative ion mode and a capillary voltage of −3500 V was utilized. MS experiments were carried out in full scan mode, at 0.85 spectra/second and a cycle time of 1.176 seconds, for the detection of $[M-H]^-$ ions. The instrument was tuned for a range of 50-1700 m/z. Prior to LC-TOF MS analysis, the TOF MS was calibrated via an ESI-L-low concentration tuning mix (Agilent Technologies, Santa Clara, Calif.). Internal reference mass calibration was utilized throughout the chromatographic run via an API TOF reference mass solution kit (Agilent Technologies, Santa Clara, Calif.). Data acquisition and processing were performed by the MassHunter software package.

Quantifications of tranilast and N-(4'-Hydroxycinnamoyl)-anthranilate released in the culture medium and accumulated in yeast cells were made by comparison with a standard curve prepared in methanol-water (1:1, v/v).

Results
Expression Analysis of the HCBT Enzyme in Recombinant Yeast

To verify HCBT expression, we conducted immunoblotting analysis on crude protein extracts obtained from recombinant yeast strains harboring pDRf1-HCBT and pDRf1-4CL5-HCBT, respectively. As shown in FIG. 2, a specific signal corresponding to an approximately 53-kDa protein was detected only in protein extracts derived from the yeast strain harboring the HCBT gene, which is in accordance with the predicted size of HCBT tagged with the AttB2 peptide.

Production of N-(4':Hydroxycinnamoyl)-Anthranilate by the Recombinant Yeast

The HCBT enzyme was previously shown to catalyze the condensation of coumaroyl-CoA and anthranilate to produce N-(4'-hydroxycinnamoyl)-anthranilate in vitro (Yang et al. 1997). Yeast harboring the pDRf1-4CL5-HCBT vector was consequently grown for 15 h in the presence of coumaric acid (300 µM) and anthranilate (500 µM) as precursors, and the medium was analyzed by LC-TOF MS for the detection of the N-(4'-hydroxycinnamoyl)-anthranilate product. Negative control cultures of yeast harboring pDRf1-4CL5, pDRf1-HCBT, or pDRf1 empty vectors were also conducted using the same precursors. LC-TOF MS analysis of the pDRf1-4CL5-HCBT yeast culture medium revealed a peak which was not present in control cultures and which corresponds to N-(4'-hydroxycinnamoyl)-anthranilate by comparison with an authentic standard solution (FIG. 3). The absence of N-(4'-hydroxycinnamoyl)-anthranilate in the yeast expressing 4CL5 alone or HCBT without 4CL5 confirmed the requirement of the 4-coumarate:CoA ligase to produce 4-hydroxycinnamoyl-CoA, and showed that the yeast strain was unable to produce cinnamoyl anthranilates without the HCBT gene. Using these non-optimized culture conditions, the N-(4'-hydroxycinnamoyl)-anthranilate content in the culture medium was estimated to be 14.5 mg/L, which corresponds to a concentration of 51 µM and a conversion yield of 17% based on the starting concentration of coumaric acid. Additionally, the N-(4'-hydroxycinnamoyl)-anthranilate content inside yeast cells accounted for approximately 1.5% of that of the medium (data not shown).

Evaluation of the Recombinant Yeast Strain for the Production of Tranilast Analogs and N-(Hydroxycinnamoyl)-Hydroxyanthranilates Using Known 4CL5 Natural Substrates The tranilast drug corresponds to N-(3',4'-dimethoxycinnamoyl)-anthranilic acid for which one group of analogs feature various substitutions on the cinnamoyl moiety. For the production of such tranilast analogs, three known 4CL5 substrates (ferulic acid, sinapic acid, and caffeic acid) and anthranilate were supplied independently as precursors to the culture medium of recombinant yeast. This approach allowed the biological production of three different tranilast analogs, namely N-(3'-methoxy-4'-hydroxycinnamoyl)-anthranilic acid, N-(3',5'-dimethoxy-4'-hydroxycinnamoyl)-anthranilic acid and N-(3',4'-dihydroxycinnamoyl)-anthranilic acid, respectively (Table 1).

TABLE 1

Characteristics of the N-(hydroxycinnamoyl)-anthranilates produced in yeast and their identification based on dominant ion masses in ESI-MS spectra (FIG. 6).

| Precursors | Compound name | Formula | Theoretical mass [M − H]⁻ | Measured mass [M − H]⁻ | Mass accuracy[a] (ppm) | Retention time (min) |
|---|---|---|---|---|---|---|
| (A) Caffeic acid/anthranilate | N-(3',4'-dihydroxycinnamoyl)-anthranilic acid | $C_{16}H_{13}NO_5$ | 298.072096 | 298.0725 | −1.4 | 7.02 |
| (B) Ferulic acid/anthranilate | N-(3'-methoxy-4'-hydroxycinnamoyl)-anthranilic acid | $C_{17}H_{15}NO_5$ | 312.087746 | 312.08791 | −0.5 | 6.39 |
| (C) Sinapic acid/anthranilate | N-(3',5'-dimethoxy-4'-hydroxycinnamoyl)-anthranilic acid | $C_{18}H_{17}NO_6$ | 342.098311 | 342.09841 | −0.3 | 6.41 |
| (D) p-Coumaric acid/3-hydroxyanthranilate | N-(4'-hydroxycinnamoyl)-3-hydroxyanthranilic acid | $C_{16}H_{13}NO_5$ | 298.072096 | 298.0721 | 0.0 | 6.43 |
| (E) Caffeic acid/3-hydroxyanthranilate | N-(3',4'-dihydroxycinnamoyl)-3-hydroxyanthranilic acid | $C_{16}H_{13}NO_6$ | 314.067011 | 314.06703 | −0.1 | 7.20 |
| (F) Ferulic acid/3-hydroxyanthranilate | N-(3'-methoxy-4'-hydroxycinnamoyl)-3-hydroxyanthranilic acid | $C_{17}H_{15}NO_6$ | 328.082661 | 328.08289 | −0.7 | 6.22 |
| (G) Sinapic acid/3-hydroxyanthranilate | N-(3',5'-dimethoxy-4'-hydroxycinnamoyl)-3-hydroxyanthranilic acid | $C_{18}H_{17}NO_7$ | 358.093225 | 358.0939 | −1.9 | 6.22 |

[a]mass accuracy = [(theoretical mass-measured mass)/(theoretical mass)] × $1.10^6$ Furthermore, in an independent experiment, we supplied 3-hydroxyanthranilate in combination with p-coumaric, ferulic, sinapic, or caffeic acid to the medium of different recombinant yeast cultures since HCBT was also shown to use this anthranilate derivate as a substrate (Yang et al. 1997). Four new N-(hydroxycinnamoyl)-3-hydroxyanthranilates were detected in the media after 15 h of incubation of the recombinant yeast in presence of these precursors (Table 1). LC-TOF MS analysis of the culture medium from each feeding experiment showed unique peaks that were not present in yeast control cultures harboring a pDRf1-4CL5 vector and fed with the same precursors (FIG. 6). The masses were determined for each extracted ion chromatographic peak and compared to the theoretical masses of the predicted compounds that were expected to be produced based on the nature of the precursors used. In all cases, the measured masses agree with the expected theoretical masses within less than 3 ppm mass error. The compounds exhibited exact mass measurements with high mass accuracies, and as a result, the identity of each hydroxycinnamoyl anthranilate was confirmed with a high degree of confidence. Additionally, the seven new molecules produced had similar retention times ranging from 6.22 min to 7.20 min (Table 1).

Production of Tranilast and Additional Analogs Using Various Cinnamic Acids as Precursors Tranilast corresponds to the 4'-methoxylated form of N-(3'-methoxy-4'-hydroxycinnamoyl)-anthranilic acid, which is produced by our recombinant yeast strain when grown in presence of ferulic acid (3-methoxy-4-hydroxycinnamic acid) and anthranilic acid (FIG. 1a, FIG. 1). Therefore, in order to synthesize tranilast biologically, we fed the yeast strain with 3,4-dimethoxycinnamic acid and tested the potential for the heterologously expressed the genes encoding 4CL5 and HCBT to produce and utilize 3,4-dimethoxycinnamoyl-CoA, respectively. The extracted ion chromatograms obtained after LC-TOF MS analysis of both a synthetic tranilast solution and the culture medium collected after feeding the recombinant yeast with anthranilate and 3,4-dimethoxycinnamic acid clearly confirmed tranilast production by the recombinant yeast (FIG. 4). Using these non-optimized culture conditions, the tranilast content in the medium was estimated to be 670 µg/L, which corresponds to a concentration of 2.05 µM and a conversion yield of 0.67% based on the starting concentration of 3,4-dimethoxycinnamic acid. The tranilast content inside the yeast cells accounts for approximately 3.5% of the quantity found in the medium (data not shown). This result demonstrates that 4CL5 is able to convert the unnatural substrate 3,4-dimethoxycinnamic acid into 3,4-dimethoxycinnamoyl-CoA, and the latter being subsequently conjugated to anthranilate by HCBT to form tranilast.

In order to further explore the diversity of tranilast analogs that could potentially be biologically produced with the recombinant yeast strain harboring 4CL5 and HCBT, a large variety of cinnamic acids derivatives were co-fed individually with anthranilate or 3-hydroxyanthranilate. These included cinnamic acid, isoferulic acid, o-coumaric acid, m-coumaric acid, and the 4-methoxy-, 3-methoxy-, 2,3-dimethoxy-, 2,5-dimethoxy-, 2,4-dimethoxy-, 3,4,5-trimethoxy-cinnamic acid derivates. We postulated that the corresponding cinnamoyl-CoA thioesters potentially produced by 4CL5 could be used as substrates by HCBT. This approach successfully led to the production of eighteen additional cinnamoyl anthranilates that could be accurately identified from the culture medium using LC-TOF MS (Table 2, FIG. 7).

TABLE 2

Characteristics of the second series of cinnamoyl anthranilates produced in yeast and their identification based on dominant ion masses in ESI-MS spectra (FIG. 7).

| Precursors | Compound name | Formula | Theoretical mass [M − H]⁻ | Measured mass [M − H]⁻ | Mass accuracy[a] (ppm) | Retention time (min) |
|---|---|---|---|---|---|---|
| (A) cinnamic acid/ anthranilate | N-(cinnamoyl)-anthranilic acid | $C_{16}H_{13}NO_4$ | 282.077181 | 282.07747 | −1.02 | 4.70[b] |
| (B) o-Coumaric acid/ anthranilate | N-(2'-hydroxycinnamoyl)-anthranilic acid | $C_{16}H_{13}NO_4$ | 282.077181 | 282.07755 | −1.31 | 4.63[b] |
| (C) m-Coumaric acid/ anthranilate | N-(3'-hydroxycinnamoyl)-anthranilic acid | $C_{16}H_{13}NO_4$ | 282.077181 | 282.07782 | −2.27 | 4.54[b] |
| (D) 3-Methoxycinnamic acid/anthranilate | N-(3'-methoxycinnamoyl)-anthranilic acid | $C_{17}H_{15}NO_4$ | 296.092832 | 296.09287 | −0.13 | 5.92 |
| (E) 4-Methoxycinnamic acid/anthranilate | N-(4'-methoxycinnamoyl)-anthranilic acid | $C_{17}H_{15}NO_4$ | 296.092832 | 296.09299 | −0.53 | 4.34[b] |
| (F) 2,3-Dimethoxycinnamic acid/ anthranilate | N-(2',3'-dimethoxycinnamoyl)-anthranilic acid | $C_{18}H_{17}NO_5$ | 326.103396 | 326.10344 | −0.13 | 5.88 |
| (G) 2,4-Dimethoxycinnamic acid/ anthranilate | N-(2',4'-dimethoxycinnamoyl)-anthranilic acid | $C_{18}H_{17}NO_5$ | 326.103396 | 326.10341 | −0.04 | 5.77 |
| (H) 2,5-Dimethoxycinnamic acid/ anthranilate | N-(2',5'-dimethoxycinnamoyl)-anthranilic acid | $C_{18}H_{17}NO_5$ | 326.103396 | 326.10339 | 0.02 | 5.92 |
| (I) 3-Hydroxy-4-methoxycinnamic acid/ anthranilate | N-(3'-hydroxy-4'-methoxycinnamoyl)-anthranilic acid | $C_{17}H_{15}NO_5$ | 312.087746 | 312.08713 | 2.0 | 6.37 |
| (J) 3,4,5-Trimethoxycinnamic acid/anthranilate | N-(3',4',5'-trimethoxycinnamoyl)-anthranilic acid | $C_{19}H_{19}NO_6$ | 356.113961 | 356.11406 | −0.3 | 6.02 |
| (K) Cinnamic acid/3-hydroxyanthranilate | N-(cinnamoyl)-3-hydroxyanthranilic acid | $C_{16}H_{13}NO_4$ | 282.077181 | 282.07725 | −0.24 | 4.61[b] |
| (L) o-Coumaric acid/3-hydroxyanthranilate | N-(2'-hydroxycinnamoyl)-3-hydroxyanthranilic acid | $C_{16}H_{13}NO_5$ | 298.072096 | 298.07235 | −0.85 | 4.96[b] |
| (M) m-Coumaric acid/3-hydroxyanthranilate | N-(3'-hydroxycinnamoyl)-3-hydroxyanthranilic acid | $C_{16}H_{13}NO_5$ | 298.072096 | 298.07219 | −0.32 | 4.49[b] |
| (N) 3-Methoxycinnamic acid/3-hydroxyanthranilate | N-(3'-methoxycinnamoyl)-3-hydroxyanthranilic acid | $C_{17}H_{15}NO_5$ | 312.087746 | 312.08799 | −0.78 | 5.87 |
| (O) 3,4-Dimethoxycinnamic acid/3-hydroxyanthranilate | N-(3',4'-dimethoxycinnamoyl)-3-hydroxyanthranilic acid | $C_{18}H_{17}NO_6$ | 342.098311 | 342.09843 | −0.3 | 5.95 |
| (P) 2,3-Dimethoxycinnamic acid/3-hydroxyanthranilate | N-(2',3'-dimethoxycinnamoyl)-3-hydroxyanthranilic acid | $C_{18}H_{17}NO_6$ | 342.098311 | 342.09831 | 0.0 | 5.92 |
| (Q) 2,5-Dimethoxycinnamic acid/3-hydroxyanthranilate | N-(2',5'-dimethoxycinnamoyl)-3-hydroxyanthranilic acid | $C_{18}H_{17}NO_6$ | 342.098311 | 342.09833 | −0.06 | 5.86 |

TABLE 2-continued

Characteristics of the second series of cinnamoyl anthranilates produced in yeast
and their identification based on dominant ion masses in ESI-MS spectra (FIG. 7).

| Precursors | Compound name | Formula | Theoretical mass [M − H]− | Measured mass [M − H]− | Mass accuracy[a] (ppm) | Retention time (min) |
|---|---|---|---|---|---|---|
| (R) 3,4,5-Trimethoxycinnamic acid/3-hydroxyanthranilate | N-(3',4',5'-trimethoxycinnamoyl)-3-hydroxyanthranilic acid | $C_{19}H_{19}NO_7$ | 372.108876 | 372.10836 | 1.4 | 5.79 |

[a]mass accuracy = [(theoretical mass-measured mass)/(theoretical mass)] × $1.10^6$.
[b]A 150-mm long column was used for the resolution of these compounds.

Discussion

Figure 5:
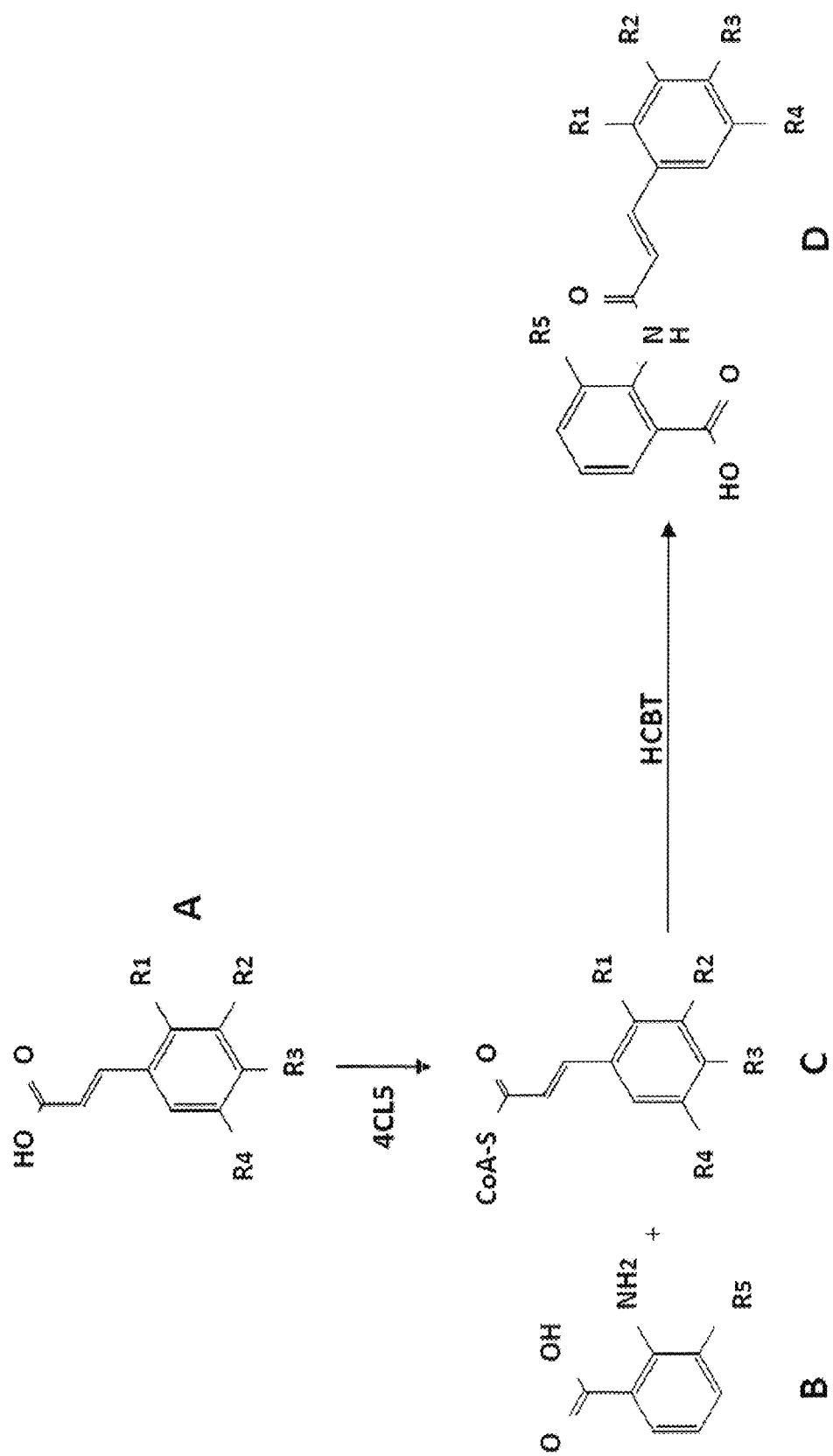
FIG. 5 shows the structures of the twenty-seven cinnamoyl anthranilates produced in recombinant yeast. Compound A can be.

We investigated the potential for yeast to produce various cinnamoyl anthranilates. Using an engineered yeast strain, we demonstrated the feasibility of synthesizing biologically as many as twenty-seven molecules, including the pharmaceutical drug tranilast (FIG. 5). The diversity of cinnamoyl anthranilates produced in this study reflects the broad substrate affinity of 4CL5 from *Arabidopsis*. The conversion of cinnamic acid, isoferulic acid, 4-methoxy-, 3-methoxy-, 3,4-dimethoxy-, 2,3-dimethoxy-, 2,5-dimethoxy-, 2,4-dimethoxy-, and 3,4,5-trimethoxy-cinnamic acids by 4CL5 has never been reported before, although it is well known that some 4CL in plants can accept these other substrates (Knobloch and Hahlbrock 1975; Funk and Brodelius 1990). After verifying that HCBT is active on p-coumaroyl-CoA and anthranilate in yeast (FIG. 3), we further showed its capacity to couple anthranilate and 3-hydroxyanthranilate to a broader range of cinnamoyl-CoA thioesters (Tables 2, FIG. 7). Our data confirm earlier reports showing that HCBT has affinity for p-coumaroyl-CoA and cinnamoyl-CoA in vitro, as well as for 3-hydroxyanthranilate albeit the conversion rate was 20% of that of anthranilate (Yang et al. 1997; Reinhard and Matern 1989).

p-Cinnamoyl-anthranilate, caffeoyl-anthranilate, and feruloyl-anthranilate produced in this study are oat-specific natural products named avenanthramide D, E, and F, respectively (Collins and Mullin 1988). In this work, we also report on newly characterized cinnamoyl-3-hydroxyanthranilates that are closely related to the cinnamoyl-5-hydroxyanthranilate avenanthramides found in oats (Collins 1989). Avenanthramides are present at low concentrations in oat groats (2.5-42 mg/kg) and are difficult to purify individually (Bratt et al. 2003). Radical-scavenging activity has been recently shown for a wide range of avenanthramides in vitro, as well as antioxidant and antigenotoxic activities (Fagerlund et al. 2009; Lee-Manion et al. 2009). For example, caffeoyl-5-hydroxyanthranilate (avn C) is capable of attenuating reactive oxygen species production in tissues of exercised rats and enhances activities of antioxidative enzymes (Ji et al. 2003). Furthermore, similarly to tranilast, avenanthramides are known to exert various anti-inflammatory and antiproliferative processes which have the potential to contribute to beneficial physiological effects (Liu et al. 2004; Nie et al. 2006; Sur et al. 2008). For example, avn C was shown to have antiproliferative effects on inflammation processes that contribute to atherosclerosis and restenosis after angioplasty (Guo et al. 2008). Interestingly, it was recently shown that p-coumaroyl-3-hydroxyanthranilate and caffeoyl-3-hydroxyanthranilate had antioxidant activities similar to those of their corresponding cinnamoyl-5-hydroxyanthranilate derivatives (Moglia et al. 2009). These results suggest that the cinnamoyl-3-hydroxyanthranilates biologically produced with 4CL-HCBT recombinant yeast could have similar health benefits as cinnamoyl-5-hydroxyanthranilate. Notably, we were unable to produce any hydroxycinnamoyl-5-hydroxyanthranilates when our 4CL5-HCBT yeast strain was grown in the presence of 5-hydroxyanthranilate and p-coumaric acid, caffeic acid, ferulic acid, or sinapic acids (data not shown). This result suggests that either HCBT does not use 5-hydroxyanthranilate as a substrate or that the substrate is not transported into the yeast cells. Replacement of HCBT with the oat-derived HHT1 in our engineered yeast strain could potentially lead to the synthesis of hydroxycinnamoyl-5-hydroxyanthranilates since the HHT1 enzyme was shown to use feruloyl-CoA and 5-hydroxyanthranilate as substrates for the production of feruloyl-5-hydroxyanthranilate (Yang et al. 2004). Finally, dihydroavenanthramide D (DHAvD), a synthetic hydrogenated analog of p-hydroxycinnamoyl-anthranilate, was found to reduce histamine-related skin disorders such as itching, redness and wheal. DHAvD is used as an active ingredient in cosmetic products and was also demonstrated to block the development of Type 1 diabetes in cytokine-treated mice (Heuschkel et al. 2008, 2009; Lv et al. 2009). Consequently, all three structurally-related hydroxycinnamoyl-anthranilates (i.e. m-, o-, and p-substituted) produced in this study could share similar health benefits, or alternatively, be used as direct precursors for chemical hydrogenation (Schmaus et al. 2006).

Our system allows the selective production of tranilast analogs, including twenty-four molecules that have never been identified from natural sources so far. Structural variability of cinnamoyl anthranilates is of particular interest to screen for derivatives with improved biological activity (Zammit et al. 2009). In this respect, additional molecules can potentially be biologically produced using the same strategy because the HCBT enzyme is known to accept other substrates such as benzoyl-CoA and salicyloyl-CoA (Yang et al. 1997); a plant 4CL enzyme active on benzoic acid was recently isolated and characterized in *Arabidopsis* (Kliebenstein et al. 2007).

The tranilast production presented in this study using yeast as a catalyst could be further optimized in various ways, in particular for the endogenous synthesis of anthranilate and 3,4-dimethoxycinnamic acid. Endogenous overproduction of anthranilate could be achieved directly from the conversion of glucose as recently demonstrated for an engineered strain of *Escherichia coli* (Balderas-Hernández et al. 2009). Endogenous production of p-coumaric acid from phenylalanine can be accomplished in yeast by expressing plant phenylalanine-ammonia lyase, cinnamic acid 4-hydroxylase, and cytochrome P450 reductase genes (Vanelli et al. 2007; Tantras et al. 2009). Furthermore, expression of the *Arabidopsis* p-coumaric acid 3-hydroxylase (CYP98A3) gene in yeast allows conversion of p-coumaric acid into caffeic acid (Nair et al. 2002). Caffeic acid represents a possible precursor for the production of 3,4-dimethoxycinnamic acid via two methoxylation reactions which could be catalyzed by the bacterial O-methyltransferases SafC (Nelson et al. 2007). Alternatively, co-expression of one of the well-characterized plant caffeic acid 3-O-methyltransferases with ferulic acid 4-O-methyltransferase could lead to the production of 3,4-dimethoxycinnamic acid from caffeic acid. Highly active ferulic acid 4-O-methyltransferase has not been discovered yet, however recent work based on site-directed mutagenesis allowed successful design of 4-O-methyltransferases with defined substrate specificities (Bhuiya and Liu 2010). Finally, optimizing 4CL activity for the conversion of 3,4-dimethyoxycinnamic acid should be considered to improve the biological synthesis of tranilast. The identification of residues involved in such activity already offers a potential for the engineering of 4CL enzymes (Lindermayr et al. 2003). All molecules produced by the recombinant yeast could be identified from the culture medium. This accumulation suggests the presence of an export mechanism potentially involving non-specific transporters. Identifying and overexpressing such transporters could further increase export of cinnamoyl anthranilates from yeast cells and would prevent any potential intracellular toxicity. A specific transporter could be also isolated from oats since cinnamoyl anthranilates typically accumulate in the oat cell wall (Okazaki et al. 2004).

REFERENCES CITED

Azuma H, Banno K, Yoshimura T (1976) Pharmacological properties of N-(3',4'-dimethoxycinnamoyl) anthranilic acid (N-5'), a new anti-atopic agent. Br J Pharmacol 58:483-488.

Balderas-Hernández V E, Sabido-Ramos A, Silva P, Cabrera-Valladares N, Hernández-Chávez G, Báez-Viveros J L, Martinez A, Bolivar F, Gosset G (2009) Metabolic engineering for improving anthranilate synthesis from glucose in *Escherichia coli*. Microb Cell Fact 2:8-19

Bhuiya M W, Liu C J (2010) Engineering monolignol 4-O-methyltransferases to modulate lignin biosynthesis. J Biol Chem 285:277-285

Bradford M M (1976) A rapid and sensitive method for the quantitation of microgram quantities of protein utilizing the principle of protein-dye binding. Anal Biochem 72:248-254

Branduardi P, Fossati T, Sauer M, Pagani R, Mattanovich D, Porro D (2007) Biosynthesis of vitamin C by yeast leads to increased stress resistance. P LoS One 2:e1092

Bratt K, Sunnerheim K, Bryngelsson S, Fagerlund A, Engman L, Andersson R E, Dimberg L H (2003) Avenanthramides in oats (*Avena sativa* L.) and structure-antioxidant activity relationships. J Agric Food Chem 51:594-600

Chakrabarti R, Subramaniam V, Abdalla S, Jothy S, Prud'homme G J (2009) Tranilast inhibits the growth and metastasis of mammary carcinoma. Anticancer Drugs 20:334-345

Chang M C, Keasling J D (2006) Production of isoprenoid pharmaceuticals by engineered microbes. Nat Chem Biol 2:674-681

Collins F W (1989) Oat phenolics: Avenanthramides, novel substituted N-cinnamoylanthranilate alkaloids from oat groats and hulls. J Agric Food Chem 37:60-66

Collins F W, Mullin W J (1988) High performance liquid chromatographic determination of avenanthramides, N-aroylanthranilic acid alkaloids from oats. J Chromatogr 445:363-370

Cui H, Gensini M, Kataria R, Twaddle T, Zhang J, Wadsworth S, Petrilli J, Rodgers K, diZerega G, Cooper K (2009) Reducing post-surgical adhesions utilizing a drug-enhanced device: sodium carboxymethylcellulose aqueous gel/poly(p-dioxanone) and Tranilast. Biomed Mater 4:015001

Engels B, Dahm P, Jennewein S (2008) Metabolic engineering of taxadiene biosynthesis in yeast as a first step towards Taxol (Paclitaxel) production. Metab Eng 10:201-206

Fagerlund A, Sunnerheim K, Dimberg L H (2009) Radical-scavenging and antioxidant activity of avenanthramides. Food Chem 113:550-556

Fosdick L S, Starke Jr A C (1940) Some alkamine esters of 4-acetylferulic and 3,4-dimethoxycinnamic acids. J Am Chem Soc 62:3352-3355

Funk C, Brodelius P E (1990) Phenylpropanoid Metabolism in Suspension Cultures of Vanilla planifolia Andr.: III. Conversion of 4-Methoxycinnamic Acids into 4-Hydroxybenzoic Acids Plant Physiol 94:102-108

Gietz R D, Woods R A (2002) Tranformation of yeast by the LiAc/SS carrier DNA/PEG method. Methods Enzymol 350:87-96

Guo W, Wise M L, Collins F W, Meydani M (2008) Avenanthramides, polyphenols from oats, inhibit IL-1β-induced NF-kB activation in endothelial cells. Free Radical Biol Med 44:415-429

Guo T, Chen W Q, Zhang C, Zhao Y X, Zhang Y (2009) Chymase activity is closely related with plaque vulnerability in a hamster model of atherosclerosis. Atherosclerosis 207:59-67

Hamberger B, Hahlbrock K (2004) The 4-coumarate:CoA ligase gene family in *Arabidopsis thaliana* comprises one rare, sinapate-activating and three commonly occurring isoenzymes. Proc Natl Acad Sci USA 101:2209-2214

Heuschkel S, Wohlrab J, Schmaus G, Neubert R H (2008) Modulation of dihydroavenanthramide D release and skin penetration by 1,2-alkanediols. Eur J Pharm Biopharm 70:239-247

Heuschkel S, Wohlrab J, Neubert R H (2009) Dermal and transdermal targeting of dihydroavenanthramide D using enhancer molecules and novel microemulsions. Eur J Pharm Biopharm 72:552-560

Horwitz S B (1994) How to make taxol from scratch. Nature 367:593-594

Isaji M, Miyata H, Ajisawa Y (1998) Tranilast: a new application in the cardiovascular field as an antiproliferative drug. Cardiovasc Drug Rev 16:288-299

Ji L L, Lay D, Chung E, Fu Y, Peterson D M (2003) Effects of avenanthramides on oxidant generation and antioxidant enzyme activity in exercised rats. Nutr Res 23:1579-1590

Kliebenstein D J, D'Auria J C, Behere A S, Kim J H, Gunderson K L, Breen J N, Lee G, Gershenzon J, Last R L, Jander G (2007) Characterization of seed-specific benzoyloxyglucosinolate mutations in *Arabidopsis thaliana*. Plant J 51:1062-1076

Knobloch K H, Hahlbrock K (1975) Isoenzymes of p-coumarate: CoA ligase from cell suspension cultures of *Glycine max*. Eur J Biochem 52:311-320

Komatsu H, Kojima M, Tsutsumi N, Hamano S, Kusama H, Ujiie A, Ikeda S, Nakazawa M (1988) Study of the mechanism of inhibitory action of tranilast on chemical mediator release. Jpn J Pharmacol 46:43-51

Konneh M (1998) Tranilast, Kissei Pharmaceuticals. Idrugs 1:141-146

Kunkel T A (1985) Rapid and efficient site-specific mutagenesis without phenotypic selection. Proc Natl Acad Sci USA 82:488-492

Lee-Manion A M, Price R K, Strain J J, Dimberg L H, Sunnerheim K, Welch R W (2009) In vitro antioxidant activity and antigenotoxic affects of avenanthramides and related compounds. J Agric Food Chem 57:10619-10624

Limem I, Guedon E, Hehn A, Bourgaud F, Ghedira L, Engasser J-M, Ghoul M (2008) Production of phenylpropanoid compounds by recombinant microorganisms expressing plant-specific biosynthesis genes. Process Biochem 43:463-479

Lindermayr C, Fliegmann J, Ebel J (2003) Deletion of a single amino acid residue from different 4-coumarate: CoA ligases from soybean results in the generation of new substrate specificities. J Biol Chem 278:2781-2786

Liu L, Zubik L, Collins F W, Marko M, Meydani M (2004) The antiatherogenic potential of oat phenolic compounds. Artherosclerosis 175:39-49.

Loqué D, Lalonde S, Looger L L, von Wirén N, Frommer W B (2007) A cytosolic trans-activation domain essential for ammonium uptake. Nature 446:195-198

Lv N, Song M Y, Lee Y R, Choi H N, Kwon K B, Park J W, Park B H (2009) Dihydroavenanthramide D protects pancreatic beta-cells from cytokine and streptozotocin toxicity. Biochem Biophys Res Commun 387:97-102

Moglia A, Comino C, Lanteri S, de Vos R, de Waard P, van Beek T A, Goitre L, Retta S F, Beekwilder, J (2010) Production of novel antioxidative phenolic amides through heterologous expression of the plant's chlorogenic acid biosynthesis genes in yeast. Metab Eng 12:223-232

Mukai N, Masaki K, Fujii T, Kawamukai M, Iefuji H (2010) PAD1 and FDC1 are essential for the decarboxylation of phenylacrylic acids in Saccharomyces cerevisiae. J Biosc Bioeng 109:564-569

Nair R B, Xia Q, Kartha C J, Kurylo E, Hirji R N, Datla R, Selvaraj G (2002) Arabidopsis CYP98A3 mediating aromatic 3-hydroxylation. Developmental regulation of the gene, and expression in yeast. Plant Physiol 130:210-220

Nelson J T, Lee J, Sims J W, Schmidt E W (2007) Characterization of SafC, a catechol 4-O-methyltransferase involved in saframycin biosynthesis. Appl Environ Microbiol 73:3575-3580

Nie L, Wise M L, Peterson D M, Meydani M (2006) Avenanthramide, a polyphenol from oats, inhibits vascular smooth muscle cell proliferation and enhances nitric oxide production. Atherosclerosis 186:260-266

Ogawa Y, Dogru M, Uchino M, Tatematsu Y, Kamoi M, Yamamoto Y, Ogawa J, Ishida R, Kaido M, Hara S, Matsumoto Y, Kawakita T, Okamoto S, Tsubota K (2010) Topical tranilast for treatment of the early stage of mild dry eye associated with chronic GVHD. Bone Marrow Transplant 45:565-569

Okazaki Y, Isobe T, Iwata Y, Matsukawa T, Matsuda F, Miyagawa H, Ishihara A, Nishioka T, Iwamura H (2004) Metabolism of avenanthramide phytoalexins in oat. Plant J 39:560-572

Okuda M, Ishikawa T, Saito Y, Shimizu T, Baba S (1984) A clinical evaluation of N-5' with perennial-type allergic rhinitis—a test by the multi-clinic, intergroup, double-blind comparative method. Ann Allergy 53:178-185

Oshitani N, Yamagami H, Watanabe K, Higuchi K, Arakawa T (2007) Long-term prospective pilot study with tranilast for the prevention of stricture progression in patients with Crohn's disease. Gut 56:599-600

Pae H O, Jeong S O, Koo B S, Ha H Y, Lee K M, Chung H T (2002) Tranilast, an orally active anti-allergic drug, up-regulates the anti-inflammatory heme oxygenase-1 expression but down-regulates the pro-inflammatory cyclooxygenase-2 and inducible nitric oxide synthase expression in RAW264.7 macrophages. Biochem Biophys Res Commun 371:361-365

Park M, Kang K, Park S, Kim Y S, Ha S—H, Lee S W, Ahn M-J, Bae J-M, Back K (2008) Expression of serotonin derivative synthetic genes on a single self-processing polypeptide and the production of serotonin derivatives in microbes. Appl Microbiol Biotechnol 81: 43-49

Platten M, Ho P P, Youssef S, Fontoura P, Garren H, Hur E M, Gupta R, Lee L Y, Kidd B A, Robinson W H, Sobel R A, Selley M L, Steinman L (2005) Treatment of autoimmune neuroinflammation with a synthetic tryptophan metabolite. Science 310:850-855

Ponchet M, Favre-Bonvin J, M Hauteville M, Ricci P (1988) Dianthramides (N-benzoyl and N-paracoumarylanthranilic acid derivatives) from elicited tissues of Dianthus caryophyllus. Phytochemistry 27:725-730

Prud'homme G J (2007) Pathobiology of transforming growth factor beta in cancer, fibrosis and immunologic disease, and therapeutic considerations. Lab Invest 87:1077-1091

Reinhard K, Matern U (1989) The biosynthesis of phytoalexins in Dianthus caryophyllus L. cell cultures: induction of benzoyl-CoA:anthranilate N-benzoyltransferase activity. Arch Biochem Biophys 275:295-301

Ro D K, Paradise E M, Ouellet M, Fisher K J, Newman K L, Ndungu J M, Ho K A, Eachus R A, Ham T S, Kirby J, Chang M C, Withers S T, Shiba Y, Sarpong R, Keasling J D (2006) Production of the antimalarial drug precursor artemisinic acid in engineered yeast. Nature 440:940-943

Schmaus G, Joppe H, Herrmann M, Sabater-Luntzel C, Vossing T (2006) Anthranilic acid amides and derivatives thereof as cosmetic and pharmaceutical agents. U.S. Patent 20060089413

Shiota N, Kovanen P T, Eklund K K, Shibata N, Shimoura K, Niibayashi T, Shimbori C, Okunishi H (2010) The anti-allergic compound tranilast attenuates inflammation and inhibits bone destruction in collagen-induced arthritis in mice. Br J Pharmacol 159:626-635

Sun X, Suzuki K, Nagata M, Kawauchi Y, Yano M, Ohkoshi S, Matsuda Y, Kawachi H, Watanabe K, Asakura H, Aoyagi Y (2010) Rectal administration of tranilast ameliorated acute colitis in mice through increased expression of heme oxygenase-1. Pathol Int 60:93-101

Sur R, Nigam A, Grote D, Liebel F, Southall M D (2008) Avenanthramides, polyphenols from oats, exhibit anti-inflammatory and anti-itch activity. Arch Dermatol Res 25:1-6

Szczebara F M, Chandelier C, Villeret C, Masurel A, Bourot S, Duport C, Blanchard S, Groisillier A, Testet E, Costaglioli P, Cauet G, Degryse E, Balbuena D, Winter J, Achstetter T, Spagnoli R, Pompon D, Dumas B (2003) Total biosynthesis of hydrocortisone from a simple carbon source in yeast. Nat Biotechnol 21:143-149

Tamai H, Katoh K, Yamaguchi T, Hayakawa H, Kanmatsuse K, Haze K, Aizawa T, Nakanishi S, Suzuki S, Suzuki T, Takase S, Nishikawa H, Katoh O (2002) The impact of tranilast on restenosis after coronary angioplasty: the Second Tranilast Restenosis Following Angioplasty Trial (TREAT-2). Am Heart J 143:506-513

Tan S M, Zhang Y, Cox A J, Kelly D J, Qi W (2010) Tranilast attenuates the up-regulation of thioredoxin-interacting protein and oxidative stress in an experimental model of diabetic nephropathy. Nephrol Dial Transplant doi: 10.1093/ndt/gfq355

Trantas E, Panopoulos N, Ververidis F (2009) Metabolic engineering of the complete pathway leading to heterologous biosynthesis of various flavonoids and stilbenoids in *Saccharomyces cerevisiae*. Metab Eng 11:355-366

Vannelli T, Wei Qi W, Sweigard J, Gatenby A A, Sariaslani F S (2007) Production of p-hydroxycinnamic acid from glucose in *Saccharomyces cerevisiae* and *Escherichia coli* by expression of heterologous genes from plants and fungi. Metab Eng 9:142-151

Wieczorke R, Krampe S, Weierstall T, Freidel K, Hollenberg C P, Boles E (1999) Concurrent knock-out of at least 20 transporter genes is required to block uptake of hexoses in *Saccharomyces cerevisiae*. FEBS Lett 464:123-128

Winzeler E A, Shoemaker D D, Astromoff A et al (1999) Functionnal Characterization of the *S. cerevisiae* genome by deletion and parallel analysis. Science 285:901-906

Yang Q, Reinhard K, Schiltz E, Matern U (1997) Characterization and heterologous expression of hydroxycinnamoyUbenzoyl-CoA:anthranilate N-hydroxycinnamoyl/benzoyltransferase from elicited cell cultures of carnation, *Dianthus caryophyllus* L. Plant Mol Biol 35:777-789

Yang Q, Trinh H X, Imai S, Ishihara A, Zhang L, Nakayashiki H, Tosa Y, Mayama S (2004) Analysis of the involvement of hydroxyanthranilate hydroxycinnamoyl-transferase and caffeoyl-CoA 3-O-methyltransferase in phytoalexin biosynthesis in oat. Mol Plant Microb Interact 17:81-89

Zammit S C, Cox A J, Gow R M, Zhang Y, Gilbert R E, Krum H, Kelly D J, Williams S J (2009) Evaluation and optimization of antifibrotic activity of cinnamoyl anthranilates. Bioorg Med Chem Lett 19:7003-7006

The above cited references are incorporated herein by reference.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A culture medium comprising: (A) a genetically modified host cell comprising (a) an hydroxycinnamoyl/benzoyl-CoA:anthranilate N-hydroxycinnamoyl/benzoyltransferase (HCBT, EC 2.3.1.144) having an amino acid sequence at least 70% identical to SEQ ID NO:1 capable of catalyzing the formation of a cinnamoyl anthranilate, or analog thereof, from a cinnamoyl-CoA, or analog thereof, and an anthranilate, or analog thereof, and (b) a 4-coumarate:CoA ligase (4CL, EC 6.2.1.12) having an amino acid sequence at least 70% identical to SEQ ID NO:3 capable of catalyzing the formation of a cinnamic acid, or analog thereof, into a corresponding cinnamoyl-CoA thioester, or analog thereof; and (B) a compound having the following chemical structure:

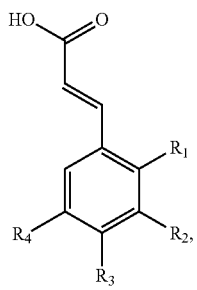

wherein $R_1$ and $R_2$ are each H; $R_3$ is $OCH_3$; and $R_4$ is $OCH_3$.

2. The culture medium of claim 1, wherein the HCBT has the amino acid sequence of SEQ ID NO:1.

3. The culture medium of claim 1, wherein the 4CL has the amino acid sequence of SEQ ID NO:3.

4. A method of producing a cinnamoyl anthranilate, or analog thereof, comprising: culturing the genetically modified host cell of claim 1 under a suitable condition such that the culturing results in the genetically modified host cell producing an cinnamoyl anthranilate, or analog thereof.

5. The method of claim 4, further comprising isolating the cinnamoyl anthranilate, or analog thereof, from the host cell and/or culture medium.

6. The culture medium of claim 1, wherein the HCBT has an amino acid sequence at least 80% identical to SEQ ID NO:1.

7. The culture medium of claim 6, wherein the HCBT has an amino acid sequence at least 90% identical to SEQ ID NO:1.

8. The culture medium of claim 7, wherein the HCBT has an amino acid sequence at least 95% identical SEQ ID NO:1.

9. The culture medium of claim 1, wherein the 4CL has an amino acid sequence at least 80% identical to SEQ ID NO:3.

10. The culture medium of claim 9, wherein the 4CL has an amino acid sequence at least 90% identical to SEQ ID NO:3.

11. The culture medium of claim 10, wherein the 4CL has an amino acid sequence at least 95% identical SEQ ID NO:3.

12. The culture medium of claim 1, wherein the host cell is a bacteria of a genus selected from the group consisting of *Escherichia, Enterobacter, Azotobacter, Erwinia, Bacillus, Pseudomonas, Klebsielia, Proteus, Salmonella, Serratia, Shigella, Rhizobia, Vitreoscilla, Synechococcus, Synechocystis*, and *Paracoccus*.

13. The culture medium of claim 1, wherein the host cell is a yeast.

14. The culture medium of claim 13, wherein the yeast is *Saccharomyces cerevisiae*.

* * * * *

SEQUENCE LISTING

```
<160> NUMBER OF SEQ ID NOS: 10

<210> SEQ ID NO 1
<211> LENGTH: 445
<212> TYPE: PRT
<213> ORGANISM: Dianthus caryophyllus

<400> SEQUENCE: 1

Met Ser Ile His Ile Lys Gln Ser Thr Met Val Arg Pro Ala Glu Glu
1               5                   10                  15

Thr Pro Asn Lys Ser Leu Trp Leu Ser Lys Ile Asp Met Ile Leu Arg
            20                  25                  30

Thr Pro Tyr Ser His Thr Gly Ala Val Leu Ile Tyr Lys Gln Pro Asp
        35                  40                  45

Asn Asn Glu Asp Asn Ile Gln Pro Ser Ser Ser Met Tyr Phe Asp Ala
    50                  55                  60

Asn Ile Leu Ile Glu Ala Leu Ser Lys Ala Leu Val Pro Tyr Tyr Pro
65                  70                  75                  80

Met Ala Gly Arg Leu Lys Ile Asn Gly Asp Arg Tyr Glu Ile Asp Cys
                85                  90                  95

Asn Gly Glu Gly Ala Leu Phe Val Glu Ala Glu Ser Ser His Val Leu
            100                 105                 110

Glu Asp Phe Gly Asp Phe Arg Pro Asn Asp Glu Leu His Arg Val Met
        115                 120                 125

Val Pro Thr Cys Asp Tyr Ser Lys Gly Ile Ser Ser Phe Pro Leu Leu
    130                 135                 140

Met Val Gln Leu Thr Arg Phe Arg Cys Gly Gly Val Ser Ile Gly Phe
145                 150                 155                 160

Ala Gln His His His Val Cys Asp Arg Met Ser His Phe Glu Phe Asn
                165                 170                 175

Asn Ser Trp Ala Arg Ile Ala Lys Gly Leu Leu Pro Ala Leu Glu Pro
            180                 185                 190

Val His Asp Arg Tyr Leu His Leu Cys Pro Arg Asn Pro Pro Gln Ile
        195                 200                 205
```

```
Lys Tyr Thr His Ser Gln Phe Glu Pro Phe Val Pro Ser Leu Pro Lys
    210                 215                 220

Glu Leu Leu Asp Gly Lys Thr Ser Lys Ser Gln Thr Leu Phe Lys Leu
225                 230                 235                 240

Ser Arg Glu Gln Ile Asn Thr Leu Lys Gln Lys Leu Asp Trp Ser Asn
                    245                 250                 255

Thr Thr Thr Arg Leu Ser Thr Tyr Glu Val Val Ala Gly His Val Trp
                260                 265                 270

Arg Ser Val Ser Lys Ala Arg Gly Leu Ser Asp His Glu Glu Ile Lys
            275                 280                 285

Leu Ile Met Pro Val Asp Gly Arg Ser Arg Ile Asn Asn Pro Ser Leu
290                 295                 300

Pro Lys Gly Tyr Cys Gly Asn Val Val Phe Leu Ala Val Cys Thr Ala
305                 310                 315                 320

Thr Val Gly Asp Leu Ala Cys Asn Pro Leu Thr Asp Thr Ala Gly Lys
                325                 330                 335

Val Gln Glu Ala Leu Lys Gly Leu Asp Asp Asp Tyr Leu Arg Ser Ala
                340                 345                 350

Ile Asp His Thr Glu Ser Lys Pro Asp Leu Pro Val Pro Tyr Met Gly
            355                 360                 365

Ser Pro Glu Lys Thr Leu Tyr Pro Asn Val Leu Val Asn Ser Trp Gly
370                 375                 380

Arg Ile Pro Tyr Gln Ala Met Asp Phe Gly Trp Gly Asn Pro Thr Phe
385                 390                 395                 400

Phe Gly Ile Ser Asn Ile Phe Tyr Asp Gly Gln Cys Phe Leu Ile Pro
                405                 410                 415

Ser Gln Asn Gly Asp Gly Ser Met Thr Leu Ala Ile Asn Leu Phe Ser
            420                 425                 430

Ser His Leu Ser Leu Phe Lys Lys His Phe Tyr Asp Phe
            435                 440                 445

<210> SEQ ID NO 2
<211> LENGTH: 431
<212> TYPE: PRT
<213> ORGANISM: Ipomoea batatas

<400> SEQUENCE: 2

Met Ala Ser Glu Lys Phe Lys Ile Ser Ile Lys Glu Ser Thr Met Val
1               5                   10                  15

Lys Pro Ala Lys Pro Thr Pro Ala Lys Arg Leu Trp Asn Ser Asn Leu
                20                  25                  30

Asp Leu Ile Val Gly Arg Ile His Leu Leu Thr Val Tyr Phe Tyr Arg
                35                  40                  45

Pro Asn Gly Ser Pro Asn Phe Phe Asp Ser Lys Val Met Lys Glu Ala
            50                  55                  60

Leu Ser Asn Val Leu Val Ser Phe Tyr Pro Met Ala Gly Arg Leu Ala
65                  70                  75                  80

Arg Asp Gly Glu Gly Arg Ile Glu Ile Asp Cys Asn Glu Glu Gly Val
                85                  90                  95

Leu Phe Val Glu Ala Glu Ser Asp Ala Cys Val Asp Asp Phe Gly Asp
                100                 105                 110

Phe Thr Pro Ser Leu Glu Leu Arg Lys Phe Ile Pro Thr Val Asp Thr
            115                 120                 125

Ser Gly Asp Ile Ser Ser Phe Pro Leu Ile Ile Phe Gln Val Thr Arg
```

```
                130             135             140
    Phe Lys Cys Gly Gly Val Cys Leu Gly Thr Gly Val Phe His Thr Leu
    145             150             155             160

Ser Asp Gly Val Ser Ser Leu His Phe Ile Asn Thr Trp Ser Asp Met
                165             170             175

Ala Arg Gly Leu Ser Val Ala Ile Pro Pro Phe Ile Asp Arg Thr Leu
                180             185             190

Leu Arg Ala Arg Asp Pro Thr Pro Ala Phe Glu His Ser Glu Tyr
                195             200             205

Asp Gln Pro Pro Lys Leu Lys Ser Val Pro Glu Ser Lys Arg Gly Ser
                210             215             220

Ser Ala Ser Thr Thr Met Leu Lys Ile Thr Pro Glu Gln Leu Ala Leu
    225             230             235             240

Leu Lys Thr Lys Ser Lys His Glu Gly Ser Thr Tyr Glu Ile Leu Ala
                245             250             255

Ala His Ile Trp Arg Cys Ala Cys Lys Ala Arg Gly Leu Thr Asp Asp
                260             265             270

Gln Ala Thr Lys Leu Tyr Val Ala Thr Asp Gly Arg Ser Arg Leu Cys
                275             280             285

Pro Pro Leu Pro Pro Gly Tyr Leu Gly Asn Val Val Phe Thr Ala Thr
                290             295             300

Pro Met Ala Glu Ser Gly Glu Leu Gln Ser Glu Pro Leu Thr Asn Ser
    305             310             315             320

Ala Lys Arg Ile His Ser Ala Leu Ser Arg Met Asp Asp Glu Tyr Leu
                325             330             335

Arg Ser Ala Leu Asp Phe Leu Glu Cys Gln Pro Asp Leu Ser Lys Leu
                340             345             350

Ile Arg Gly Ser Asn Tyr Phe Ala Ser Pro Asn Leu Asn Ile Asn Ser
                355             360             365

Trp Thr Arg Leu Pro Val His Glu Ser Asp Phe Gly Trp Gly Arg Pro
                370             375             380

Ile His Met Gly Pro Ala Cys Ile Leu Tyr Glu Gly Thr Val Tyr Ile
    385             390             395             400

Leu Pro Ser Pro Asn Lys Asp Arg Thr Leu Ser Leu Ala Val Cys Leu
                405             410             415

Asp Ala Glu His Met Pro Leu Phe Lys Glu Phe Leu Tyr Asp Phe
                420             425             430

<210> SEQ ID NO 3
<211> LENGTH: 570
<212> TYPE: PRT
<213> ORGANISM: Arabidopsis thaliana

<400> SEQUENCE: 3

Met Val Leu Gln Gln Gln Thr His Phe Leu Thr Lys Lys Ile Asp Gln
    1               5               10              15

Glu Asp Glu Glu Glu Glu Pro Ser His Asp Phe Ile Phe Arg Ser Lys
                20              25              30

Leu Pro Asp Ile Phe Ile Pro Asn His Leu Pro Leu Thr Asp Tyr Val
                35              40              45

Phe Gln Arg Phe Ser Gly Asp Gly Asp Gly Asp Ser Ser Thr Thr Cys
                50              55              60

Ile Ile Asp Gly Ala Thr Gly Arg Ile Leu Thr Tyr Ala Asp Val Gln
    65              70              75              80
```

-continued

```
Thr Asn Met Arg Arg Ile Ala Ala Gly Ile His Arg Leu Gly Ile Arg
             85                  90                  95

His Gly Asp Val Val Met Leu Leu Pro Asn Ser Pro Glu Phe Ala
        100                 105                 110

Leu Ser Phe Leu Ala Val Ala Tyr Leu Gly Ala Val Ser Thr Thr Ala
        115                 120                 125

Asn Pro Phe Tyr Thr Gln Pro Glu Ile Ala Lys Gln Ala Lys Ala Ser
        130                 135                 140

Ala Ala Lys Met Ile Ile Thr Lys Lys Cys Leu Val Asp Lys Leu Thr
145                 150                 155                 160

Asn Leu Lys Asn Asp Gly Val Leu Ile Val Cys Leu Asp Asp Asp Gly
                165                 170                 175

Asp Asn Gly Val Val Ser Ser Ser Asp Asp Gly Cys Val Ser Phe Thr
        180                 185                 190

Glu Leu Thr Gln Ala Asp Glu Thr Glu Leu Leu Lys Pro Lys Ile Ser
        195                 200                 205

Pro Glu Asp Thr Val Ala Met Pro Tyr Ser Ser Gly Thr Thr Gly Leu
        210                 215                 220

Pro Lys Gly Val Met Ile Thr His Lys Gly Leu Val Thr Ser Ile Ala
225                 230                 235                 240

Gln Lys Val Asp Gly Glu Asn Pro Asn Leu Asn Phe Thr Ala Asn Asp
                245                 250                 255

Val Ile Leu Cys Phe Leu Pro Met Phe His Ile Tyr Ala Leu Asp Ala
                260                 265                 270

Leu Met Leu Ser Ala Met Arg Thr Gly Ala Ala Leu Leu Ile Val Pro
        275                 280                 285

Arg Phe Glu Leu Asn Leu Val Met Glu Leu Ile Gln Arg Tyr Lys Val
        290                 295                 300

Thr Val Val Pro Val Ala Pro Pro Val Val Leu Ala Phe Ile Lys Ser
305                 310                 315                 320

Pro Glu Thr Glu Arg Tyr Asp Leu Ser Ser Val Arg Ile Met Leu Ser
                325                 330                 335

Gly Ala Ala Thr Leu Lys Lys Glu Leu Glu Asp Ala Val Arg Leu Lys
                340                 345                 350

Phe Pro Asn Ala Ile Phe Gly Gln Gly Tyr Gly Met Thr Glu Ser Gly
        355                 360                 365

Thr Val Ala Lys Ser Leu Ala Phe Ala Lys Asn Pro Phe Lys Thr Lys
        370                 375                 380

Ser Gly Ala Cys Gly Thr Val Ile Arg Asn Ala Glu Met Lys Val Val
385                 390                 395                 400

Asp Thr Glu Thr Gly Ile Ser Leu Pro Arg Asn Lys Ser Gly Glu Ile
                405                 410                 415

Cys Val Arg Gly His Gln Leu Met Lys Gly Tyr Leu Asn Asp Pro Glu
                420                 425                 430

Ala Thr Ala Arg Thr Ile Asp Lys Asp Gly Trp Leu His Thr Gly Asp
        435                 440                 445

Ile Gly Phe Val Asp Asp Asp Glu Ile Phe Ile Val Asp Arg Leu
        450                 455                 460

Lys Glu Leu Ile Lys Phe Lys Gly Tyr Gln Val Ala Pro Ala Glu Leu
465                 470                 475                 480

Glu Ala Leu Leu Ile Ser His Pro Ser Ile Asp Asp Ala Ala Val Val
                485                 490                 495

Ala Met Lys Asp Glu Val Ala Asp Glu Val Pro Val Ala Phe Val Ala
```

```
                500            505             510
Arg Ser Gln Gly Ser Gln Leu Thr Glu Asp Asp Val Lys Ser Tyr Val
            515                 520                 525

Asn Lys Gln Val Val His Tyr Lys Arg Ile Lys Met Val Phe Phe Ile
        530                 535                 540

Glu Val Ile Pro Lys Ala Val Ser Gly Lys Ile Leu Arg Lys Asp Leu
545                 550                 555                 560

Arg Ala Lys Leu Glu Thr Met Cys Ser Lys
                565                 570
```

<210> SEQ ID NO 4
<211> LENGTH: 47
<212> TYPE: DNA
<213> ORGANISM: Artificial Sequence
<220> FEATURE:
<223> OTHER INFORMATION: Primer for inserting 2 SphI restriction sites
      into the yeast shuttle vector p426

<400> SEQUENCE: 4
cgaaattgtt cctacgagct cgcatgcttt tgttcccttt agtgagg              47

<210> SEQ ID NO 5
<211> LENGTH: 47
<212> TYPE: DNA
<213> ORGANISM: Artificial Sequence
<220> FEATURE:
<223> OTHER INFORMATION: Primer for inserting 2 SphI restriction sites
      into the yeast shuttle vector p426

<400> SEQUENCE: 5
gactcactat agggcgaatt ggcatgcggc cgcaaattaa agccttc               47

<210> SEQ ID NO 6
<211> LENGTH: 47
<212> TYPE: DNA
<213> ORGANISM: Artificial Sequence
<220> FEATURE:
<223> OTHER INFORMATION: Primer for inserting a NotI restriction site
      between PHXT7 and TCYC1 of the yeast shuttle vector p426

<400> SEQUENCE: 6
cataactaat tacatgactc gagcggccgc ccgggggatc cactaga              47

<210> SEQ ID NO 7
<211> LENGTH: 30
<212> TYPE: DNA
<213> ORGANISM: Artificial Sequence
<220> FEATURE:
<223> OTHER INFORMATION: Forward primer for cloning the 4CL5 gene from
      Arabidopsis thaliana

<400> SEQUENCE: 7
gcggccgcat ggtgctccaa caacaaacgc                                 30

<210> SEQ ID NO 8
<211> LENGTH: 30
<212> TYPE: DNA
<213> ORGANISM: Artificial Sequence
<220> FEATURE:
<223> OTHER INFORMATION: Reverse primer for cloning the 4CL5 gene from
      Arabidopsis thaliana

<400> SEQUENCE: 8
gcggccgcct atttagagca catggtttcc                                 30

```
<210> SEQ ID NO 9
<211> LENGTH: 10
<212> TYPE: PRT
<213> ORGANISM: Artificial Sequence
<220> FEATURE:
<223> OTHER INFORMATION: AttB2 peptide

<400> SEQUENCE: 9

Asp Pro Ala Phe Leu Tyr Lys Val Val Asp
1               5                   10

<210> SEQ ID NO 10
<211> LENGTH: 8
<212> TYPE: PRT
<213> ORGANISM: Artificial Sequence
<220> FEATURE:
<223> OTHER INFORMATION: Portion of AttB2 peptide

<400> SEQUENCE: 10

Pro Ala Phe Leu Tyr Lys Val Val
1               5
```